(12) United States Patent
Urano et al.

(10) Patent No.: US 10,441,574 B2
(45) Date of Patent: Oct. 15, 2019

(54) TREATMENT FOR WOLFRAM SYNDROME AND OTHER ENDOPLASMIC RETICULUM STRESS DISORDERS

(71) Applicants: Fumihiko Urano, St. Louis, MO (US); Simin Lu, St. Louis, MO (US)

(72) Inventors: Fumihiko Urano, St. Louis, MO (US); Simin Lu, Shanghai (CN)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 15/526,663

(22) PCT Filed: Nov. 13, 2015

(86) PCT No.: PCT/US2015/060598
§ 371 (c)(1),
(2) Date: May 12, 2017

(87) PCT Pub. No.: WO2016/077706
PCT Pub. Date: May 19, 2016

(65) Prior Publication Data
US 2018/0214416 A1    Aug. 2, 2018

Related U.S. Application Data

(60) Provisional application No. 62/079,480, filed on Nov. 13, 2014.

(51) Int. Cl.
| | | |
|---|---|---|
| *A61K 31/4178* | (2006.01) | |
| *A61P 25/00* | (2006.01) | |
| *A61K 38/17* | (2006.01) | |
| *A61K 45/06* | (2006.01) | |
| *A61K 9/00* | (2006.01) | |

(52) U.S. Cl.
CPC ........ *A61K 31/4178* (2013.01); *A61K 9/0019* (2013.01); *A61K 38/177* (2013.01); *A61K 45/06* (2013.01); *A61P 25/00* (2018.01)

(58) Field of Classification Search
None
See application file for complete search history.

(56) References Cited

U.S. PATENT DOCUMENTS

| | | | |
|---|---|---|---|
| 4,861,790 A | 8/1989 | White, Jr. et al. | |
| 7,851,589 B2 | 12/2010 | Yano et al. | |
| 8,664,251 B1 | 3/2014 | Fomina | |
| 2004/0006124 A1* | 1/2004 | Dong ................ | A61K 31/4166 514/422 |
| 2007/0049630 A1* | 3/2007 | Dong ................ | A61K 31/00 514/389 |
| 2007/0066638 A1* | 3/2007 | Dong ................ | A61K 31/00 514/282 |
| 2008/0045495 A1 | 2/2008 | Hiesberger et al. | |
| 2009/0143279 A1 | 6/2009 | Mootha et al. | |
| 2009/0203605 A1 | 8/2009 | Segatori et al. | |
| 2009/0281040 A1 | 11/2009 | Urano et al. | |

FOREIGN PATENT DOCUMENTS

| | | | |
|---|---|---|---|
| WO | 9405287 A1 | 3/1994 | |
| WO | 2009100037 A1 | 8/2009 | |
| WO | 2012177997 A1 | 12/2012 | |
| WO | 2013070981 A2 | 5/2013 | |
| WO | 2014049366 A1 | 4/2014 | |
| WO | WO-2014049366 A1 * | 4/2014 | ........... A61K 31/436 |
| WO | 2014118527 A1 | 8/2014 | |

OTHER PUBLICATIONS

NDA 17443/S-/S-043/S-046/S-048/S-049 (Oct. 2011).*
Rohayem et al., "Diabetes and Neurodegeneration in Wolfram Syndrome," Diabetes Care, vol. 34, Jul. 2011.*
Dantrium® (dantrolene sodium) Capsules, Information Sheet, Aug. 2008, JHP Pharmaceuticals, Rochester, NY 48307, 5 pages.
Dantrium® Intravenous (dantrolene sodium for injection), Information Sheet, Nov. 2008, JHP Pharmaceuticals, Rochester, NY 48307, 1 page.
Revonto® (dantrolene sodium for injection), Information Sheet, Jun. 2011, DSM Pharmaceuticals, Inc., Greenville, NC 27834, 2 pages.
International Search Report and Written Opinion issued in PCT/US15/60598, dated Feb. 2, 2016, 10 pages.
Akiyama, M., et al., "Increased Insulin Demand Promotes While Pioglitazone Prevents Pancreatic β Cell Apoptosis in Wfs1 Knockout Mice," 2009, Diabetologia, 52/4:653-663, 11 pages.
Amr, S., et al., "A Homozygous Mutation in a Novel Zinc-Finger Protein, ERIS, is Responsible for Wolfram Syndrome 2," 2007, Am J of Human Gen, 81/4: 673-683, 11 pages.
Bachar-Wikstrom, E., et al., "Stimulation of Autophagy Improves Endoplasmic Reticulum Stress-Induced Diabetes," 2013, Diabetes, 62/4:1227-1237, 11 pages.
Barrett, T.G., et al., "Neurodegeneration and Diabetes: UK Nationwide Study of Wolfram (DIDMOAD) Syndrome," 1995, Lancet, 346/8988: 1458-1463, 3 pages (Abstract Only).
Barrett, T.G., et al., "Wolfram (DIDMOAD) Syndrome," 1997, J Med Genet, 34/10: 838-841, 4 pages.
Bonnycastle, L.L., et al., "Autosomal Dominant Diabetes Arising From a Wolfram Syndrome 1 Mutation," 2013, Diabetes 62/11:3943-3950, 8 pages.
Campos, E.C., et al., "Calpain-mediated Dystrophin Disruption May Be a Potential Structural Culprit Behind Chronic Doxorubicin-Induced Cardiomyopathy," 2011, Euro J Pharmac, 670:541-553, 13 pages.
Cao, S.S., et al., "Targeting Endoplasmic Reticulum Stress in Matabolic Disease," 2013, Expert Opin Ther Targets, 17/4:437-448, 12 pages.
Chen, Y.F., et al., "Cisd2 Deficiency Drives Premature Aging and Causes Mitochondria-Mediated Defects in Mice," 2009, Genes Dev, 23/10:1183-1194, 12 pages.
Dykes, M.H., "Evaluation of a Muscle Relaxant: Dantrolene Sodium (Dantrium)," 1975, JAMA, 231/8:862-864, 3 pages (Abstract Only).

(Continued)

*Primary Examiner* — Jared Barsky
(74) *Attorney, Agent, or Firm* — Stinson LLP

(57) ABSTRACT

The present invention generally relates to a method of treating or preventing an endoplasmic reticulum stress disorder in subjects, such as a method of treating or preventing Wolfram syndrome.

20 Claims, 37 Drawing Sheets

Specification includes a Sequence Listing.

(56) References Cited

OTHER PUBLICATIONS

Fonseca, S.G., et al., "WFS1 Is a Novel Component of the Unfolded Protein Response and Maintains Homeostasis of the Endoplasmic Reticulum in Pancreatic β-Cells," 2005, J Biol Chem, 280/47: 39609-39615, 7 pages.
Fonseca, S.G., et al., "Wolfram Syndrome 1 Gene Negatively Regulates ER Stress Signaling in Rodent and Human Cells," 2010, J Clinical Investigation, 2010, 120/3: 744-755, 12 pages.
Goll, D.E., et al., "The Calpain System," 2003, Physiol Rev, 3/3: 731-80, 71 pages.
Hara, T., "Calcium Efflux from the Endoplasmic Reticulum Leads to β-Cell Death," 2014, Endocrinology, 155/3:758-768, 11 pages.
Hershey, T., et al., "Early Brain Vulnerability in Wolfram Syndrome," 2012, PloS one, 7/7:e40604, 13 pages.
Hetz, C., et al., "Targeting the Unfolded Protein Response in Disease," 2013, Drug Discovery, 12/9: 703-719, 17 pages.
Hotamisligil, G.S., "Endoplasmic Reticulum Stress and Atherosclerosis," 2010, Nature Medicine, 16/4:396-399, 8 pages.
Hotamisligil, G.S., "Endoplasmic Reticulum Stress and the Inflammatory Basis of Metabolic Disease," 2010, Cell, 140/6:900-917, 32 pages.
Inan, S., et al., "The Cytoprotective Effects of Dantrolene: A Ryanodine Receptor Antagonist," 2010, Anesthesia, 111/6:1400-1410, 11 pages.
Inoue, H., et al., "A Gene Encoding a Transmembrane Protein is Mutated in Subjects with Diabetes Mellitus and Optic Atrophy (Wolfram Syndrome)," 1998, Nature Genetics, 20/2:143-148, 2 pages (Abstract Only).
Kanki, T., et al., "Mitochondrial Abnormalities Drive Cell Death in Wolfram Syndrome," 2009, Cell Res, 19/8:922-923, 3 pages.
Krause, T., et al., "Dantrolene—A Review of its Pharmacology, Therapeutic Use and New Developments," 2004, Anaesthesia, 59:364-374, 10 pages.
Liu, M.C., et al. "Extensive Degradation of Myelin Basic Protein Isoforms by Calpain Following Traumatic Brain Injury," 2006, J Neurochem, 98/3:700-712, 13 pages.
Luciani, D.S., et al., "Roles of IP3R and RyR Ca2+ Channels in Endoplasmic Reticulum Stress and β-Cell Death," 2009, Diabetes, 58:422-432, 11 pages.
Ma, L., et al., "Effect of Mechanism of Dantrolene on Skeletal Muscle of Rats with Severe Scald Injury," 2014, Zhonghua yi xue za zhi, 94/14:1087-1091, 5 pages (English Language Abstract Only).
Marshall, B.A., et al., "Phenotypic Characteristics of Early Wolfram Syndrome," 2013, Orphanet Journal of Rare Diseases, 8/1:64, 12 pages.
Mekahli, D., et al., "Endoplasmic-Reticulum Calcium Depletion and Disease," 2011, Cold Spring Harb Perspect Biol, 3:a004317, pp. 1-32, downloaded Aug. 27, 2014 from http://cshperspectives.cshlp.org/, 32 pages.
Muehlschlegel, S., et al., "Dantrolene: Mechanisms of Neuroprotection and Possible Clinical Applications in the Neurointensive Care Unit," 2009, Ceurocrit Care, 10/1:103-115, 19 pages.
Muralidharan, A.R., et al., "Virtual Screening Based on Pharmacophoric Features of Known Calpain Inhibitors to Identity Potent Inhibitors of Calpain," 2014, Med Chem Res, 23:2445-2455, 11 pages.
Nakagawa, T., et al., "Cross-Talk Between Two Cysteine Protease Families. Activation of Caspase-12 by Calpain in Apoptosis," 2000, J of Biol Chem, 150/4:887-894, 8 pages.
Ozcan, L., et al., "Role of Endoplasmic Reticulum Stress in Metabolic Disease and Other Disorders," 2012, Annu Rev Med, 63:316-328, 13 pages.
Riggs, A.C., et al., "Mice Conditionally Lacking the Wolfram Gene in Pancreatic Islet β Cells Exhibit Diabetes as a Result of Enhanced Endoplasmic Reticulum Stress and Apoptosis," 2005, Diabetologia, 48/11:2313-2321, 9 pages.
Ron, D., et al., "Signal Integration in the Endoplasmic Reticulum Unfolded Protein Response," 2007, Mol Cell Biol, 8/7: 519-529, 11 pages.
Saez, M.E., et al., "The Therapeutic Potential of the Calpain Family: New Aspects," 2006, Drug Discovery Today, 11(19/20):916-922, 7 pages.
Sandhu, M.S., et al., "Common Variants in WFS1 Confer Risk of Type 2 Diabetes," 2007, Nature genetics, 39/8:951-953, 7 pages.
Schiefer, I.T., et al., "Design, Synthesis, and Optimization of Novel Epoxide Incorporating Peptidomimetics as Selective Calpain Inhibitors," 2013, J Med Chem, 56/15:6054,6068, 15 pages.
Shang, L. et al., "β-Cell Dysfunction Due to Increased ER Stress in a Stem Cell Model of Worlfam Syndrome," 2014, Diabetes, 2014, Diabetes, 63:923-933, 11 pages.
Tabas, I., et al., "Integrating the Mechanisms of Apoptosis Induced by Endoplasmic Reticulum Stress," 2011, Nature Cell Biology, 13/3: 184-190, 17 pages.
Takahashi, K., et al., "Induction of Pluripotent Stem Cells from Mouse Embryonic and Adult Fibroblast Cultures ny Defined Factors," 2006, Cell, 126/4: 663-676, 14 pages.
Takei, D., et al., "WFS1 Protein Modulates the Free Ca(2+) Concentration in the Endoplasmic Reticulum," 2006, FEBS Lett, 580/24:5635-5640, 6 pages.
Tan, Y., et al., "Ubiquitous Calpains Promote Caspase-12 and JNK Activation During Endoplasmic Reticulum Stress-Induced Apoptosis," 2006, J of Biol Chem, 281/23:16016-16024, 9 pages.
Tan, Y. et al., "Ubiquitous Calpains Promote Both Apoptosis and Survival Signals in Response to Different Cell Death Stimuli," 2006, J of Biol Chem, 281/26:17689-17698, 10 pages.
Upadhya, G.A., et al., "Effect of Cold Preservation on Intreacellular Calcium Concentration and Calpain Activity in Rat Sinusoidal Endothelial Cells," 2003, Hepatology, 34:313-323, 11 pages.
Urano, F., "Wolfram Syndrome iPS Cells: The First Human Cell Model of Endoplasmic Reticulum Disease," 2014, Diabetes, 63:844-846, 3 pages.
Urano, F., "Diabetes: Targeting Endoplasmic Reticulum to Combat Juvenile Diabetes," 2014, Nat Rev Endocrinol, 10/3:129-130, 4 pages.
Wang, S., et al., "The Impact of the Unfolded Protein Response on Human Disease," 2012, J Cell Biol, 197/7:857-867, 11 pages.
Wei, H., et al., "Dantrolene is Cytoprotective in Two Models of Neuronal Cell Death," 1996, J Neurochem, 67/6:2390-2398, 2 pages (Abstract Only).
Wiley, S.E., et al., "Wolfram Syndrome Protein, Miner1, Regulates Sulphydryl Redox Status, the Unfolded Protein Response, and Ca2+ Homeostatis," 2013, EMBO Mol Med, 5:904-918, 15 pages.
Yusta, B., et al., "GLP-1 Receptor Activation Improves B Cell Function and Survival Following Induction of Endoplasmic Reticulum Stress," .2006,Cell Metab, 4/5:391-406, 16 pages.
Diapedia, "Wolfram Syndrome" 6 pages.
Callaghan, B.C., et al., "Diabetic Neuropathy: Clinical Manifestations and Current Treatments," Jun. 2012, Lancet Neurol, 11/6:521-534, 29 pages.
Huizinga, M.M., et al., "Painful Diabetic Neuropathy: A Management-Centered Review," 2007, Clinical Diabetes, 25/1:6-15, 10 pages.
Izenberg, A., et al., "Diabetic Neuropathies," 2015, Seminars in Neurology, Thieme Medical Publishers, Inc., New York, NY, 35:424-430, 7 pages.
NDA Label 17443/S-S-043/S-046/S-048/S-049, "Dantrium," Oct. 2011, Reference ID: 3100954, 9 pages.
NDA Label, "Lyrica (prebabalin)," Revised Jun. 2012, Reference ID: 3148643, 49 pages.
NDA Label, "Neurontin (gabapentin)," Revised Oct. 2017, Reference ID: 4168942, 37 pages.
"Treatment of Painful Diabetic Neuropathy," AAN Summary of Evidence-Based Guideline for Clinicians, 2011 American Academy of Neurology, 2 pages.
Urano, F., "Wolfram Syndrome: Diagnosis, Management, and Treatment," 2016, Curr Diab Rep, 16:6, 8 pages.
"Wolfram syndrome," Genetic and Rare Diseases Information Center, NCATS, National Institutes of Health, https://rarediseases.info.nih.gov/diseases/7898/wolfram-syndrome, accessed Jan. 31, 2019.

* cited by examiner

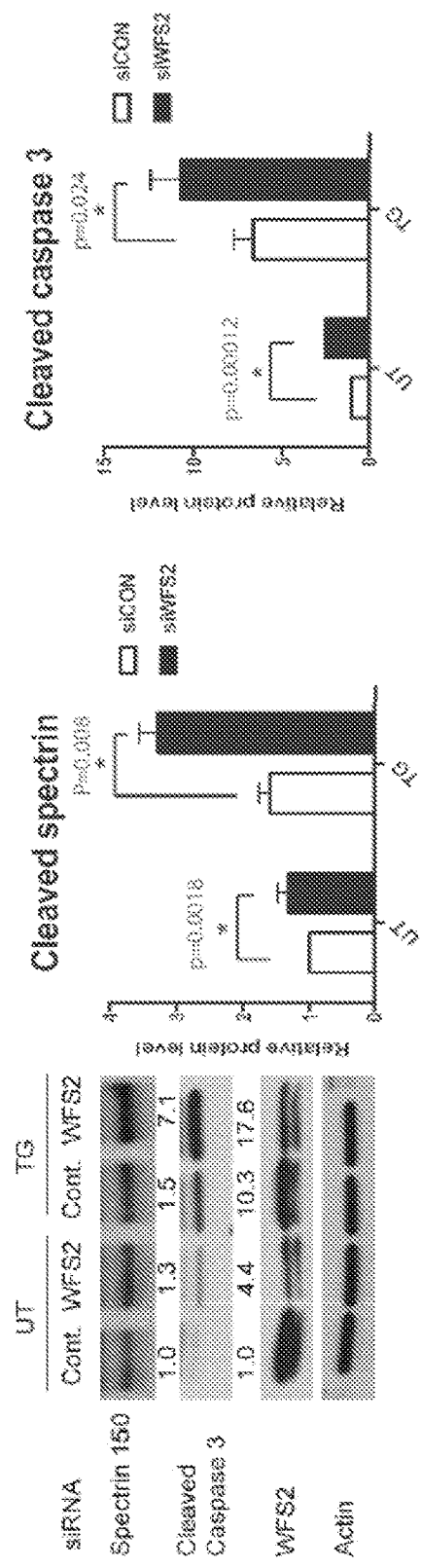
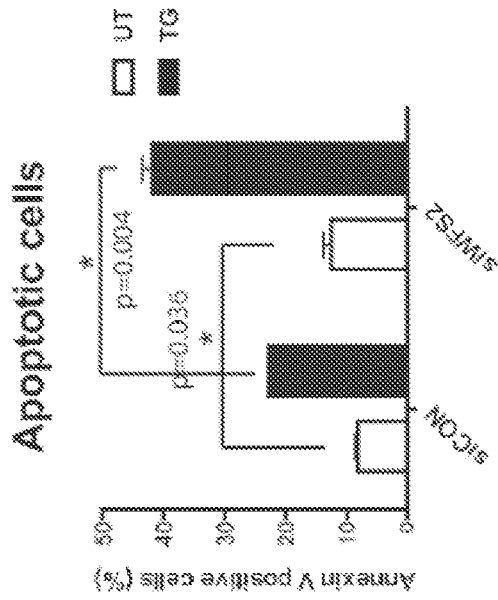
Figure 4A
Figure 4B

1  Calbindin (-1.31)  or  SNAP-25    increased/decreased

2  Myelin basic protein (-2.49)

3  Myelin basic protein (-2.51)

4  Cytochrome c oxidase subunit6B1 (>1.5)
5  GFAP (1.22)
6  FKBP4 (1.32)
7  Syntaxin-binding protein 1 (1.38)
8  Stathmin (-2.51)
9  Cytochrome C1 (-1.48)
10 Phosphatidylethanolamine-binding protein 1 (1.7)
11 Purkinje cell protein 4 (1.33)
12 Hemoglobin subunit aplha (-1.81)

TREATMENT FOR WOLFRAM SYNDROME AND OTHER ENDOPLASMIC RETICULUM STRESS DISORDERS

REFERENCE TO RELATED APPLICATIONS

This application is the 371 National Stage Application based on International Application Serial No. PCT/US2015/060598, filed Nov. 13, 2015, and claims the benefit of U.S. Provisional Application Ser. No. 62/079,480, filed Nov. 13, 2014, the contents of which are incorporated by reference herein.

GOVERNMENT LICENSE RIGHTS

This invention was made with Government support under grant R01 DK067493 awarded by the U.S. National Institutes of Health. The Government has certain rights in the invention.

FIELD OF THE INVENTION

The present invention generally relates to a method of treating or preventing an endoplasmic reticulum stress disorder in subjects, including a method of treating or preventing Wolfram syndrome.

BACKGROUND OF THE INVENTION

Wolfram syndrome is a rare autosomal recessive disorder characterized by diabetes insipidus, diabetes mellitus, optic atrophy, and deafness (also known as DIDMOAD). Insulin dependent diabetes usually occurs as the initial manifestation during the first decade of life, while the diagnosis of Wolfram syndrome is invariably later with onset of the other features in the second and ensuing decades. Two causative genes for this genetic disorder have been identified and are named WFS1 and WFS2. It has been shown that multiple mutations in the WFS1 gene, as well as a specific mutation in the WFS2 gene, lead to 13 cell death and neurodegeneration through endoplasmic reticulum (ER) and mitochondrial dysfunction. WFS1 gene variants are also associated with a risk of type 2 diabetes. Moreover, a specific WFS1 variant can cause autosomal dominant diabetes.

Wolfram syndrome is caused by stress in the ER, a cell component involved in many vital functions of the eyes, brain, and pancreas. The ER is a membrane-bound organelle that is crucial for the folding and maturation of proteins, lipid biosynthesis, and homeostasis of intracellular $Ca^{2+}$ and reduction-oxidation (redox) potential. Protein folding and modification in the ER is highly sensitive to disturbances of ER homeostasis, including altered glycosylation, ER $Ca^{2+}$ depletion, increased mRNA translation, oxidative stress, energy deprivation, metabolic challenge, and inflammatory stimuli. The accumulation of unfolded and misfolded proteins in the ER lumen, termed ER stress, activates intracellular signaling pathways to resolve the protein folding defect. This unfolded protein response (UPR) increases the capacity of ER protein folding and modification, reduces global protein synthesis, and activates ER-associated protein degradation (ERAD). If ER stress is too severe or chronic, or the UPR is compromised and not able to restore the protein folding homeostasis, numerous apoptotic signaling pathways are activated.

Despite the underlying importance of ER malfunction in ER stress disorders such as Wolfram syndrome and the identification of WFS1 and WFS2 genes, a molecular mechanism linking the ER to death of neurons and 13 cells has not been elucidated. Thus, to date there are no known treatments for Wolfram Syndrome and other ER stress disorders.

SUMMARY OF THE INVENTION

Briefly, various aspects of the present invention are directed to methods of treating or preventing an ER stress disorder in a subject in need thereof. The methods comprise administering to the subject a therapeutically effective amount of a ryanodine receptor (RYR) inhibitor.

In various aspects, the present invention is also directed to methods of treating or preventing Wolfram Syndrome in a subject in need thereof comprising administering to the subject a therapeutically effective amount of a ryanodine receptor inhibitor.

In further aspects, the present invention is directed to methods of treating or preventing clinical symptoms of an ER stress disorder, such as Wolfram Syndrome, in a subject in need thereof comprising administering to the subject a therapeutically effective amount of a ryanodine receptor inhibitor.

Other objects and features will be in part apparent and in part pointed out hereinafter.

BRIEF DESCRIPTION OF THE DRAWINGS

FIG. 4A is a depiction of an immunoblot of NSC34 cells transfected with control scramble siRNA or siRNA directed against WFS2 and a graph illustrating a change in expression levels of cleaved spectrin and caspase 3.

FIG. 4B is a graph apoptosis of NSC34 cells transfected with scrambled siRNA or siRNA directed against WFS2 untreated or treated with thapsigargin.

Figure 10A:
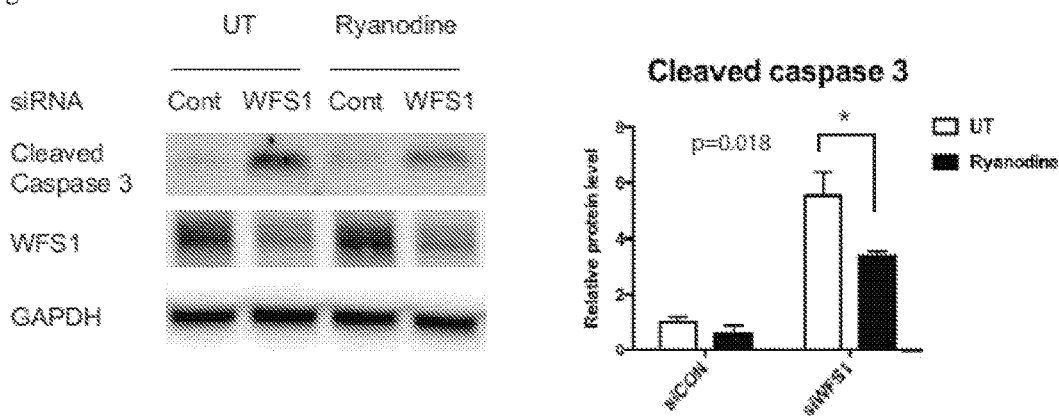

FIG. 10A is a depiction of an immunoblot of INS-1 832/13 cells transfected with scrambled siRNA or siRNA directed towards WFS1 and untreated or treated with ryanodine and a graph illustrating a change in expression level of cleaved caspase 3.

Figure 10B:
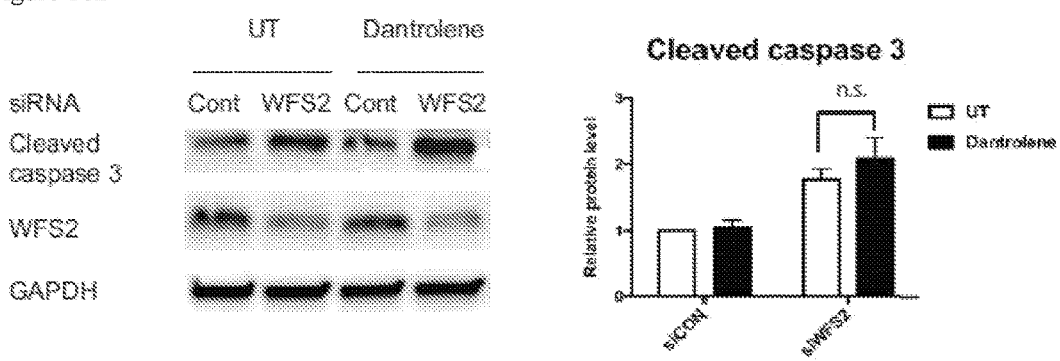

FIG. 10B is a depiction of an immunoblot of INS-1 832/13 cells transfected with scrambled siRNA or siRNA directed towards WFS1 and untreated or treated with dantrolene and a graph illustrating a change in expression level of cleaved caspase 3.

Figure 10C:
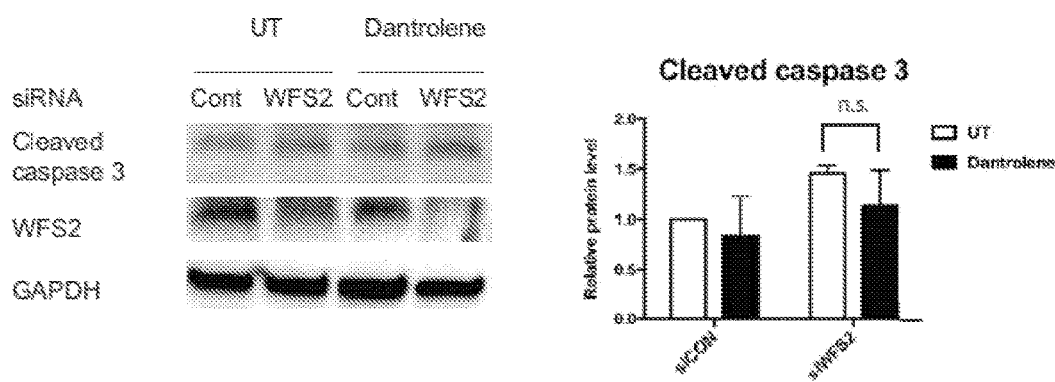

FIG. 10C is a depiction of an immunoblot of INS-1 832/13 cells transfected with scrambled siRNA or siRNA directed towards WFS1 and untreated or treated with dantrolene and a graph illustrating a change in expression level of cleaved caspase 3.

Figure 10D:
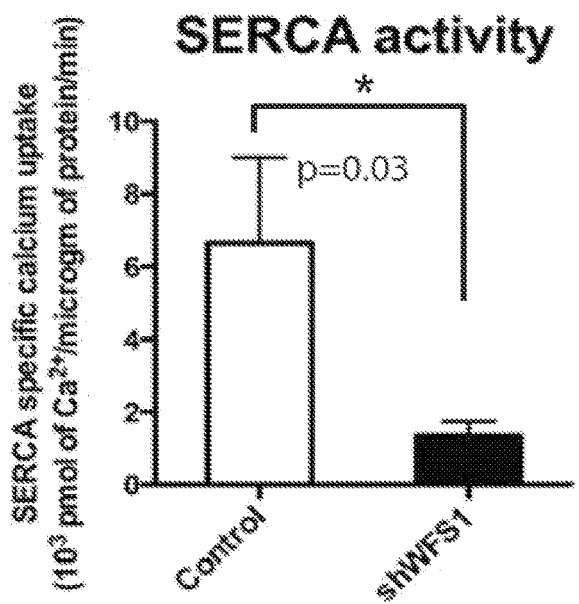

FIG. 10D is a graph of SERCA activity of HEK293T cells expressing a scrambled shRNA or a shRNA directed against WFS1.

Figure 10E:
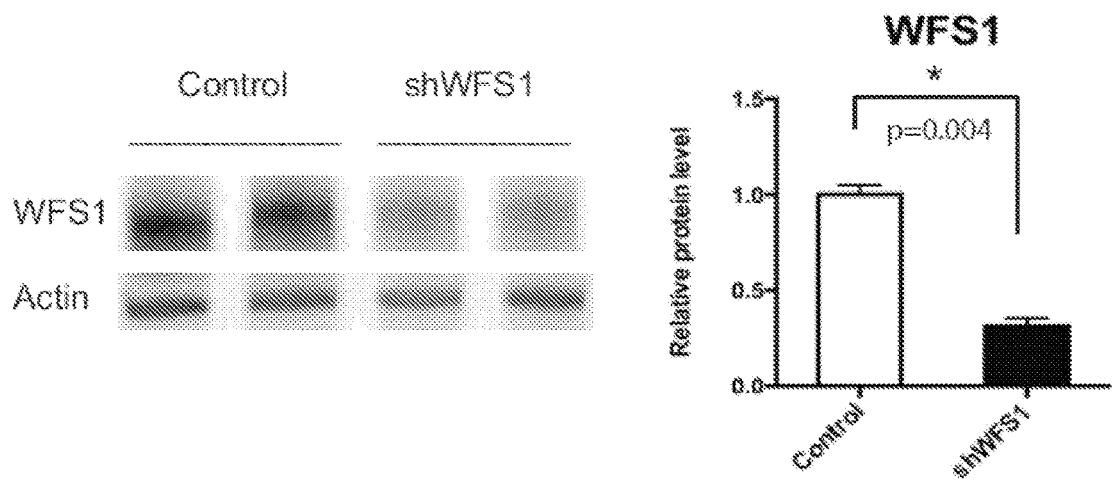

FIG. 10E is a depiction of an immunoblot of HEK293T cells stably expressing scrambled shRNA or a shRNA directed against WFS1 and a graph illustrating a change in expression levels of WFS1.

Figure 10F:
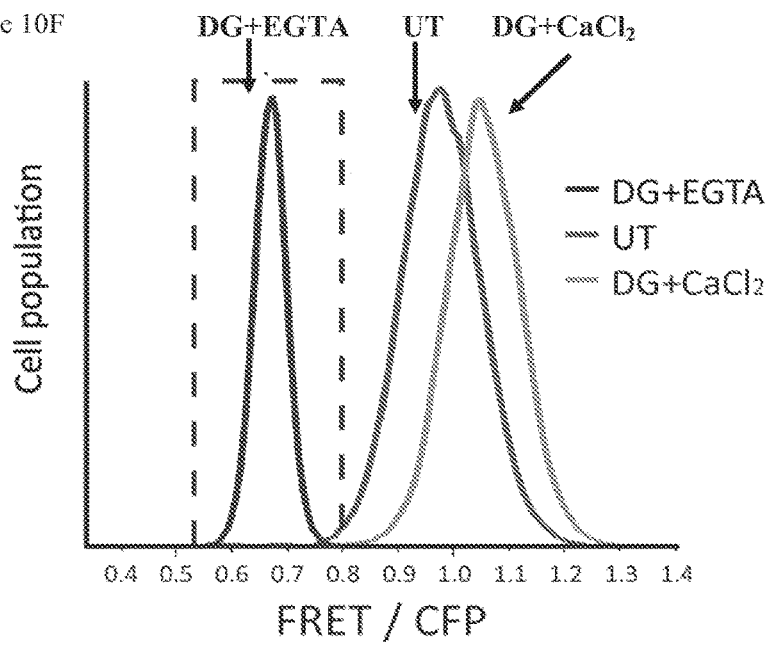

FIG. 10F is a graph of FACS analysis of INS-1 832/13 cells expressing D1ER untreated or treated with digitonin, EGTA, or digitonin and $CaCl_2$.

Figure 10G:
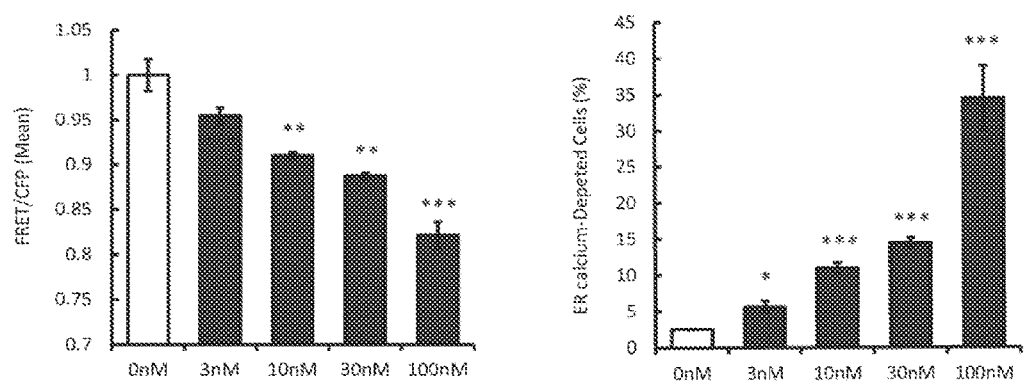

FIG. 10G is a graph of FACS analysis of INS-1 832/13 cells expressing D1ER treated with various concentrations of thapsigargin.

Figure 11A:
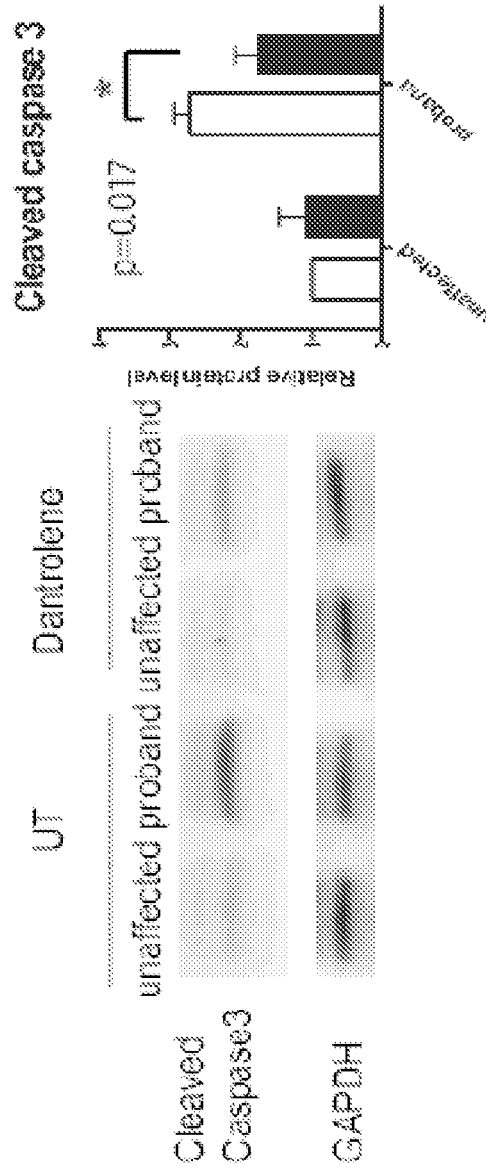

FIG. 11A is a depiction of an immunoblot of neural progenitor cells pretreated with or without dantrolene, then treated with thapsigargin and a graph illustrating changes in expression level of cleaved caspase 3.

Figure 12A:
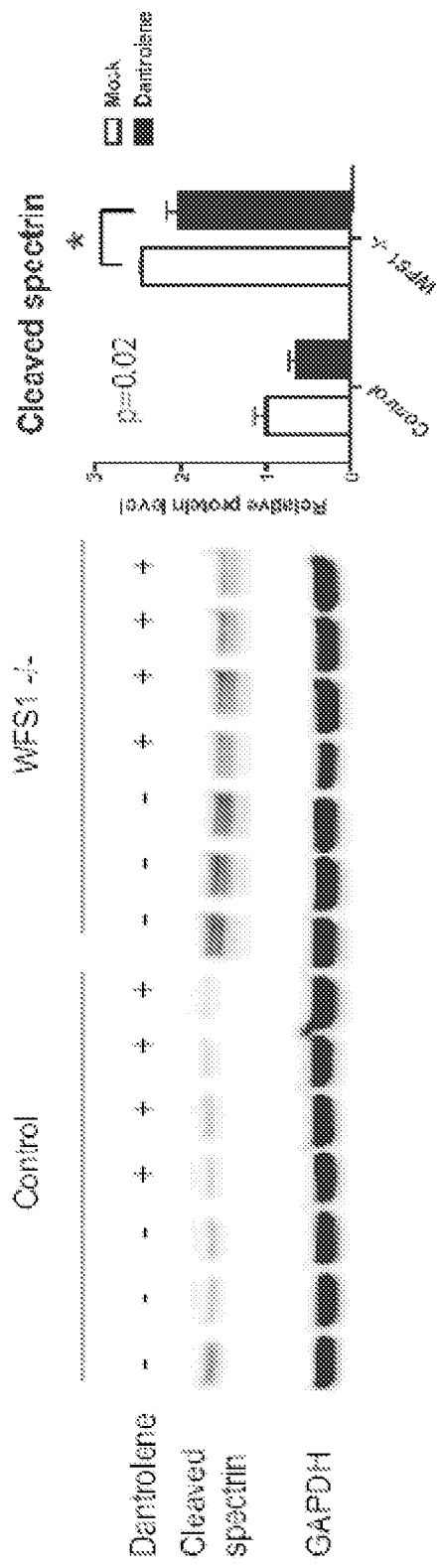

FIG. 12A is a depiction of an immunoblot of brain lysates from WFS1 brain specific knockout mice untreated or treated with dantrolene and a graph illustrating a change in expression levels of cleaved spectrin.

Figure 13A:
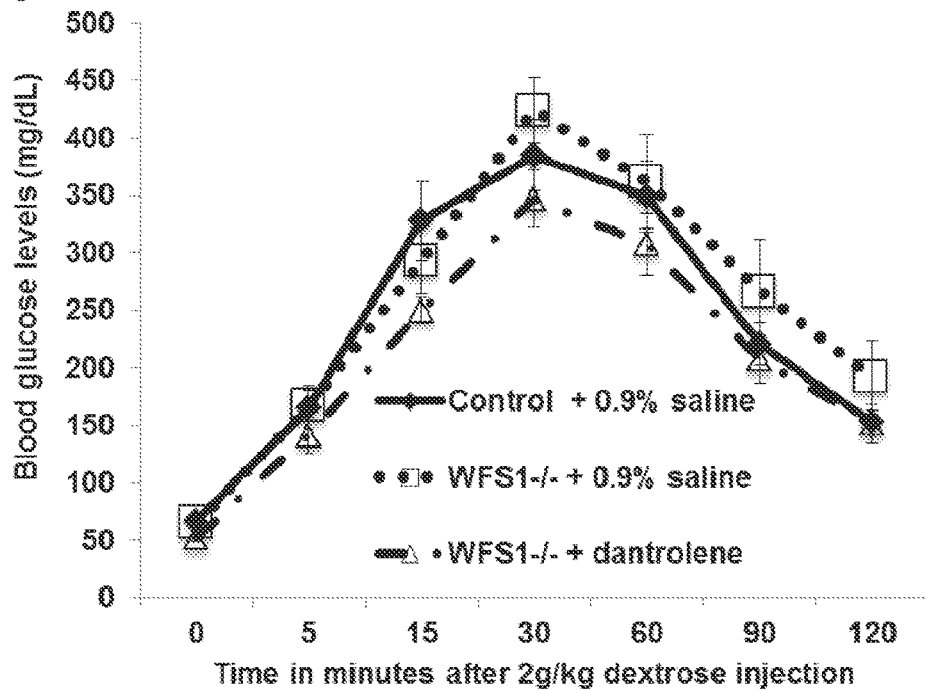

FIG. 13A is a graph illustrating a change in blood glucose level in Wolfram syndrome mice untreated or treated with dantrolene after injection of a dextrose solution at week 13.

Figure 13B:
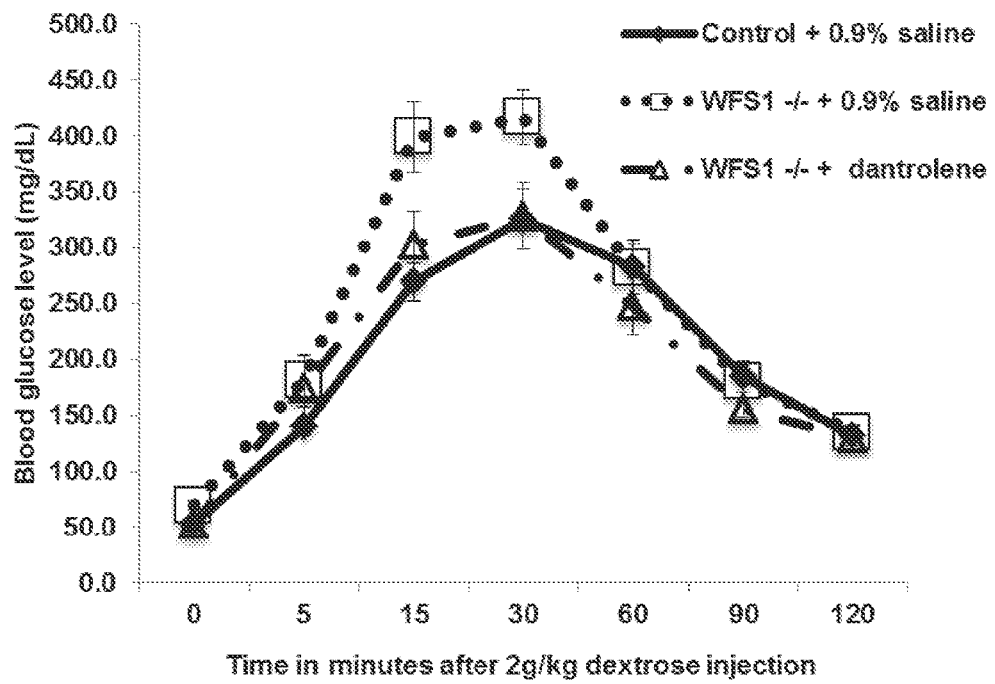

FIG. 13B is a graph illustrating a change in blood glucose level in Wolfram syndrome mice untreated or treated with dantrolene after injection of a dextrose solution at week 18.

Figure 13C:
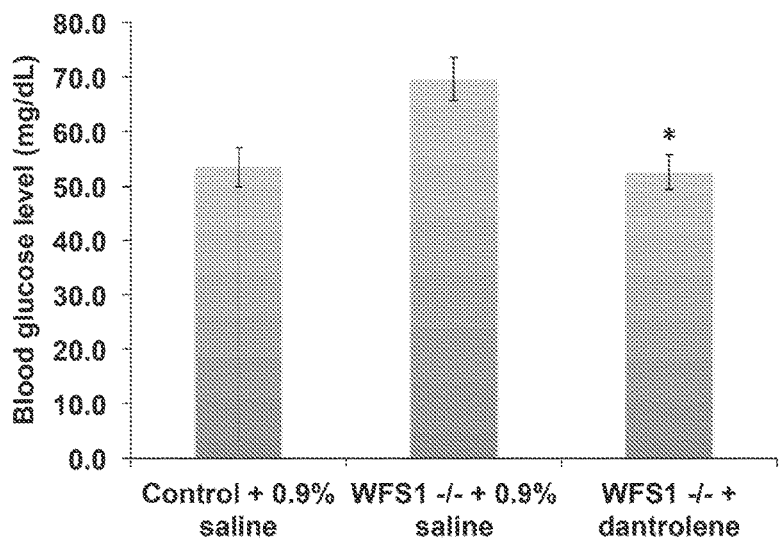

FIG. 13C is a graph illustrating a change in overall blood glucose level in Wolfram syndrome mice untreated or treated with dantrolene.

Figure 13D:
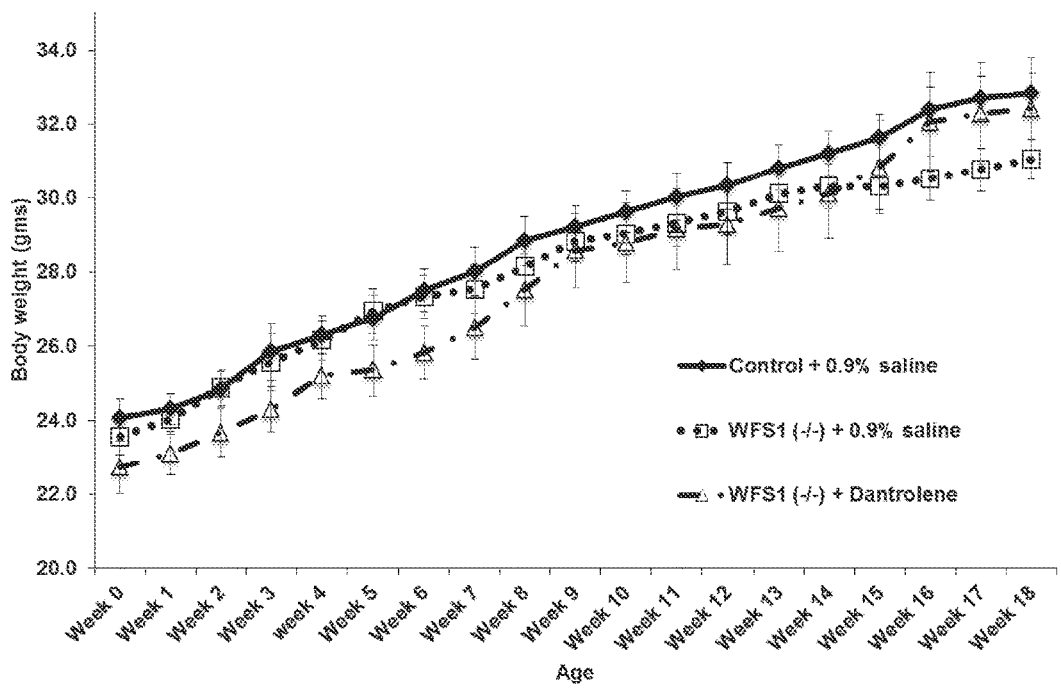

FIG. 13D is a graph illustrating a change in body weight in Wolfram syndrome mice untreated or treated with dantrolene.

Figure 14A:
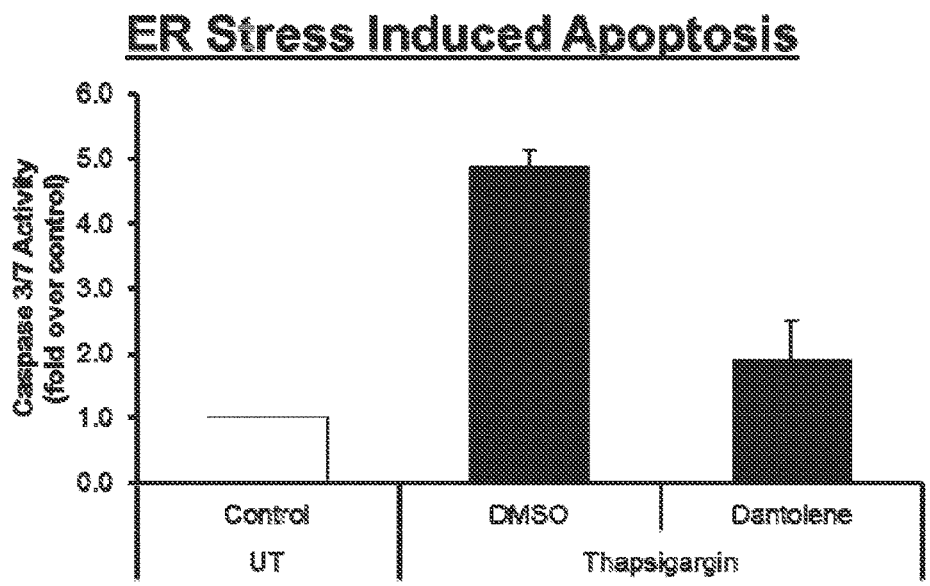

FIG. 14A is a graph illustrating cell death in INS1E cells treated with dantrolene and challenged with thapsigargin.

Figure 14B:
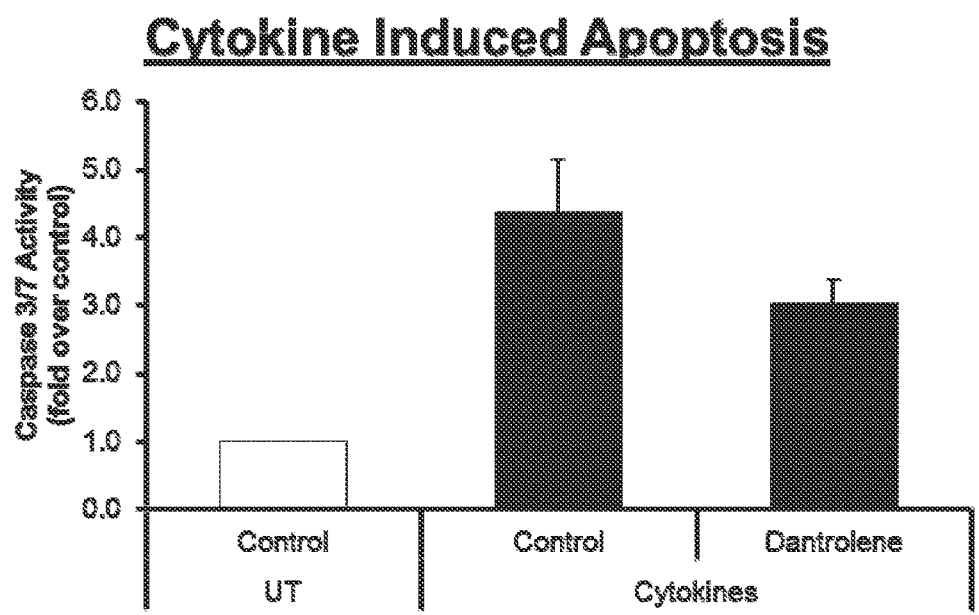

FIG. 14B is a graph illustrating cell death in INS1E cells treated with dantrolene and challenged with cytokines.

DETAILED DESCRIPTION

In general, the present invention is directed to the use of a ryanodine receptor inhibitor such as dantrolene to prevent or delay the progression of disorders associated with ER dysfunction. Surprisingly, it has been discovered that calpain-2 protease provides a link between the ER and death of neurons and β cells in Wolfram syndrome. This discovery of the underlying molecular mechanisms provides strategies to treat various disorders driven by prolonged ER stress. Evidence indicates that ER dysfunction triggers a range of human chronic diseases, including Type 1 and Type 2 diabetes, atherosclerosis, inflammatory bowel disease, retinitis pigmentosa, and neurodegenerative diseases, such as amyotrophic lateral sclerosis (ALS), Parkinson's disease, and Alzheimer's disease. However, currently there is no effective therapy targeting the ER for such diseases due to the lack of clear understanding of the ER's contribution to the pathogenesis of such diseases.

Figure 1:
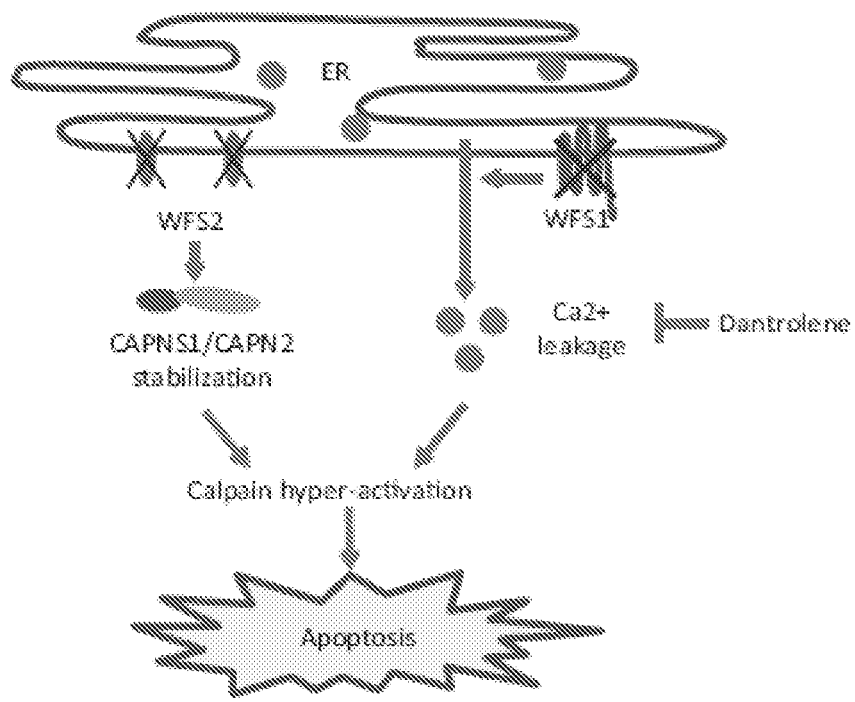
FIG. 1 is a depiction of the pathogenesis of Wolfram syndrome.

Although Wolfram syndrome is a rare disease and is currently neglected from mainstay drug discovery efforts, the homogeneity of the subject population and disease mechanism has enabled identification of an important drug target, a calcium-dependent protease, calpain-2. Applicants have discovered that calpain-2 hyperactivation is seen in both cell models and mouse models of Wolfram syndrome. Without being bound by theory, FIG. 1 presents a proposed explanation for the pathogenesis of Wolfram syndrome and the target a ryanodine receptor inhibitor such as dantrolene.

Figure 2:
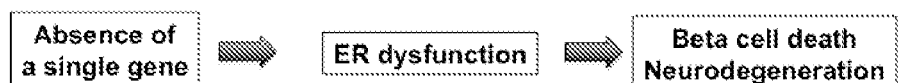
FIG. 2 is a scheme illustrating Wolfram syndrome as a prototype of human endoplasmic reticulum function.
Figure 2:
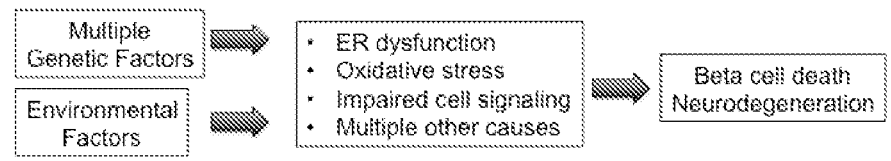

Despite its rarity, Wolfram syndrome represents an exceptional human disease model currently available to identify drugs and biomarkers associated with ER health. Because it is challenging to determine the exact effects of ER dysfunction on the fate of affected cells in common diseases with polygenic and multifactorial etiologies, applicants sought to define the role of ER dysfunction in mechanistically homogenous patient populations such as Wolfram syndrome. Accordingly, applicants have discovered that small molecule compounds capable of preventing calpain-2 hyperactivation or maintaining ER calcium homeostasis under ER stress conditions can be used to treat subjects (e.g., humans) with both Wolfram syndrome and common diseases in which the ER is involved. A depiction of human endoplasmic reticulum dysfunction, including Wolfram syndrome is shown in FIG. 2.

Accordingly, various aspects of the present invention are directed to a method of treating or preventing ER stress disorders such as Wolfram syndrome in subjects (e.g., humans) in need thereof comprising administering to the subjects an effective amount of a compound that is a ryanodine receptor inhibitor in a pharmaceutically acceptable carrier. In further aspects, the present invention is directed to methods of treating or preventing clinical symptoms of an ER stress disorder such as β cell and neuronal cell death in a subject in need thereof comprising administering to the subject a therapeutically effective amount of a ryanodine receptor inhibitor.

One ryanodine receptor inhibitor useful in the methods of the present invention includes dantrolene. Further in accordance with the present invention, it has been discovered that dantrolene can prevent ER stress-mediated cell death associated with Wolfram syndrome. Thus, dantrolene and other drugs that can regulate ER calcium homeostasis can be used to delay the progression of Wolfram syndrome and other ER stress disorders including Type 1 and Type 2 diabetes, atherosclerosis, inflammatory bowel disease, retinitis pigmentosa, and neurodegenerative diseases, such as amyotrophic lateral sclerosis (ALS), Parkinson's disease, and Alzheimer's disease.

"Dantrolene" as used herein refers to 1-[[5-(4-nitrophenyl)-2-furyl]methylideneamino]imidazolidine-2,4-dione or a pharmaceutically acceptable salt or hydrate thereof. One form of dantrolene is the monosodium salt of dantrolene or a hydrate thereof. Dantrolene sodium, a ryanodine receptor inhibitor, has been in clinical use since the 1980's for treating muscle dysfunction associated with malignant hyperthermia (MH). More recently, it has been used for the management of neuroleptic malignant syndrome, spasticity, heat stroke, and methamphetamine intoxication. Dantrolene is thought to depress excitation-contraction coupling in skeletal muscle by inhibiting the release of calcium ($Ca^{2+}$) from the sarcoplasmic reticulum, (smooth ER found in muscle cells). The molecular structure of dantrolene sodium is shown below.

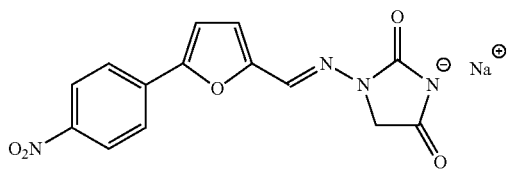 [SMILES: O=C1CN(/N=C/c2ccc(-c3ccc([N+](=O)[O-])cc3)o2)C(=O)[N-]1 ; [Na+]]

Dantrolene is highly lipophilic and poorly soluble in water. A more water soluble analog of dantrolene called azumolene is under development for similar indications as dantrolene. Azumolene, has a bromine group instead of the p-nitro group found in dantrolene, and is thirty times more water soluble. "Azumolene" as used herein refers to 1-[[5-(4-bromophenyl)-2-furyl]methylideneamino]imidazolidine-2,4-dione or a pharmaceutically acceptable salt or hydrate thereof. Thus, another ryanodine receptor inhibitor useful in the methods of the present invention includes azumolene.

The mechanism by which a ryanodine receptor inhibitor such as dantrolene prevents cell death associated Wolfram syndrome is not entirely understood. However, without being bound by theory, applicants believe that loss of function of WFS1 increases cytoplasmic calcium levels leading to activation of the calcium-dependent cysteine protease calpain-2. Calpains are involved in a variety of calcium regulated cellular processes, such as signal transduction, cell proliferation and differentiation, and apoptosis. Applicants also believe that WFS2, the other causative gene for Wolfram syndrome, is a suppressor of calpain-2 mediated cell death. Thus, loss of function of WSF2 results in increased apoptosis of β-cells in Wolfram syndrome subjects.

By exploiting induced pluripotent stem cells (iPSCs) derived from the skin cells of subjects with Wolfram syndrome, applicants have discovered drugs that block activation of this enzyme and cell death. In this approach, applicants have targeted the pathway to calpain activation instead of focusing on calpain specific inhibitors.

In accordance with the present invention, a pharmaceutical composition comprising a ryanodine receptor inhibitor such as dantrolene is administered to the subject in need thereof. The pharmaceutical composition can be administered to a subject to achieve a desired therapeutic effect, e.g., inhibiting calpain-2 protease activity. The pharmaceutical composition used in the practice of the present invention may suitably comprise, consist of, or consist essentially of one or more ryanodine receptor inhibitors and the pharmaceutically acceptable carrier.

The composition can be administered alone or in combination with at least one other active agent that modulates the transport of calcium ($Ca^{2+}$) ions to and/or from the endoplasmic reticulum in a cell. Intracellular calcium level is precisely regulated by cooperative action of a series of calcium permeable channels, calcium pumps and calcium exchangers in the plasma membrane and endoplasmic reticulum. For instance, calcium is dynamically stored in the endoplasmic reticulum (ER), which is able to accumulate very high $Ca^{2+}$ levels due to activity of sarco/endoplasmic reticulum calcium adenosine triphosphatase (SERCA) pumps. Release of $Ca^{2+}$ from the endoplasmatic reticulum is controlled by two types of $Ca^{2+}$ release channels, namely ryanodine receptors and inositol triphosphate receptors (IP3Rs). The second active agent can be, for example, an inhibitor of an inositol 1,4,5-triphosphate receptor (IP3R), such as rapamycin. Further, the second active agent can be a compound that enhances SERCA activation, such as pioglitazone.

The term "combination" designates a treatment wherein at least two or more drugs are co-administered to a subject to cause a biological effect. In a combined therapy according to this invention, the at least two drugs may be administered together or separately, at the same time or sequentially. Also, the at least two drugs may be administered through different routes and protocols. As a result, although they may be formulated together, the drugs of a combination may also be formulated separately.

In addition to the active ingredients (e.g., the ryanodine receptor inhibitor), the pharmaceutical composition can contain suitable pharmaceutically acceptable carriers comprising excipients and auxiliaries that facilitate processing of the active compounds into preparations which can be used pharmaceutically. The pharmaceutical composition can be administered by a routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. A pharmaceutical composition for oral administration can be formulated using pharmaceutically acceptable carriers known in the art in dosages suitable for oral administration. Such carriers enable the pharmaceutical compositions to be formulated as tablets, pills, dragees, capsules, liquids, gels, syrups, slurries, suspensions, and the like, for ingestion by the subject. In certain embodiments, the composition is formulated for parenteral administration. Further details on techniques for formulation and administration can be found in the latest edition of REMINGTON'S PHARMACEUTICAL SCIENCES (Mack Publishing Co., Easton, Pa., which is incorporated herein by reference). After pharmaceutical compositions have been prepared, they can be placed in an appropriate container and labeled for treatment of an indicated condition. Such labeling would include amount, frequency, and method of administration.

As used herein, the term "pharmaceutically acceptable carrier" means a non-toxic, inert solid, semi-solid or liquid filler, diluent, encapsulating material, or formulation auxiliary of any type. Some examples of materials which can serve as pharmaceutically acceptable carriers are sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil; and soybean oil; glycols such as propylene glycol; esters such as ethyl oleate and ethyl laurate; agar; detergents such as TWEEN 80; buffering agents such as magnesium hydroxide and aluminum hydroxide; alginic acid; pyrogen-free water; isotonic saline; Ringer's solution; ethyl alcohol; artificial cerebral spinal fluid (CSF), and phosphate buffer solutions, as well as other non-toxic compatible lubricants such as sodium lauryl sulfate and magnesium stearate, as well as coloring agents, releasing agents, coating agents, sweetening, flavoring, and perfuming agents, preservatives and antioxidants can also be present in the composition, according to the judgment of the formulator based on the desired route of administration.

The determination of a therapeutically effective dose for any one or more of the ryanodine receptor inhibitors described herein is within the capability of those skilled in the art. A therapeutically effective dose refers to that amount of active ingredient which provides the desired result. The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Typically, the normal dosage amount of the ryanodine receptor inhibitor can vary from about 0.05 to about 100 mg per kg body weight depending upon the route of administration. Guidance as to particular dosages and methods of delivery is provided in the literature and generally available to practitioners in the art. It will generally be administered so that a daily oral dose in the range, for example, from about 0.1 mg to about 75 mg, from about 0.5 mg to about 50 mg, or from about 1 mg to about 25 mg per kg body weight is given. The active ingredient can be administered in a single dose per day, or alternatively, in divided does (e.g., twice per day, three time a day, four times a day, etc.). In general, lower doses can be administered when a parenteral route is employed. Thus, for example, for intravenous administration, a dose in the range, for example, from about 0.05 mg to about 30 mg, from about 0.1 mg to about 25 mg, or from about 0.1 mg to about 20 mg per kg body weight can be used.

In one aspect of the invention, the ryanodine receptor inhibitor comprises dantrolene sodium. Dantrolene sodium for injection is commercially available as DANTRIUM INTRAVENOUS (JHP Pharmaceuticals, Parsippany, N.J.). It is a sterile, non-pyrogenic, lyophilized formulation supplied in 70 mL vials containing 20 mg dantrolene sodium, 3000 mg mannitol, and sufficient sodium hydroxide to yield pH of approximately 9.5 when reconstituted with 60 mL sterile water for injection USP.

Dantrolene sodium capsules are commercially as DANTRIUM (JHP Pharmaceuticals, Parsippany, N.J.). DANTRIUM is supplied in capsules of 25 mg, 50 mg, and 100 mg. Each capsule contains edible black ink, FD&C Yellow No. 6, gelatin, lactose, magnesium stearate, starch, synthetic iron oxide red, synthetic iron oxide yellow, talc, and titanium dioxide.

EXAMPLES

The following non-limiting examples are provided to further illustrate the present invention.

Example 1: Materials and Methods

Thapsigargin, tunicamycin, calpeptin and cycloheximide were obtained from Sigma-Aldrich (St. Louis, Mo.). Growth media RPMI-1640 and Dulbecco's Modified Eagle Medium (DMEM) were obtained from Invitrogen (Carlsbad, Calif.). Neural induction media and neural proliferation media were obtained from STEMCELL Technologies (Vancouver, B.C., CA). MitoProbe DilC1 (5) mitochondrial membrane potential assay kit, Annexin V Alexa Flour488 conjugate, Fluo-4 and Fura-2 calcium indicators were obtained from INVITROGEN (Carlsbad, Calif.). Caspase-glo 3/7 protease assay kit and calpain-glo protease assay kit were obtained from Promega (Madison, Wis.). Mito Stress test kit was obtained from Seahorse Bioscience (North Billerica, Mass.). Anti-WFS2 antibody and anti-WFS1 antibody were obtained from Proteintech (Chicago, Ill.). Anti-caspase-3 and anti-CAPN2 antibodies were obtained from Cell Signaling Technology, Inc. (Danvers, Mass.). Anti-CAPNS1 and anti-alpha II spectrin antibody were obtained from EMD Millipore (Billerica, Mass.). Anti-actin antibody was obtained from Sigma-Aldrich (St. Louis, Mo.). Anti-myelin basic protein antibody was obtained from Santa Cruz Biotechnology (Santa Cruz, Calif.). Anti-calpain-2 antibody, which detects both CAPN2 and CAPNS1, was raised in rabbits against bacterially expressed rat calpain-2.

Plasmids and siRNA pCMV-SPORT6-WFS2 expression plasmid was purchased from Open Biosystems (GE Healthcare, Pittsburgh, Pa.). pDsRed2-ER vector was purchased from Clonetech Laboratories, Inc. (Mountain View, Calif.). FLAG tagged WFS2 plasmids were constructed by inserting FLAG sequences into the N- and C-termini of the expression plasmid. GST-WFS2 plasmid was generated by inserting WFS2 sequence into pEBG mammalian expression plasmid. A CAPN2 expression plasmid was generated in plenty-cmv-pro plasmid provided by E. Campeau (Campeau et al., 2009). LIPOFECTAMINE 2000 (INVITROGEN, Carlsbad, Calif.) was used to transfect small interfering RNA (siRNA) directed against WFS2 and CAPN2 into cells. siRNAs were designed and synthesized at QIAGEN (Valencia, Calif.) as follows: mouse WFS2 with the sequence of SEQ ID NO: 1 (CAACAGAAGGAUAGCUUG), human WFS2 with the sequence of SEQ ID NO: 2 (CGAAAGUAGUGAAUGAAA), human CAPN2 with the sequence of SEQ ID NO: 3 (CCGAGGAGGUUGAAAGUA), and rat WFS1 with the sequence of SEQ ID NO: 4 (GUUUGACCGCUACAAGUUU). Cells were incubated in media overnight after siRNA transfection, and then additional treatments were performed, including ER stress induction.

Cell Culture

Neuro2a, NSC34, HEK293T MEFs, and COS7 cells were cultured in DMEM containing 10% FBS and penicillin and streptomycin (ThermoFisher Scientific, Waltham, Mass.). MING 3 cells were grown in DMEM containing 15% FBS and penicillin and streptomycin. Subject primary lymphoblasts and INS-1 832/13 cells were cultured in RPMI containing 10% FBS before measurement. Neural progenitor cells were maintained in STEMDIFF Neural Progenitor Medium from STEMCELL Technologies (Vancouver, BC, Canada).

iPS Cell and Neural Progenitor Cell Generation

To generate iPS cells, fibroblasts were obtained from non-affected controls and subjects with Wolfram syndrome. Integration-free iPS cells were generated via Sendai viral delivery of the four reprogramming factors, Oct4, Sox2, Klf4, and c-Myc using Life Technologies' (ThermoFisher Scientific, Waltham, Mass.) CYTOTUNE reagents and protocols. All WFS- and control-iPSCs showed silencing of the four transgenes, exhibited characteristic human embryonic stem cell morphology, expressed pluripotency markers including ALP, NANOG, SOX2, SSEA4, TRA-1, and had a normal karyotype. To generate neural progenitor cells, iPSCs were counted and plated ~50,000 per well in a 96-well plate to form uniform embryoid bodies. After 5 days, embryoid bodies were suspended in neural induction media and replated as adherent cultures. Fresh media was applied every day for 7 days. Neural rosettes formed in these cultures were selected and plated. Plated rosettes were fed with neural induction media every day for 4-7 days to obtain neural progenitor cells.

MALDI-TOF Mass Spectrometry

HEK293 cells were transfected with GST-WFS2 plasmid and empty GST plasmid. Cell lysates were collected and immunoprecipitated with glutathione beads in lysis buffer (150 mM NaCl, 0.5% TritonX-100, 50 mM HEPES, 1 mM EDTA, 1 mM DTT, pH7.5). The precipitated proteins from both samples were resolved by SDS-PAGE and stained with Coomassie blue staining. The distinct bands that only appear in GST-WFS2 lane but not GST lane were analyzed by MALDI-TOF tandem mass spectrometry on a Shimadzu Axima TOF2 mass spectrometry at University of Massachusetts Medical School Proteomics and mass spectrometry facility.

Immunostaining

Cells were fixed in 4% paraformaldehyde for 30 minutes at room temperature and then permeabilized with 0.1% TRITON X-100 for 2 minutes. The fixed cells were washed with phosphate buffered saline with TWEEN (PBS/TWEEN 20) 0.1%, blocked with Image-It FX signal enhancer (IN-VITROGEN, Carlsbad, Calif.) for 1 hour, and incubated in primary antibody overnight at 4° C. The cells were washed three times in PBS/TWEEN 0.1% and incubated with secondary antibody for 1 hour at room temperature. Images were obtained with a Zeiss (Oberkochen, Germany) LSM 5 PASCALconfocal microscope with LSM Image software.

FACS Analysis

Flow cytometry analyses (FACS) were performed with LSRII Flow Cytometer (BD Biosciences, San Jose, Calif.) at the FACS core facility of Washington University School of Medicine Neural progenitor cells or NSC34 cells were plated in 24-well plates. After staining with Annexin V, cells were washed and resuspended in PBS. Cells were run using standard protocols, specifically Annexin V positive cell (i.e., apoptotic cells). The results were analyzed by FlowJo ver.7.6.3 (Ashland, Oreg.).

Quantitative Real-Time PCR (qrt-PCR)

Total RNA was extracted by RNeasy kits (Qiagen, Waltham, Mass.). Reverse transcriptase PCR was performed using high capacity reverse transcription kit and quantitative PCR (q-PCR) was demonstrated with Applied Biosystems ViiA7 (ThermoFisher Scientific, Waltham, Mass.) using SYBR green dye.

2-Dimensional Gel Electrophoresis

Proteins were extracted from cerebellums from WFS1 knockout and control mice. Equal amount of protein extract from paired samples were labeled by CyDye DIGE fluors, and the spectrally resolvable dyes enabled simultaneous co-separation and analysis of samples on a single multiplexed gel. These paired samples were simultaneously separated on a single 2D gel, using isoelectric focusing (IEF) in the first dimension and sodium dodecyl sulfate polyacrylamide gel electrophoresis (SDS-PAGE) in the second dimension. After electrophoresis, the gel was scanned using a Typhoon image scanner (GE Healthcare Life Sciences, Pittsburgh, Pa.). Each scan revealed one of the CyDye signals (Cy3 and Cy5). ImageQuant software V. 8 (GE Healthcare Life Sciences, Pittsburgh, Pa.) was used to generate the image presentation data including the single and overlay images. The comparative analysis of all spots was done by the DeCyder analysis software (GE Healthcare Life Sciences, Pittsburgh, Pa.). The protein expression ratios between WFS1 knockout and control mice were generated and differentially expressed spots were analyzed by MALDI-TOF mass spectrometry.

Knockout Mice

WFS1 beta cell (brain-specific) knockout mice were generated by breeding Nestin-Cre transgenic mice (The Jackson Laboratory, Bar Harbor, Me.) with WFS1 floxed mice. WFS2 whole body knockouts were purchased from MRC Harwell (Oxfordshire, UK).

SERCA Assays

HEK293 cells were homogenized in hypotonic buffer containing 10 mM $NaHCO_3$, 250 mM sucrose, 5 mM $NaN_3$, and 0.1 mM PMSF. ER fractions were isolated using differential centrifugation. ER protein fractions (125 µg) were added to the assay mixture [100 mM KCL, 30 mM imidazole-histidine (pH 6.8), 5 mM $MgCl_2$, 5 mM ATP, 5 mM $(COOK)_2$, 5 mM $NaN_3$, and 50 µM $CaCl_2$ (10 uCi/µmol [$^{45}Ca$]; $CaCl_2$ American Radiolabeled Chemicals)] heated to 37° C. for 15 minutes. The reaction was quenched by the addition of 250 mM KCl and 1 mM $LaCl_3$. The mix was then vacuum filtered through a 0.2 µm HT Tuffryn membrane (Sigma-Aldrich (St. Louis, Mo.).). SERCA-dependent calcium transport was measured by comparing calcium transport in the presence or absence of 10 µM thapsigargin, a SERCA inhibitor.

ER Calcium Monitoring with D1ER

A β cell line was developed to monitor ER calcium levels under various conditions. The ER-localized calcium sensor D1ER was modified to contain two fluorescent proteins, CFP and YFP, which were inserted onto the N- and C-terminus, respectively. INS-1 832/13 cells were transfected with the modified D1ER calcium sensor. When $Ca^{2+}$ binds to the calmodulin, an intramolecular rearrangement occurs and brings CFP and YFP into close proximity resulting in a fluorescence resonance energy transfer (FRET) from CFP to YFP. The FRET signal allows ratiometric measurements of free ER $Ca^{2+}$ and changes in $Ca^{2+}$ using FRET/CFP ratio.

Caspase 3/7 Activity Assay

A Caspase 3/7 assay (Promega, Madison, Wis.) was utilized to measure caspase-3 and -7 activities in various cell lines. The assay provides a proluminescent caspase-3/7 substrate, which contains the tetrapeptide sequence DEVD. This caspase-3/7 substrate can be added directly to cell lysates. The substrate is cleaved to release a aminoluciferin, which is a substrate for luciferase used in the production of light. The signal is proportional to caspase-3/7 activity. The stabilized luciferase and proprietary buffer system improve assay performance across a wide range of assay conditions, and the assay is less likely to be affected by compound interference unlike fluorescent- or colorimetric-based assays Statistical Analysis Two-tailed t-tests were used to compare data. P values below 0.05 were considered significant. All values are shown as means±s.d. if not stated.

Example 2: WFS2 Interaction with CAPN2

The causative genes for Wolfram syndrome, WFS1 and WFS2, encode transmembrane proteins localized to the ER. Mutations in the WFS1 or WFS2 have been shown to induce neuronal and β cell death. To determine the cell death pathways emanating from the ER, proteins associated with WFS1 and WFS2 were sought.

HEK293T cells were transfected with GST-WFS2 plasmid and empty GST plasmid. Cell lysates were collected and immunoprecipitated with glutathione beads in lysis buffer (150 mM NaCl, 0.5% TRITRON X-100, 50 mM HEPES, 1 mM EDTA, 1 mM DTT, pH 7.5). The precipitated proteins from both samples were resolved by SDS-PAGE and stained with coomassie blue staining. The distinct bands that only appear in GST-WFS2 lane but not GST lane were analyzed by MALDI-TOF. Analysis revealed 13 interacting proteins (Table 1).

Figure 3A:
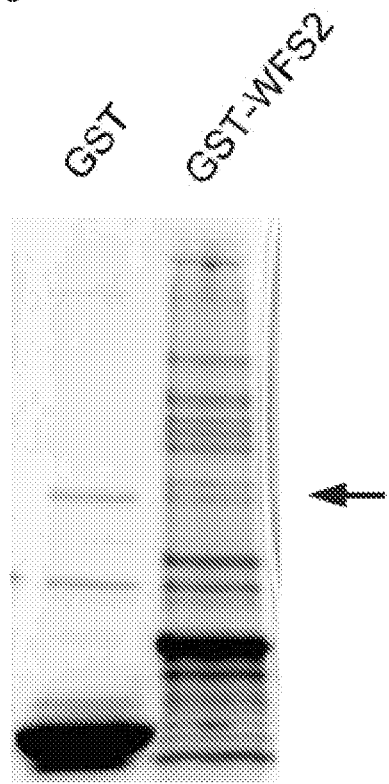
FIG. 3A is a depiction of a sodium dodecyl sulfate polyacrylamide gel electrophoresis (SDS-PAGE) of WFS2-associated proteins from HEK293T cell lysates transfected with glutathione S-transferase (GST) or GST-WFS2 expression plasmid.

One of the major WFS2-associated polypeptides was CAPN2, the catalytic subunit of calpain-2, a member of the calcium dependent cysteine proteases family whose members mediate diverse biological functions including cell death (FIG. 3A).

TABLE 1

GST-WFS2 interacting proteins

| Order on gel | Gene Symbol | Full Name | MW (kDa) |
|---|---|---|---|
| 1 | PRKDC | DNA dependent protein kinase catalytic subunit | 450 |
| 2 | COPA | Coatomer subunit alpha | 140 |
| 3 | IPO7, 4, 9 | Importin 7, 4, and 9 | 120 |
| 4 | XPO1, 2 | Exportin 1, 2 | 110 |
| 5 | MMS19 | MMS nucleotide excision repair | 110 |
| 6 | CNX | Calnexinp | 67 |
| 7 | CAPN2 | Calpain-2 | 80 |
| 8 | GRP78 | GRP78 | 78 |
| 9 | TUBA TUBB | Alpha and Beta Tubin | 50 |

Figure 3B:
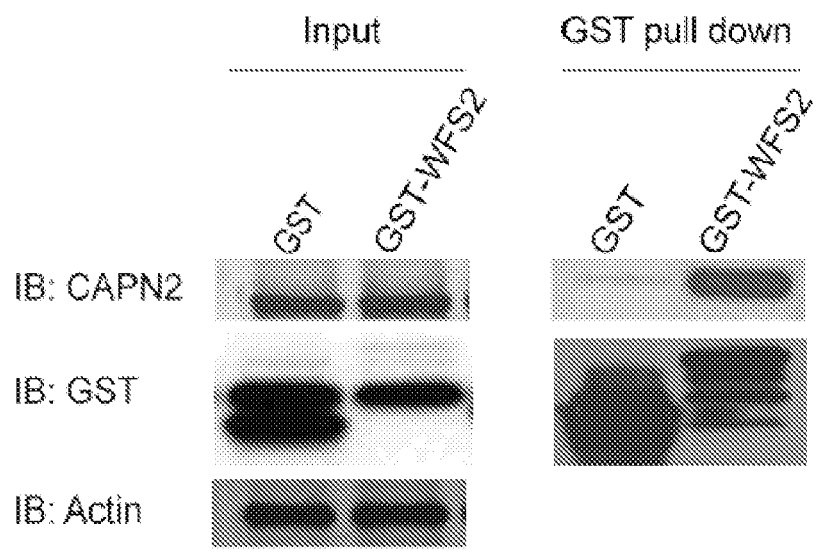
FIG. 3B is a depiction of a GST-tagged WFS2 pulled down of HEK293T cell lysates transfected with a GST-WFS2 expression plasmid, analyzed for CAPN2 by immunoblotting with anti-CAPN2 antibody.
Figure 3C:
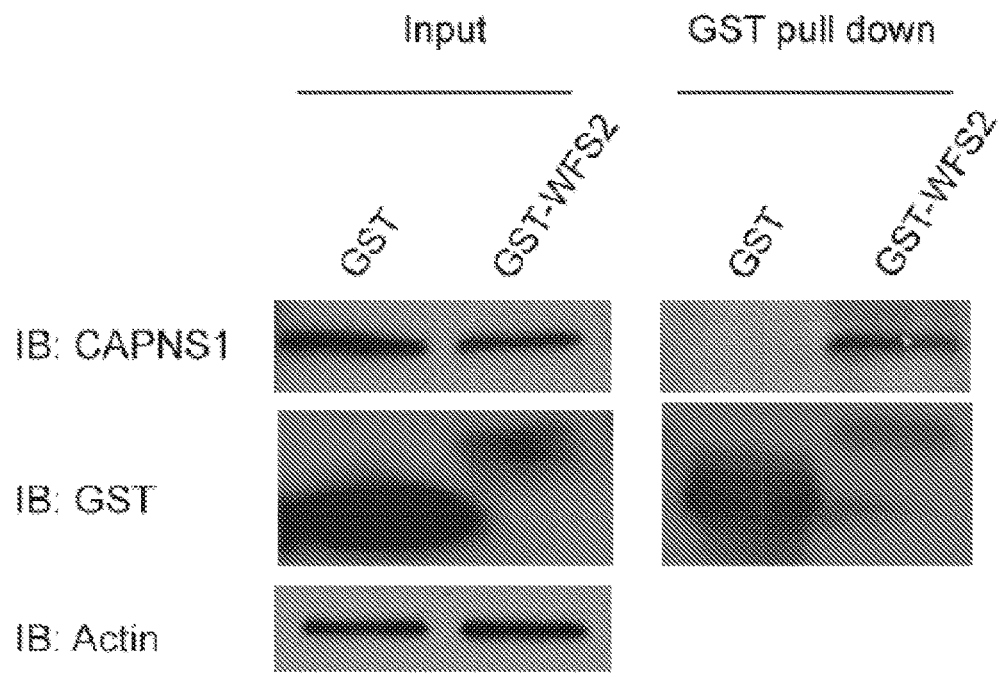
FIG. 3C is a depiction of a GST-tagged WFS2 pulled down of HEK293T cell lysates transfected with GST-WFS2 expression plasmid analyzed for CAPNS1 by immunoblotting with anti-CAPNS1 antibody.
Figure 3D:
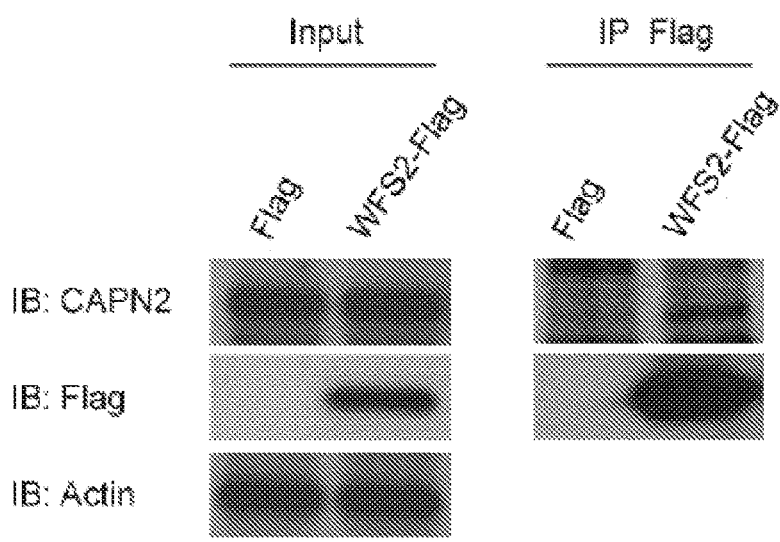
FIG. 3D is a depiction of an immunoblot of N-terminal FLAG-tagged WFS2 pull down of HEK293T cell lysates transfected with a WFS2 expression plasmid.
Figure 3E:
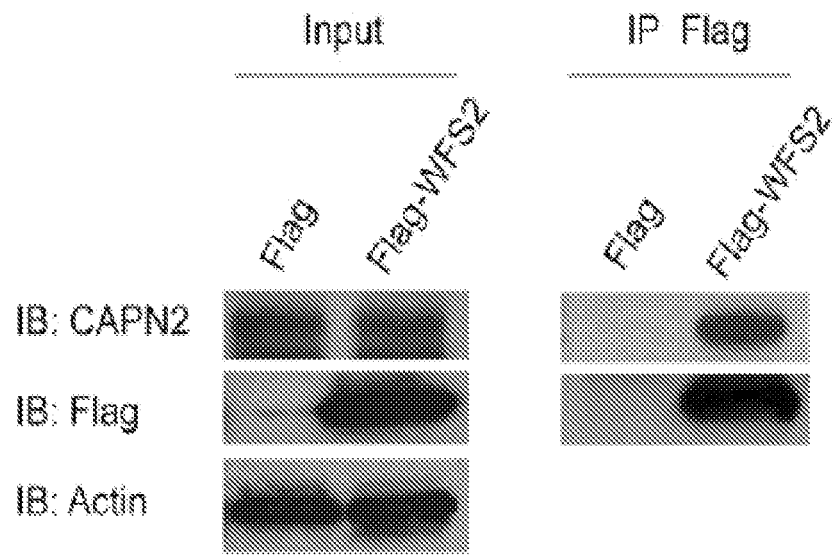
FIG. 3E is a depiction of an immunoblot of C-terminal FLAG-tagged WFS2 pull down of HEK293T cell lysates transfected with a WFS2 expression plasmid.

Calpain-2 is a heterodimer consisting of the CAPN2 catalytic subunit and the CAPNS1 (previously known as CAPN4) regulatory subunit. Interaction of WFS2 with calpain-2 was verified by showing that endogenous calpain-2 subunits CAPN2 (FIG. 3B) and CAPNS1 (FIG. 3C) each associated with GST-tagged WFS2 expressed in HEK293T cells. Endogenous calpain-2 was also found to be co-immunoprecipitated with N- or C-terminal FLAG-tagged WFS2 expressed in HEK293T cells (FIGS. 3D and 3E, respectively).

Figure 3F:
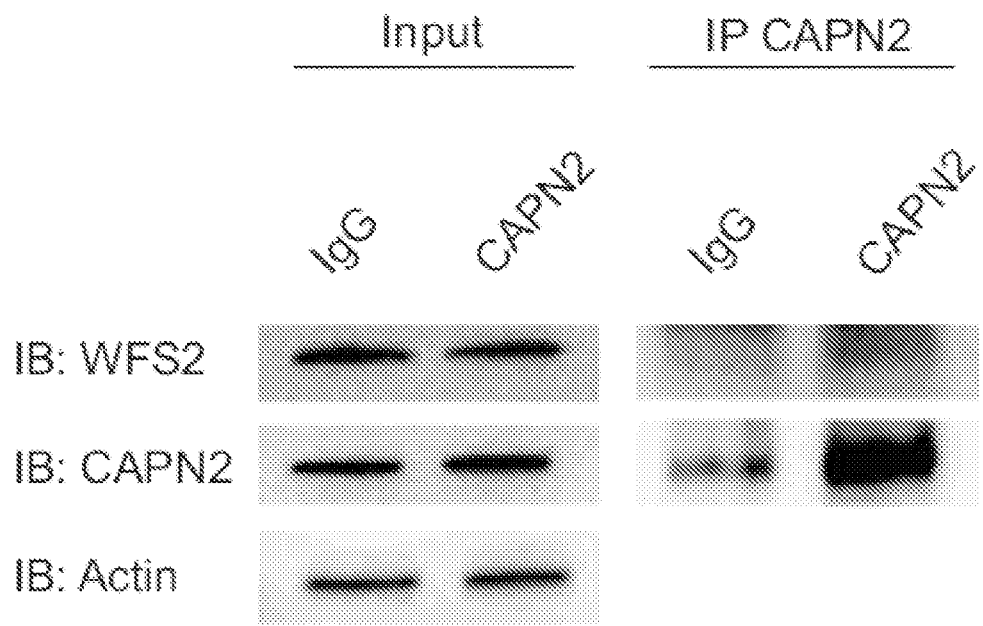
FIG. 3F is a depiction of an immunoblot of Neuro2a cell lysates immunoprecipitated with immunoglobin G (IgG) or anti-calpain-2 antibodies.
Figure 3G:
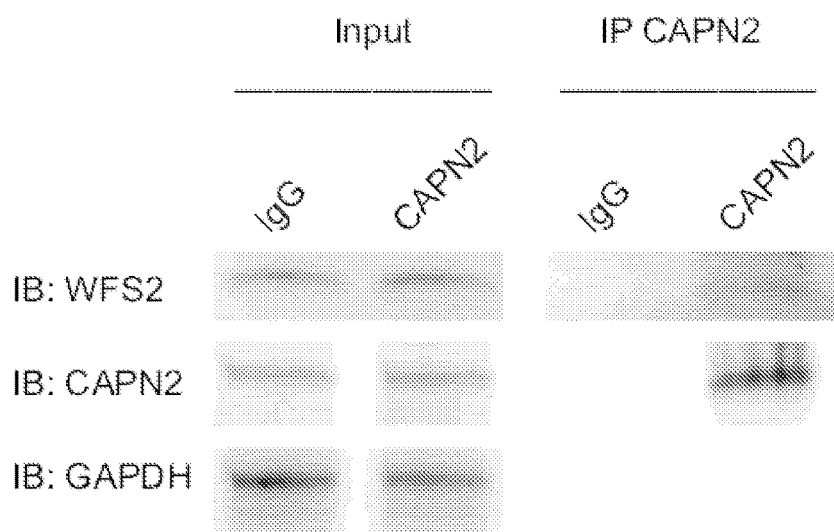
FIG. 3G is a depiction of an immunoblot of INS-1 832/13 cell lysates immunoprecipitated with IgG or anti-calpain-2 antibodies.
Figure 3H:
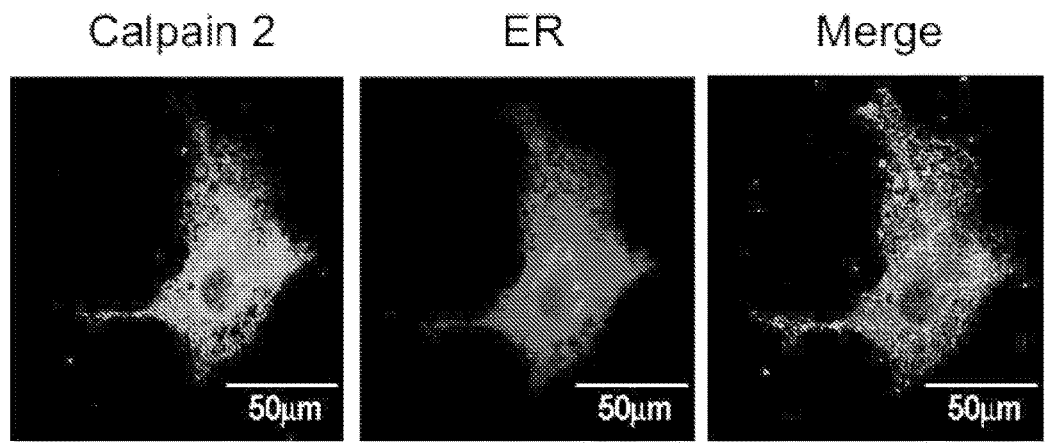
FIG. 3H is a depiction of COST cells transfected with pDsRed2-ER vector and stained with calpain-2 antibodies.
Figure 3I:
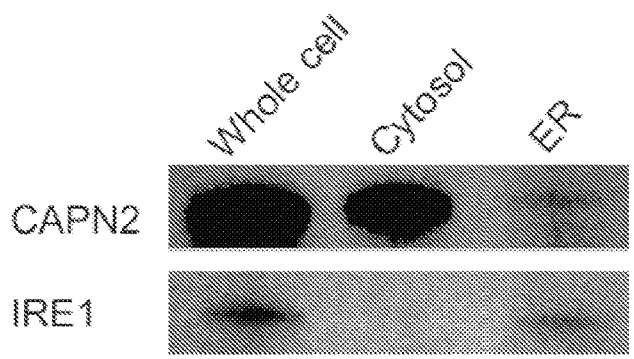
FIG. 3I is a depiction of an immunoblot of HEK293T cells transfected with WFS2 expression plasmids and fractioned into cytosolic and ER fractions.

To further confirm these findings, a co-immunoprecipitation experiment using IgG or anti-calpain-2 antibodies in Neuro2a cells (a mouse neuroblastoma cell line) and INS-1 832/13 cells (a rat pancreatic (3 cell line) was performed. It was found that endogenous WFS2 interacted with endogenous CAPN2 (FIGS. 3F and 3G). Since WFS2 is a transmembrane protein localized to the ER, the possibility that calpain-2 might also localize to the ER was explored by transfecting COS7 cells with pDsRed2-ER vector to visualize ER localization (FIG. 3H, center panel) Immunofluorescence staining of COS7 cells showed that endogenous calpain-2 was mainly localized to the cytosol, but also showed that a small portion colocalized with DsRed2-ER protein at the periphery of the ER (FIG. 3H, left panel). Cell were fractionated into cytosolic and ER fractions followed by immunoblotting which further confirmed this observation (FIG. 3I). Collectively, these results show that calpain-2 interacts with WFS2 at the periphery of the ER.

Figure 3J:
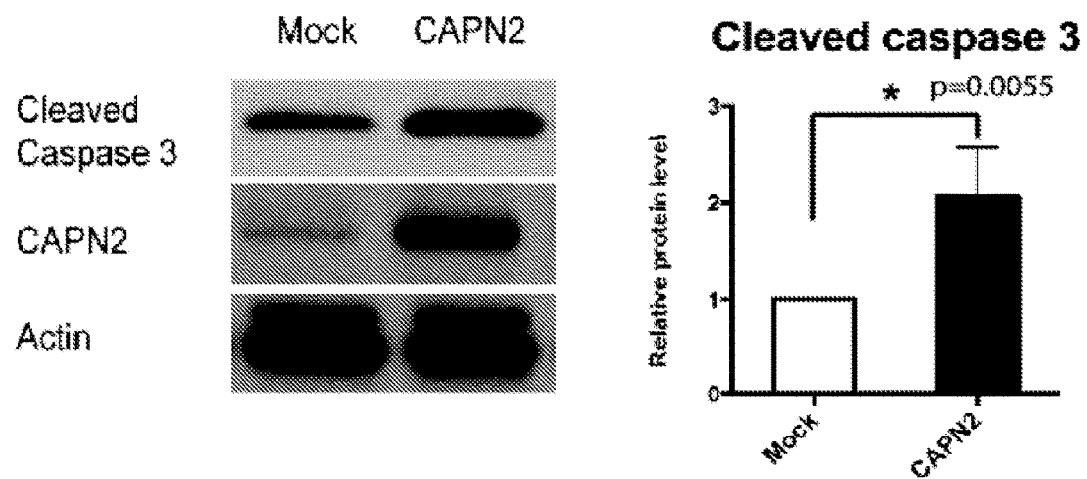
FIG. 3J is an immunoblot of HEK293T cells transfected with empty expression plasmid or a CAPN2 expression plasmid and a graph illustrating a change in expression levels of cleaved caspase 3.

Calpain hyper-activation has been shown to contribute to cell loss in various diseases, raising the possibility that calpain-2 might be involved in the regulation of cell death. To address this issue, the catalytic subunit of calpain-2 (CAPN2) was overexpressed. HEK293T Cells were transfected with empty expression plasmid or a CAPN2 expression plasmid. Apoptosis was monitored by immunoblotting analysis of caspase-3 cleavage. Expression levels of CAPN2 and actin were measured by immunoblotting (FIG. 3J, left panel). Quantification of the immunoblot is shown in FIG. 3J, right panel (n=3, *P<0.05). Over expression of calpain-2 was found to increase the cleavage of caspase-3 in HEK293T cells indicating that hyper-activation of calpain-2 induces cell death (FIG. 3J).

Example 3: WFS2 Suppresses Cell Death Mediated by CAPN2

To determine whether WFS2 plays a role in cell survival, WFS2 expression in NSC34 cells was suppressed using siRNA and cell viability was measured under normal and ER stress conditions. NSC34 cells were untreated (UT) or treated with 0.5 µM thapsigargin (TG) for 6 hours. WFS2 knockdown was associated with increased cleavage of caspase-3 in normal or ER stressed conditions (FIGS. 4A and 4B). Next, calpain-2 activation levels were evaluated by measuring the cleavage of alpha II spectrin, a substrate for calpain-2. RNAi-mediated knockdown of WFS2 was found to induce calpain activation, especially under stress conditions (FIG. 4A). Apoptosis was monitored by immunoblotting analysis of caspase 3 cleavage (FIG. 4A) (n=5, *P<0.05) and Annexin V staining (FIG. 4B) (n=3, *P<0.05). Additionally, proteins levels of cleaved spectrin, WFS2, and actin were measured by immunoblotting.

Figure 4C:
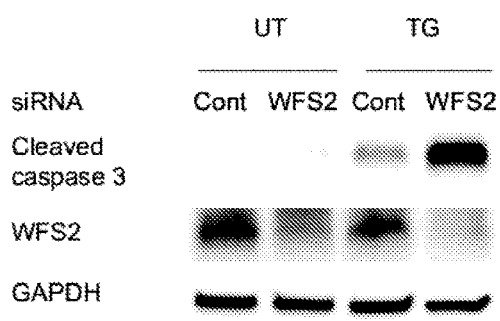
FIG. 4C is a depiction of an immunoblot of INS-1 832/13 cells transfected with scrambled siRNA or siRNA directed against WFS2 and a graph illustrating a change in expression levels of cleaved caspase 3
Figure 4C:
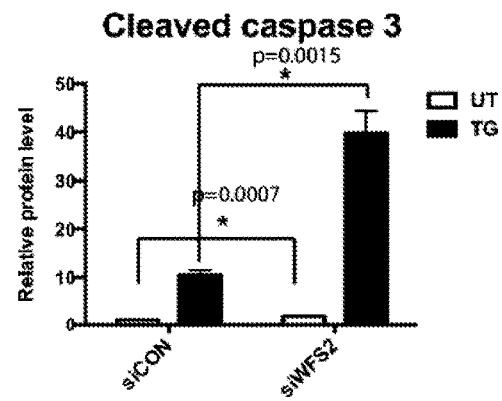
Figure 4D:
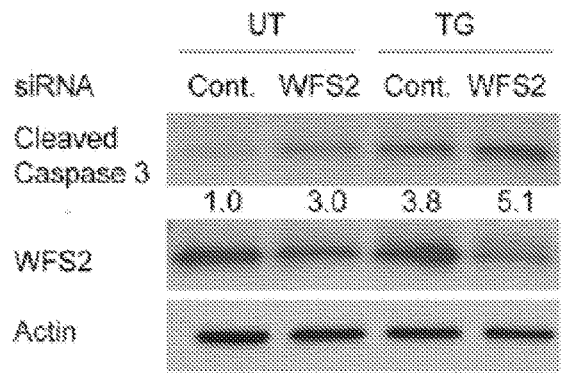
FIG. 4D is a depiction of an immunoblot of MING cells transfected with scrambled siRNA or siRNA directed against WFS2 and a graph illustrating a change in expression levels of cleaved caspase 3.
Figure 4D:
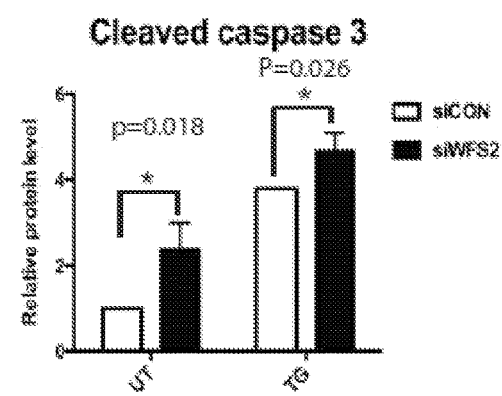

In subjects with Wolfram syndrome, destruction of β cells leads to juvenile-onset diabetes. However it is not known whether WFS2 is also involved in pancreatic β cell death. INS-1 832/13 (FIG. 4C) and MIN6 (FIG. 4D) cells were transfected with control scrambled siRNA or siRNA directed against WFS2 and then left untreated (UT) or treated with 0.5 µM thapsigargin (TG) for 6 hours. Expression levels of cleaved caspase-3, WFS2, and actin were measured by immunoblotting and are depicted in FIG. 4C (n=3, *P<0.05) and 4D (n=3, *P<0.05).

As was seen in neuronal cells, knockdown of WFS2 in rodent β cell lines INS1 832/13 (FIG. 4C) and MIN6 (FIG. 4D), was also associated with increased caspase-3 cleavage under both normal and ER stress conditions.

Figure 4E:
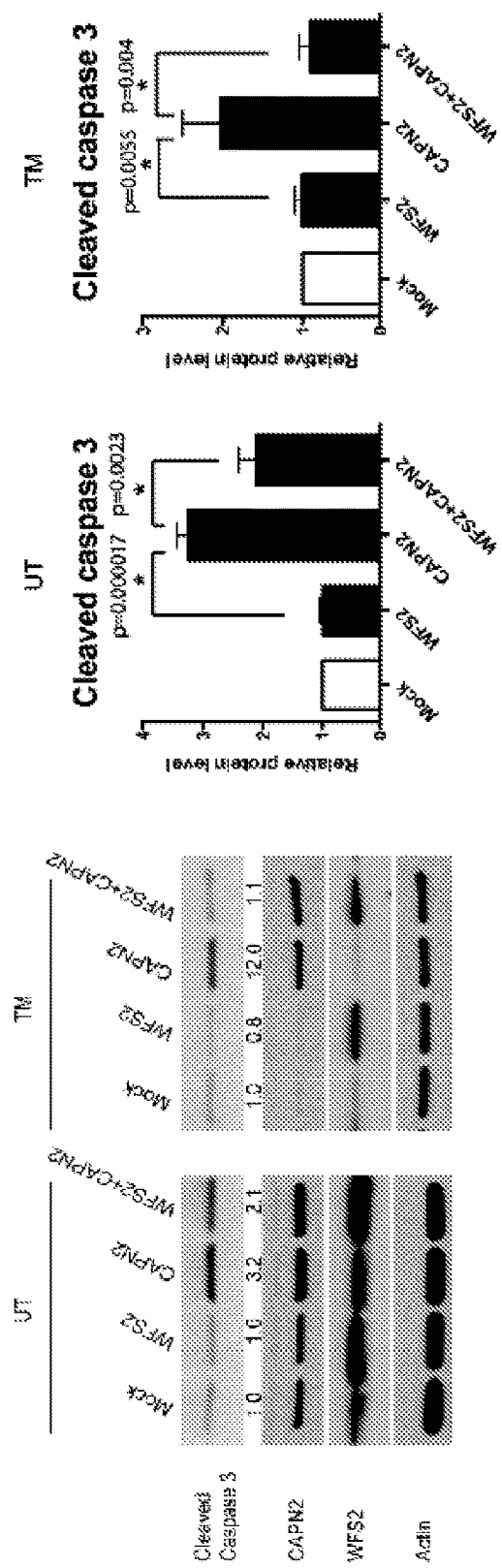
FIG. 4E is a depiction of an immunoblot of NSC34 cells transfected with empty expression plasmid, WFS2 expression plasmid, CAPN2 expression plasmid or co-transfected with WFS1 and CAPN2 expression plasmids and a graph illustrating a change in expression levels of cleaved caspase 3

NSC34 cells were transfected with empty expression plasmid (MOCK), WFS2 expression plasmid, CAPN2 expression plasmid or co-transfected with WFS1 and CAPN2 expression plasmids. After 24 hours, post transfection, cells were left untreated (UT) treated with 5 µg/mL tunicamycin (TM) for 16 hours. Apoptosis was monitored by immunoblotting analysis of the relative levels of cleaved caspase-3 (FIG. 4E, left panel). Expression levels of CAPN2, WFS2, and actin were also monitored by immunoblotting. Quantification of cleaved caspase-3 levels under treated and untreated conditions are shown in FIG. 4E, right panel (n=5, *P<0.05).

Figure 4F:
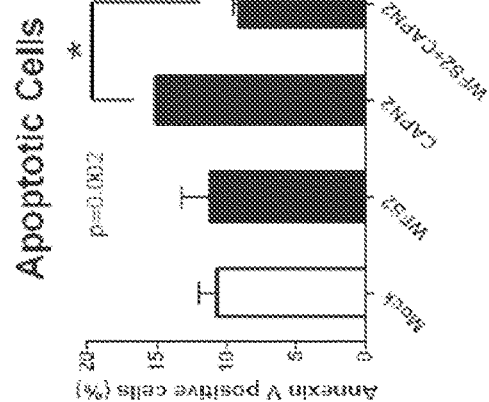
FIG. 4F is a graph illustrating apoptosis in Neuro2a cells transfected with empty expression plasmid, WFS2 expression plasmid, CAPN2 expression plasmid or co-transfected with WFS1 and CAPN2 expression plasmids.

The association of WFS2 with calpain-2 and their involvement in cell viability raised the possibility that calpain-2 activation might be the cause of cell death in WSF2 deficient cells. To test this hypothesis, WFS2 was expressed together with the calpain-2 catalytic subunit CAPN2 and apoptosis was measured. It was found that ectopic expression of WFS2 significantly suppressed calpain-2-associated apoptosis under normal and ER stress conditions (FIG. 4E, lanes 4 and 8, FIG. 4F). Next, the question of whether CPAN2 mediates cell death induced by WFS2 deficiency was tested.

Neuro2a cells were transfected with empty expression plasmid (MOCK), WFS2 expression plasmid, CAPN2 expression plasmid, or co-transfected with WFS1 and CAPN2 expression plasmids. The cells were examined for apoptosis by Annexin V staining followed by flow cytometry analysis (FIG. 4F) (n=3, *P<0.05).

Figure 4G:
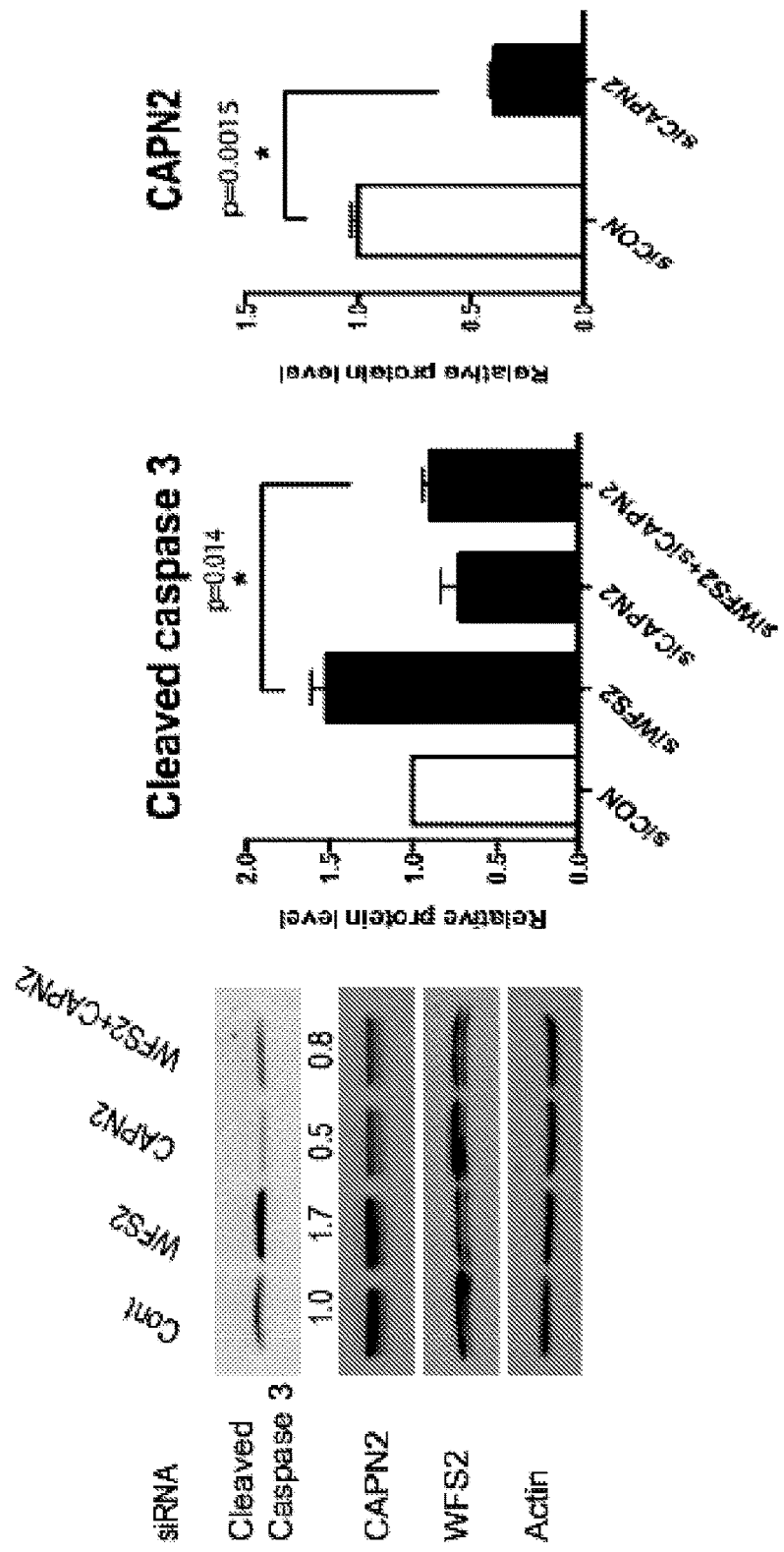
FIG. 4G is a depiction of an immunoblot of NSC34 cells transfected with scrambled siRNA, siRNA directed against WFS2, siRNA directed against CAPN2 or co-transfected with siRNA directed against WFS2 and siRNA directed against CAPN2 and a graph illustrating a change in expression levels of cleaved caspase 3 and CAPN2.

Additionally, NSC34 cells were transfected with scrambled siRNA (cont.), siRNA directed against WFS2, siRNA directed against CAPN2 or co-transfected with siRNA directed against WFS2 and siRNA directed against CAPN2. Apoptosis was detected by immunoblotting of cleaved caspase 3 (FIG. 4G, left panel). Protein levels of CAPN2, WFS2, and actin are shown in FIG. 4G (center and right panels) (n=3, *P<0.05).

When CAPN2 was silenced in WFS2 deficient cells, apoptosis was partially suppressed compared to untreated WFS2 deficient cells (FIG. 4G). Taken together, these results show that WFS2 is a negative regulator of calpain-2 pro-apoptotic functions.

Example 4: WFS2 Regulates Calpain Activity Through CAPNS1

Figure 5A:
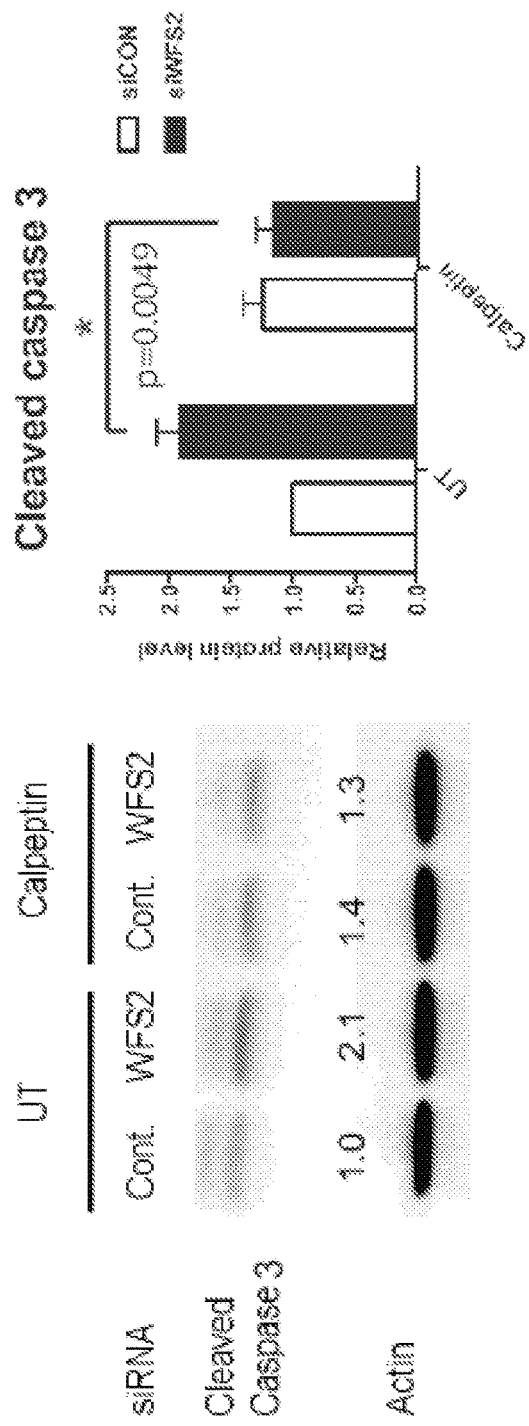
FIG. 5A is a depiction of an immunoblot of Neuro2a cells transfected with siRNA against WFS2 or a scrambled siRNA and a graph illustrating a change in expression levels of cleaved caspase 3.
Figure 5B:
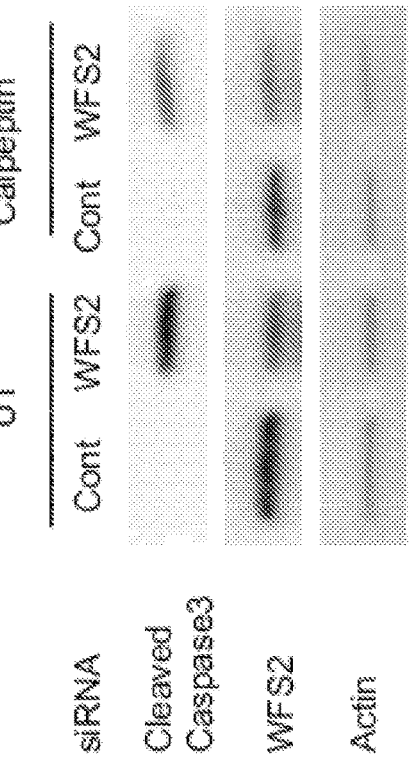
FIG. 5B is a depiction of an immunoblot of MIN6 cells transfected with scrambled with scrambled siRNA or siRNA directed against WFS2 untreated or treated with calpeptin.
Figure 5C:
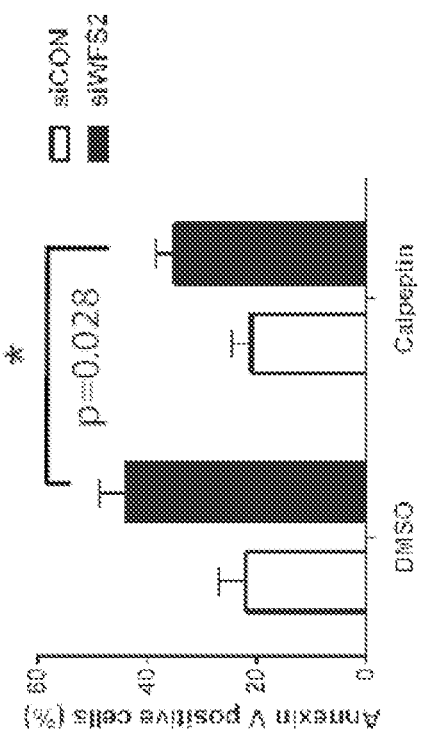
FIG. 5C is a graph of apoptosis in Neuro2a cells were transfected with scrambled siRNA or siRNA against WFS2 untreated or treated with calpeptin.

To further confirm that loss of function of WFS2 leads to cell death mediated by calpain-2, it was tested whether calpeptin (a calpain inhibitor) could prevent cell death in WFS2 deficient cells. Neuro2a and MIN6 cells were transfected with siRNA against WFS2 or a control scrambled siRNA (Cont.). After 36 hours post-transfection, cells were untreated or treated with 100 μM calpeptin for 12 hours. Cleaved caspase 3 and actin levels were assessed by immunoblotting (FIG. 5A, left panel). Quantified levels of cleaved caspase-3 are shown in FIG. 5A, right panel (n=3, *P<0.05). Quantification of protein levels from MIN6 cells are shown in FIG. 5B (n=3, *P<0.05). Additionally, early stage apoptosis was monitored by Annexin V staining followed by flow cytometry, FIG. 5C. INS-1 832/13 cells were transfected with scrambled siRNA and WFS2 siRNA. After 24 hours post-transfection, cells were untreated or treated with 5 μM calpeptin for 24 hours. Cleaved caspase-3, WFS2, and actin levels were monitored by immunoblotting (FIG. 5D, left panel) and quantified (FIG. 5D, right panel) (n=3, *P<0.05).

Figure 5D:
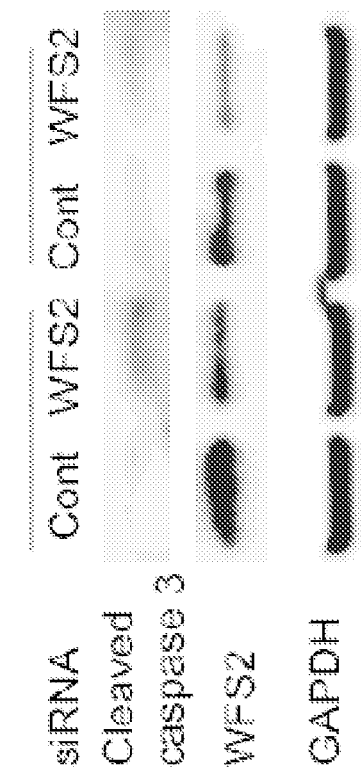
FIG. 5D is a depiction of an immunoblot of INS-1 832/13 cells transfected with scrambled siRNA and siRNA directed against WFS2 and a graph illustrating a change in expression levels of cleaved caspase 3.
Figure 5D:
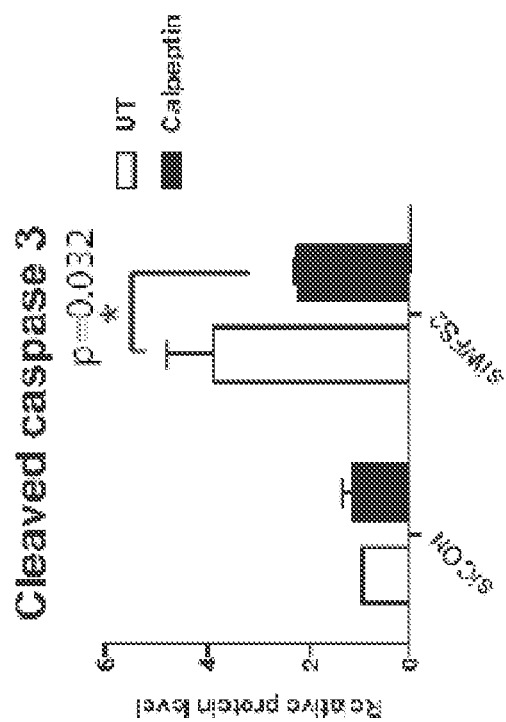

In agreement with previous observations, calpeptin treatment prevented WFS2-knockdown mediated cell death in neuronal (FIGS. 5A and 5C) and β cell lines (FIGS. 5B and 5D). Collectively, these results indicate that WFS2 is a suppressor of calpain-2-mediated cell death.

CAPN2 is the catalytic subunit of calpain-2. CAPN2 forms a heterodimer with the regulatory subunit, CAPNS1, which is required for protease activity and stability. Though it has been shown that WFS1 regulates protein stability and mediates cell fate decision, the role of WFS2 in CAPN2 and CAPNS1 protein stability is not known.

Figure 5E:
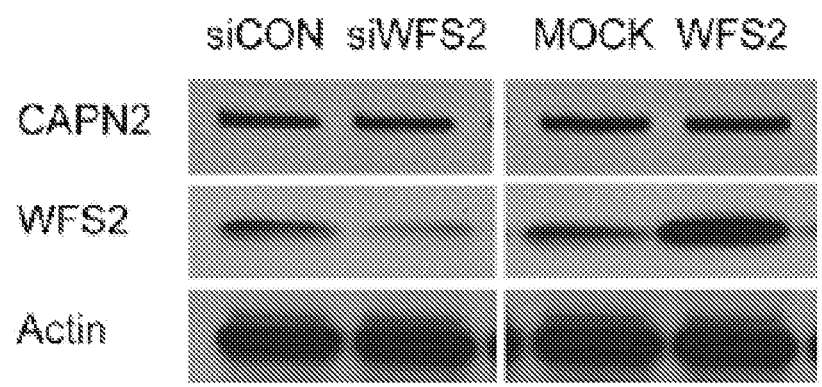
FIG. 5E is a depiction of an immunoblot of MIN6 cells transfected with scrambled siRNA, siRNA directed against WFS2, or empty expression plasmid.

CAPN2, WFS2, and actin levels were assessed by immunoblotting HEK293T cells transfected with empty expression plasmid (MOCK), WFS2 expression plasmid, scrambled siRNA (siCON), or siRNA directed against WFS2 (siWFS2) (FIG. 5E). It was found that ectopic expression of RNAi-mediated knockdown of WFS2 did not correlate with changes in the steady-state expression of CAPN2 (FIG. 5E).

Figure 5F:
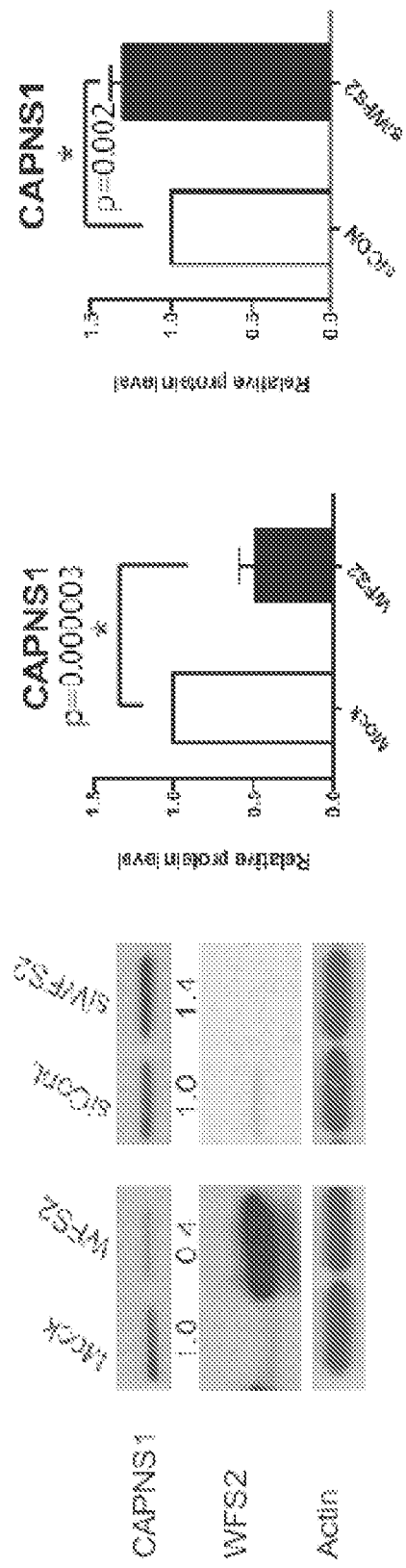
FIG. 5F is of HEK293T cells transfected with empty expression plasmid, WFS2 expression plasmid, scramble siRNA, or siRNA directed against WFS2 and a graph illustrating a change in expression levels of CAPNS1.

CAPNS1, WFS1, WFS2, and actin levels were assessed by immunoblotting HEK293T cells transfected with empty expression plasmid (MOCK), WFS2 expression plasmid, scrambled siRNA (siCON) or siRNA directed against WFS2 (siWFS2) (FIG. 5F, left panel). Protein levels of CAPNS1 were quantified and are shown in FIG. 5F, right panel. By contrast, overexpression of WFS2 significantly reduced CAPNS1 protein expression and transient suppression of WFS2 slightly increased CAPNS1 protein expression (FIG. 5F) (n=5, *P<0.05). This data shows that WFS2 might be involved in CAPNS1 protein turnover, which is supported by the data showing that GST-tagged WFS2 expressed in HEK293T cells associated with endogenous CAPNS1 (FIG. 3C).

Figure 5G:
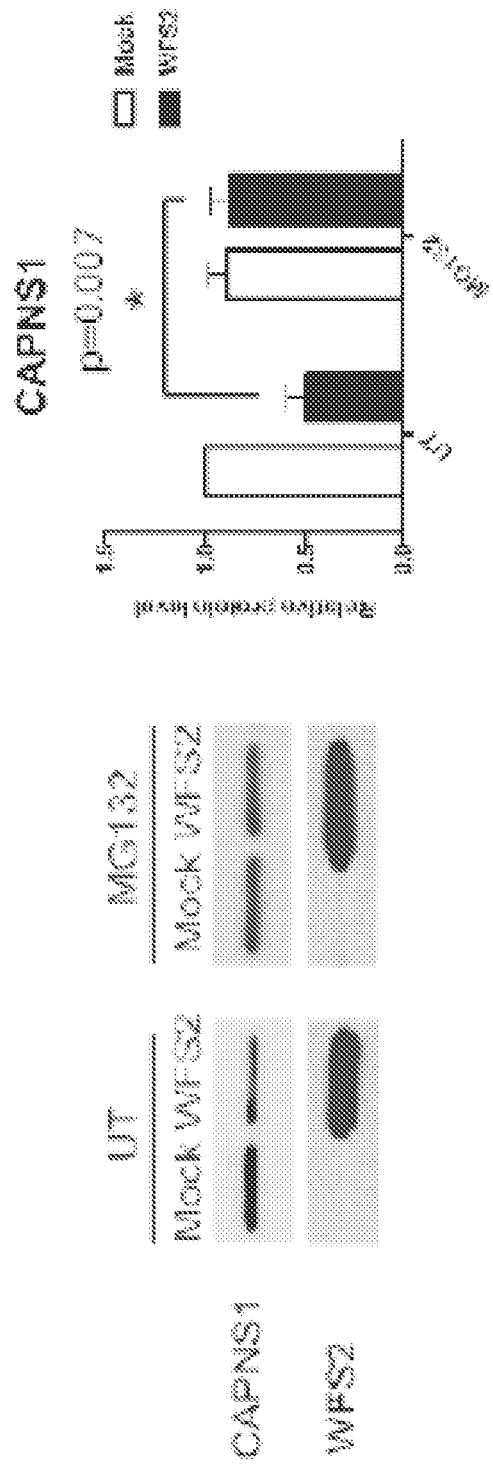
FIG. 5G is a depiction of an immunoblot of HEK293T cells transfected with empty or WFS2 expression plasmid untreated or treated with MG132 and a graph illustrating change in expression levels of CAPNS1.

To find out whether WFS2 regulates CAPNS1 stability through the ubiquitin-proteasome pathway, HEK293T cells ectopically expressing WFS2 were treated with a proteasome inhibitor, MG132 (2 μM), and then the CAPNS1 protein level was measured. MG132 treatment stabilized CAPNS1 protein in HEK293T cells ectopically expressing WFS2 (FIG. 5G) (n=4, *P<0.05).

Figure 5H:
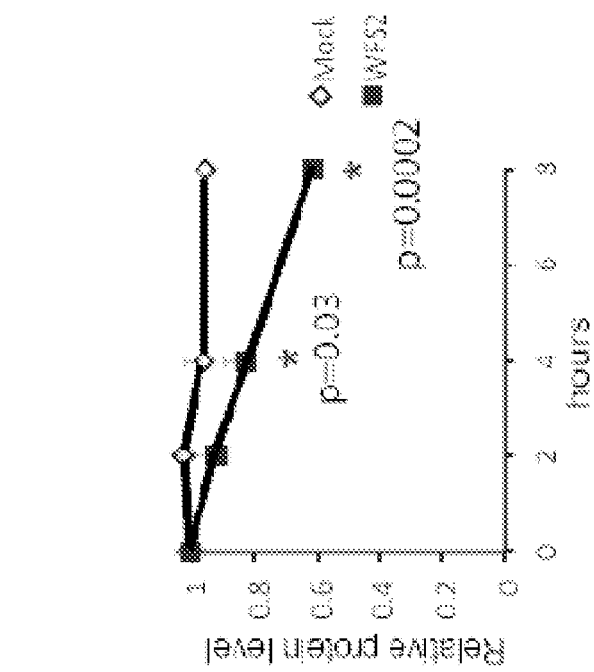
FIG. 5H is a depiction of an immunoblot of HEK293T cells transfected with empty or WFS2 expression plasmid, untreated or treated with cycloheximide and a graph illustrating a change in expression levels of CAPNS1 over time.
Figure 5H:
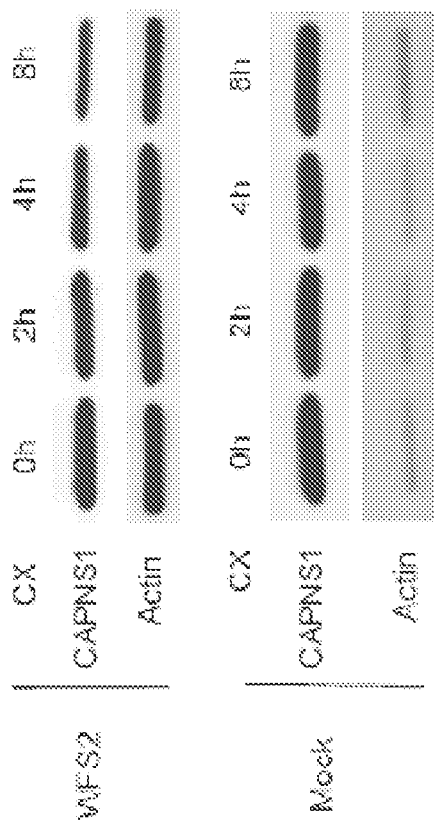

To further confirm that WFS2 is involved in the degradation of CAPNS1, cycloheximide chase experiments were performed using HEK293T cells ectopically expressing WFS2 and control cells. HEK293T cells were treated with 100 μM cycloheximide for various lengths of times, e.g., 0, 2, 4, and 8 hours. It was found that ectopic expression of WFS2 was associated with significantly accelerated CAPNS1 protein loss, indicating that WFS2 contributes to post-translational regulation of CAPNS1 (FIG. 5H) (n=3, *P<0.05).

Figure 5I:
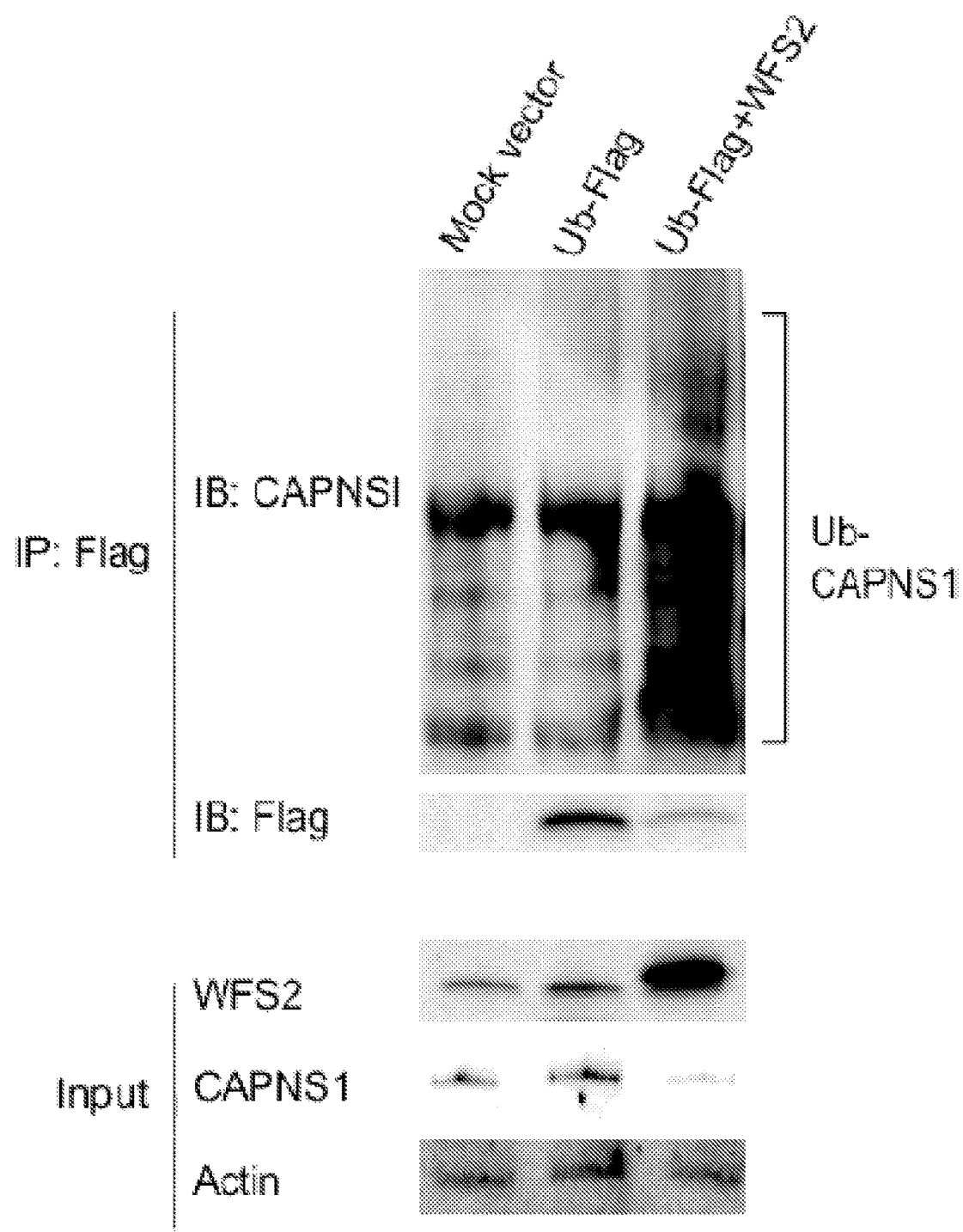
FIG. 5I is a depiction of an immunoblot of NSC34 cell lysates transfected with an empty vector, a FLAG tagged ubiquitin plasmid or co-transfected with WFS2 expression plasmid and Ub-FLAG plasmid.

To assess whether WFS2 is involved in the ubiquitination of CAPNS1, the levels of CAPNS1 ubiquitination in cells ectopically expressing WFS2 were measured. NSC34 cells were transfected with mock empty vector, FLAG tagged ubiquitin (Ub-FLAG) plasmid or co-transfected with WFS2 expression plasmid and Ub-FLAG plasmid. Cell lysates were immunoprecipitated with FLAG affinity beads and analyzed for ubiquitin conjugated proteins by immunoblotting. Levels of CAPNS1 and Ub-FLAG proteins were measured in the precipitates. WFS2, CAPNS1, and actin expression was monitored in the input samples. It was found that CAPNS1 ubiquitination was increased by ectopic expression of WFS2 (FIG. 5I).

Figure 5J:
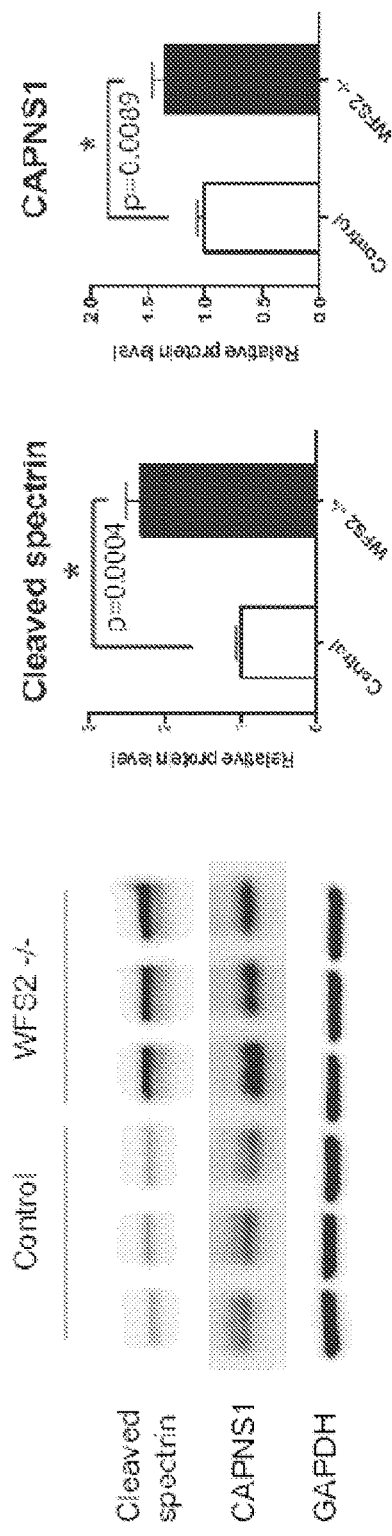
FIG. 5J is a depiction of an immunoblot of brain lysates from control and WFS2 knockout mice and a graph illustrating a change in expression levels of cleaved spectrin and CAPNS1.

To further investigate the role of WFS2 in calpain-2 regulation, brain lysates from WFS2 knockout mice were collected, immunoblotted, and levels of cleaved spectrin were determined (spectrin is a well-characterized substrate for calpain). Notably, protein expression levels of cleaved spectrin, as well as CAPNS1, were significantly increased in WFS2 knockout mice as compared to control mice (FIG. 5J) (each group, n=3, *P<0.05). Collectively, these results indicate that WFS2 inhibits calpain-2 activation by regulating CAPNS1 degradation mediated by ubiquitin-proteasome system.

Example 5: Calpain-2 Activation in a Mouse Model of Wolfram Syndrome

Figure 6A:
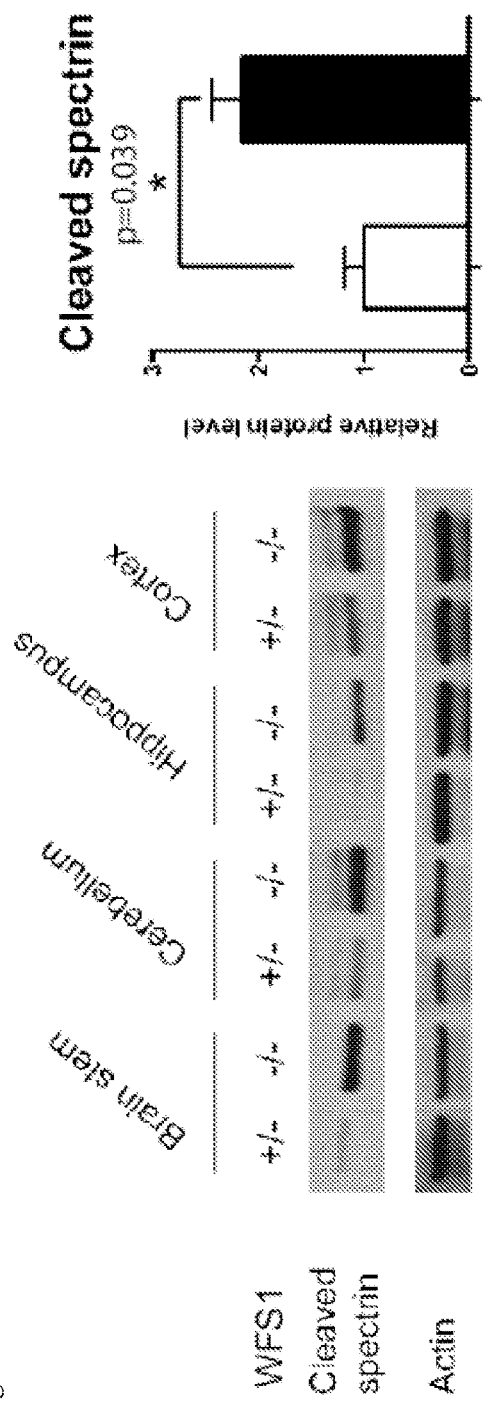
FIG. 6A is a depiction of an immunoblot of protein was extracted from brain tissues of WFS1 brain specific knockout and control mice and a graph illustrating a change in expression levels of cleaved spectrin and CAPNS1.
Figure 6B:
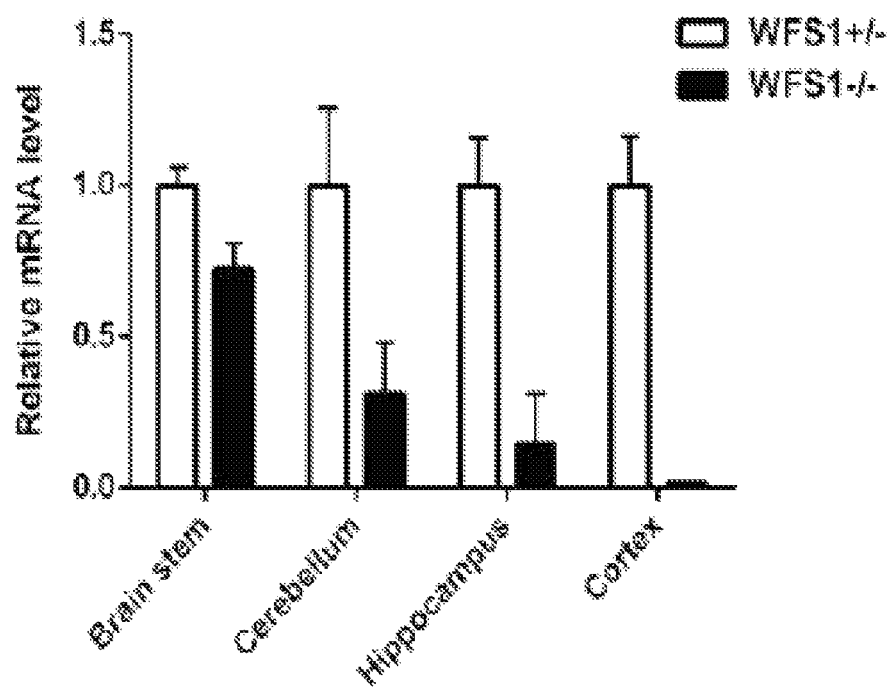
FIG. 6B is a graph illustrating relative levels of WFS1 mRNA in different parts of the brain of WFS1 knockout and control mice.

Calpain-2 is a calcium-dependent protease. WFS1, the other causative gene for Wolfram syndrome, has been shown to be involved in calcium homeostasis, raising the possibility that the loss of function of WFS1 is also involved in calpain activation. To test this idea, calpain activation levels in brain tissues from WFS1 knockout and control mice were measured. It was found that increased levels of a spectrin cleavage product, reflecting calpain activation, were observed in WFS1 knockout mice as compared to control mice (FIG. 6A). Cleaved alpha II spectrin and actin levels were determined by immunoblot analysis (FIG. 6A, left panel). Quantification of cleaved spectrin is shown in FIG. 6A, right panel (each group, n=10, *P<0.05). WFS1 mRNA levels in different parts of the brain in WFS1(−/−) and WFS1(+/−) mice were measured by qRT-PCR. The suppression levels of WFS1 in different parts of brain are shown in FIG. 6B.

Figure 6C:
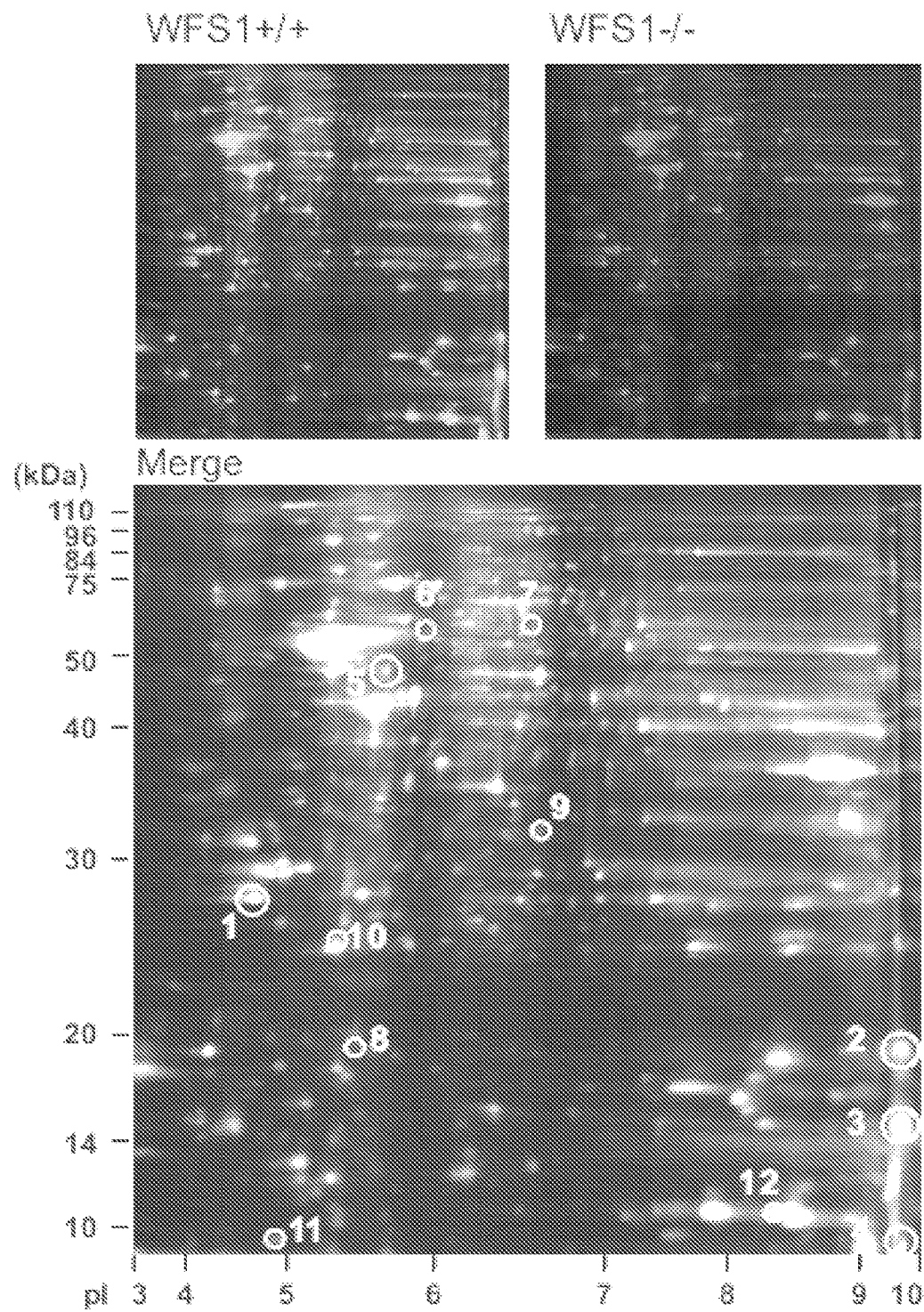
FIG. 6C is a 2-D fluorescence difference gel electrophoresis of proteins extracted from the cerebellum of WFS1 knockout and control mice.
Figure 6D:
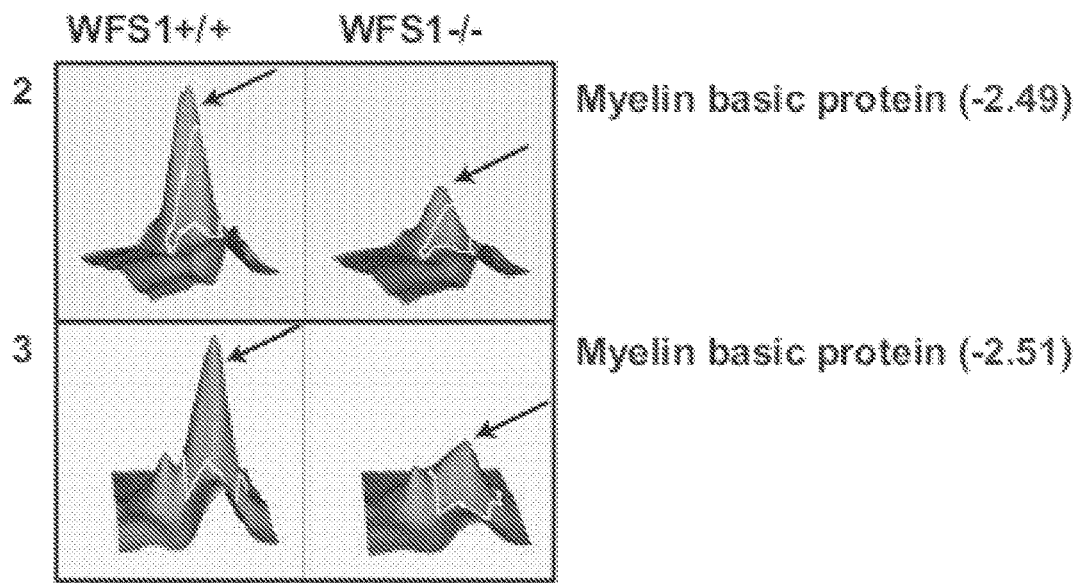
FIG. 6D is a protein expression profile illustrating difference between WFS1 knockout and control mice.
Figure 6E:
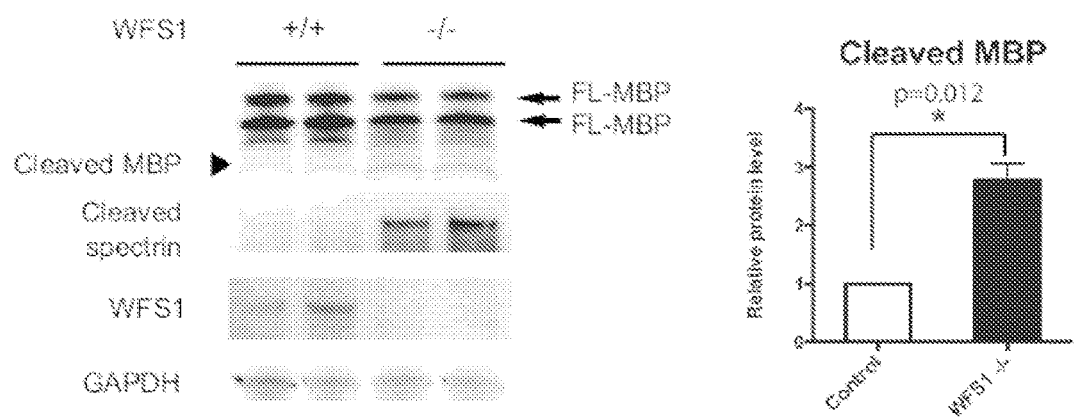
FIG. 6E is a depiction of an immunoblot of proteins extracted from the cerebellum of WFS1 brain specific knockout and control mice and a graph illustrating a change in expression levels of cleaved MBP.

To further confirm that calpain is activated by the loss of function of WFS1, other substrates for calpain in brain tissues from WFS1 knockout mice were identified by proteomics. 2-D fluorescence gel electrophoresis identified 12 proteins differentially expressed between cerebellums of WFS1 knockout mice and those of control mice (FIG. 6C, circled). Protein expression ratios between WFS1 knockout and control mice were generated and differentially expressed spots were analyzed by MALD-TOF mass spectrometry. Quantitative diagrams of spots #2 and #3, identified as myelin basic protein, show lower levels of expression in WFS1 knockout mice as compared to control mice (FIG. 6D, the positive numbers indicate an increase in expression level whereas a negative number indicates a decrease in expression level). Among these, myelin basic protein (MBP) is a known substrate for calpain in the brain. To confirm that myelin basic protein cleavage was enhanced in WFS1 knockout mice, myelin basic protein levels in brain lysates, extracted from the cerebellum, from WFS1 knockout and control mice were measured. It was found that the cleavage and degradation of myelin basic protein was increased in WFS1 knockout mice as compared to control mice (FIG. 6E) (each group, n=3, *P<0.05).

Figure 7A:
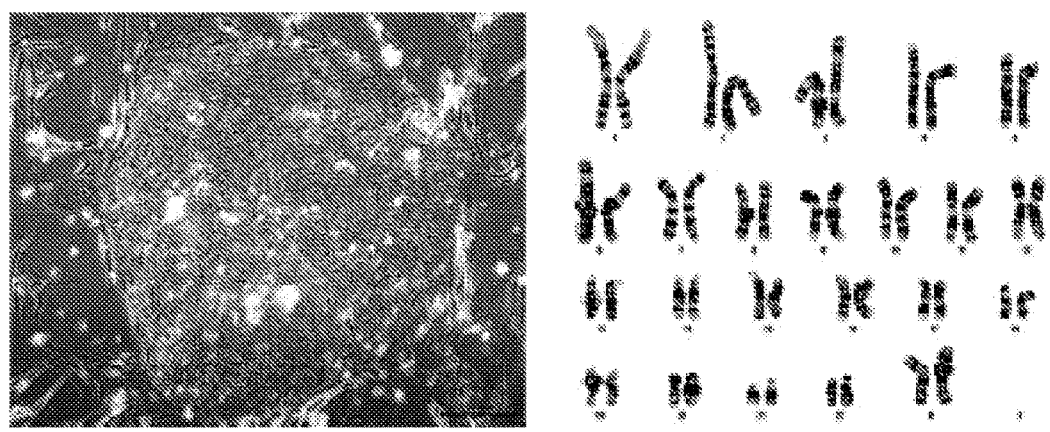
FIG. 7A is an image of iPS cells derived from fibroblasts and a karyotype of Wolfram iPS cells.
Figure 7B:
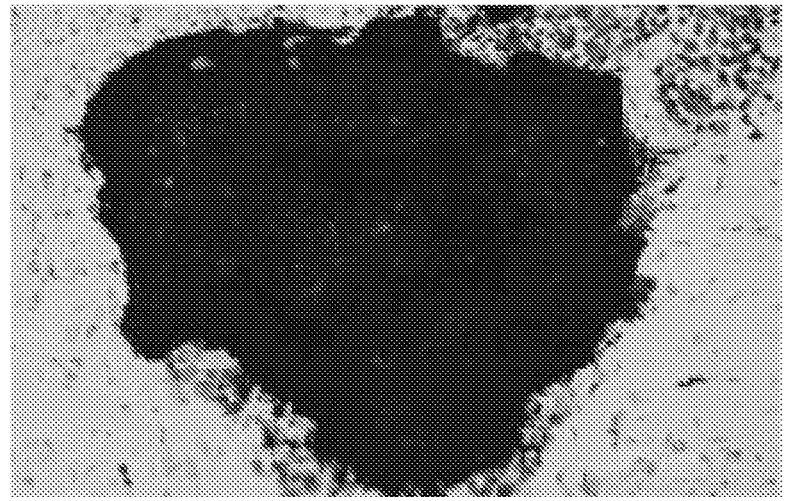
FIG. 7B is an image of alkaline phosphatase staining of the Wolfram iPS cells.
Figure 7C:
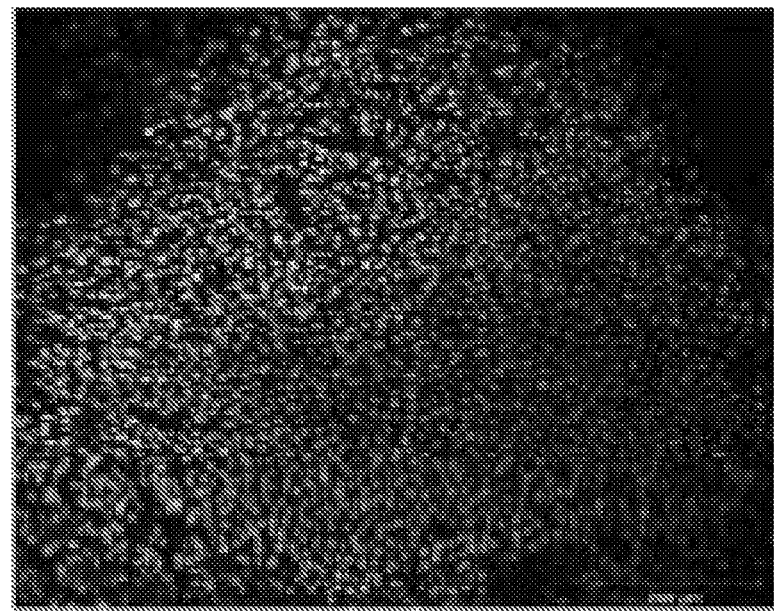
FIGS. 7C, 7D, 7E, and 7F are images of Wolfram syndrome iPS cells stained with pluripotent markers.
Figure 7D:
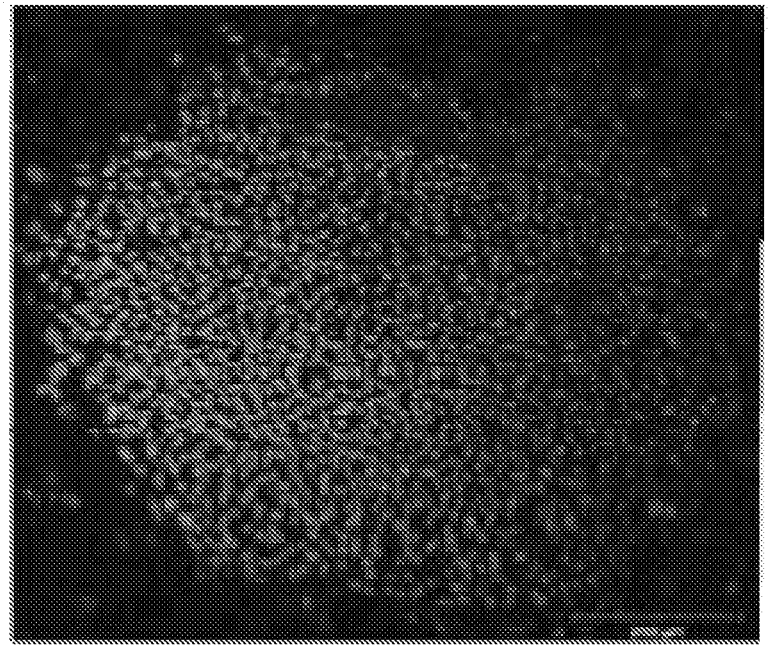
Figure 7E:
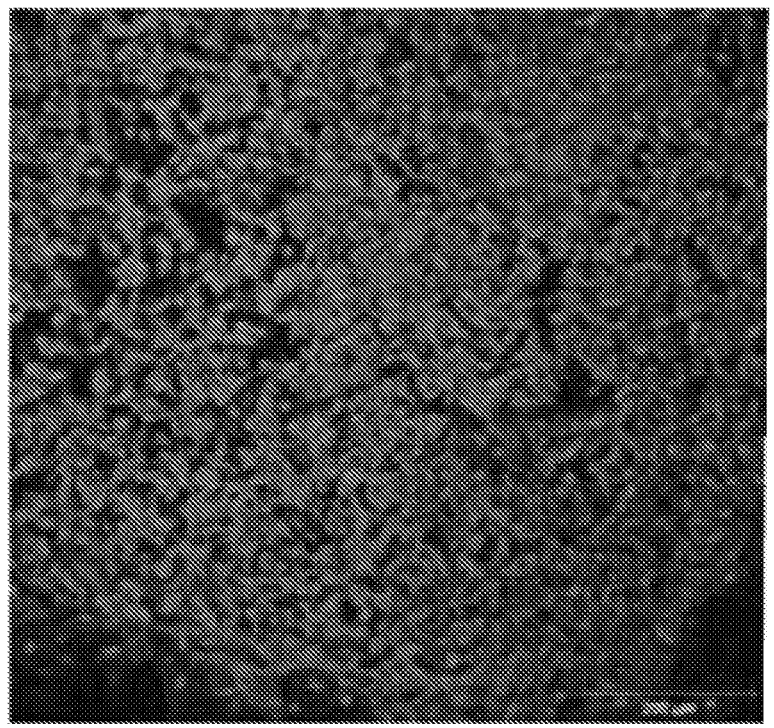
Figure 7F:
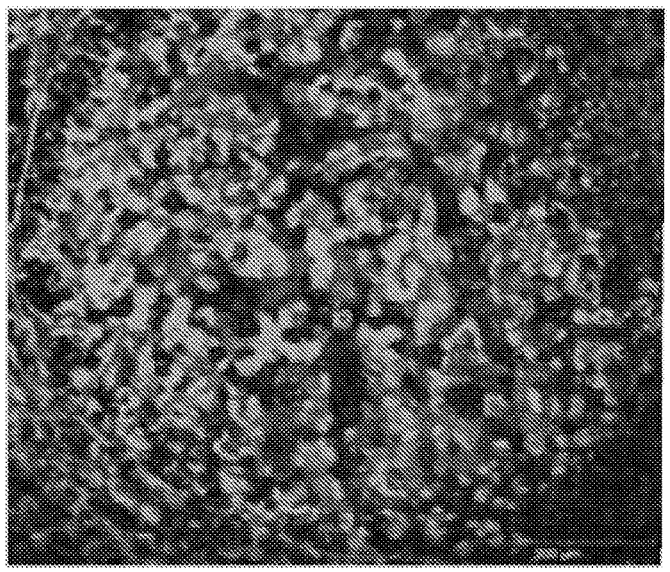
Figure 7G:
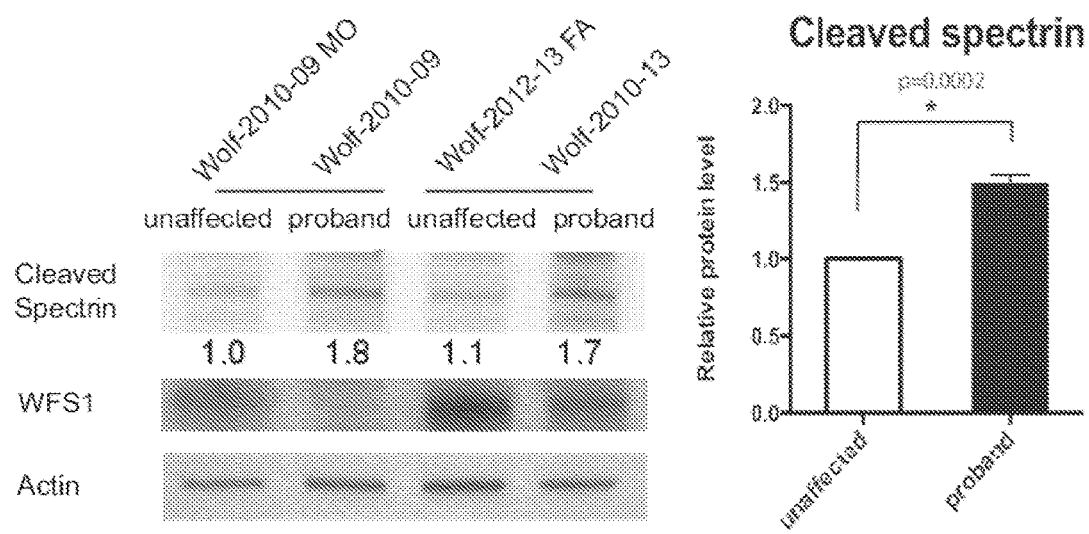
FIG. 7G is a depiction of an immunoblot of cleaved spectrin and actin in neural progenitor cells derived from Wolfram syndrome subject iPS cells and a graph illustrating a change in expression levels of cleaved spectrin.

Example 6: High Cytosolic Calcium Levels and Hyper-Activation of Calpain in Neural Progenitor Cells To further confirm these observations, evidence was sought for increased calpain activity in neural progenitor cells derived from induced pluripotent stem cells (iPSCs) of Wolfram syndrome subjects with mutations in WFS1. Fibroblasts from four nonaffected controls and five subjects with Wolfram syndrome were transduced with four reprogramming genes (Sox2, Oct4, c-Myc, and Klf4) (28) (Table 2). At least ten clones from each control- and Wolfram-iPSCs were produced. All control- and Wolfram-iPSCs, exhibited characteristic human embryonic stem cell morphology, expressed pluripotency markers including ALP, NANOG, SOX2, SSEA4, TRA-1-81, and had a normal karyotype (FIGS. 7A, 7B, 7C, 7D, 7E, and 7F). To create neural progenitor cells, neural aggregates from iPSCs were formed. Neural aggregates were harvested at day 5 and re-plated onto new plates to give rise to colonies containing neural rosette structures. At day 12, neural rosette clusters were collected, re-plated, and used as neural progenitor cells. It was found that spectrin cleavage was increased in neural progenitor cells derived from Wolfram-iPSCs as compared to ones from control iPSCs, which indicates increased calpain activity (FIG. 7G). The relative levels of the spectrin cleavage product are indicated (FIG. 7G, left panel) and quantified (FIG. 7G, right panel) (n=4, *P<0.05).

TABLE 2

Information on genotypes and phenotypes of Wolfram syndrome and control subjects

| iPSC line | Source | Clinical Diagnosis | WFS1 mutation | Sex | Age at biopsy | Age at onset of DM[a] | Age at onset of OA[b] | Age of onset of Deafness | DI[c] |
|---|---|---|---|---|---|---|---|---|---|
| Wolf-2010-5 | WUWC[d] | WFS[e] | H313Y | F | 15 | 3.8 | 12 | 1.7 | N/A |
| Wolf-2010-9 | WUWC | WFS | A126T; W613X | M | 16 | 10.8 | 11 | NA | 14 |
| Wolf-2010-11 | WUWC | WFS | A126T; W613X | M | 10 | 7.5 | 6 | 8 | 10 |
| Wolf-2010-13 | WUWC | WFS | L200fs286Stop; E752Stop | F | 7 | 4.8 | 5.2 | 6 | 7.5 |
| GM01610 | CRI[f] | WFS | W648X; G695V | F | 11 | NA | NA | NA | NA |
| BJ CRL-2522 | ATCC[g] | Control | NA | M | Newborn | NA | NA | NA | NA |
| Wolf-2010-5-MO | WUWC | Control | None identified | F | 41 | NA | NA | No | No |
| Wolf-2010-9-MO | WUWC | Control | NA | F | 33 | NA | NA | No | No |
| Wolf-2012-13-FA | WUWC | Control | NA | M | 42 | NA | NA | No | No |

Figure 7H:
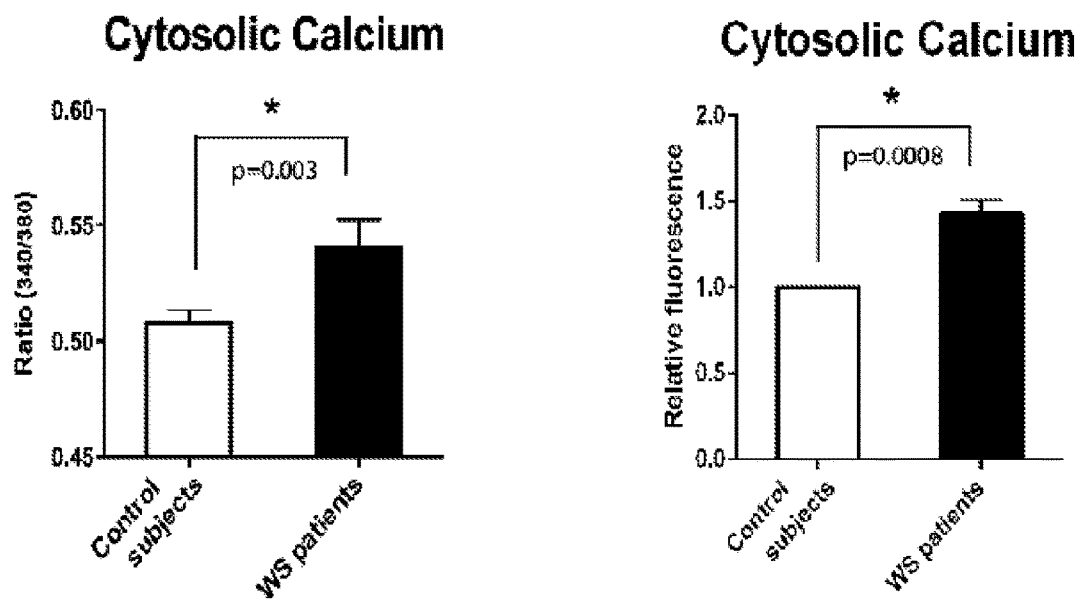
FIG. 7H is a graph illustrating changes in cytosolic calcium levels in unaffected controls and Wolfram syndrome subjects measured by Fura-2.

[a]DM: diabetes mellitus;
[b]OA: optic atrophy;
[c]DI: diabetes insipidus
[d]WUWC: Washington University Wolfram Clinic;
[e]WFS: Wolfram syndrome;
[f]CRI: Corriell Research Institute;
[g]ATCC:

The finding that calpain appeared to be hyperactivated in neural progenitor cells derived from Wolfram-iPSCs raised the possibility that cytoplasmic calcium levels might be increased in these cells. To test this idea, cytoplasmic calcium levels of neural progenitor cells derived from control—were compared with Wolfram-iPSCs cells using Fura-2, a fluorescent calcium indicator allowing accurate measurements of cytoplasmic calcium concentrations. FIG. 7H (left panel) shows that cytoplasmic calcium levels were higher in Wolfram-iPSCs derived cells than in control cells. This was confirmed by staining these cells with another fluorescent calcium indicator, Fluo-4 (FIG. 7H, right panel) (n=4, *P<0.05).

Figure 7I:
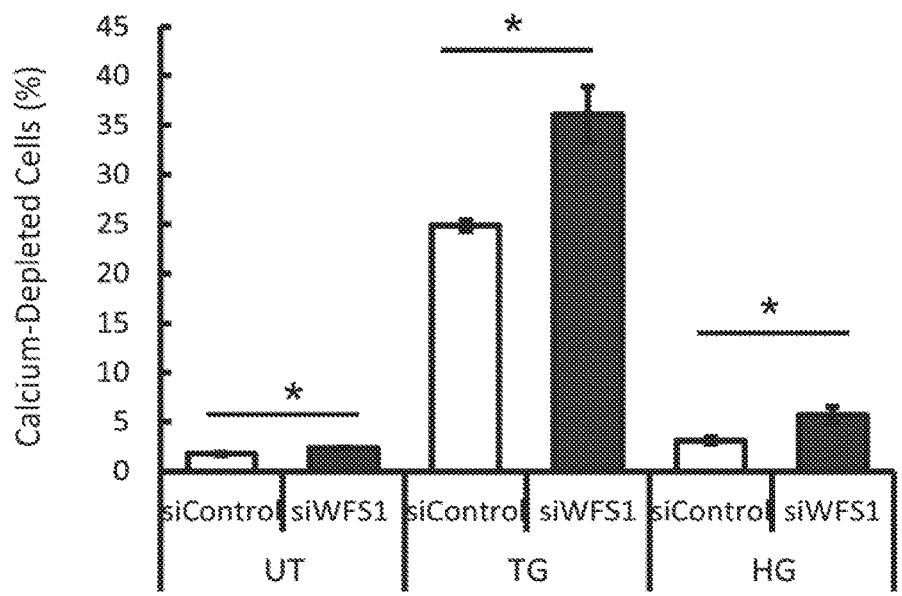
FIG. 7I is graph illustrating rates of ER calcium depletion in INS-1 832/13 cells transfected with scrambled siRNA or siRNA directed against WFS1.

Additionally, INS-1 832/13 cells transfected with scrambled siRNA or siRNA directed against WFS1 and then untreated or treated with 10 nM thapsigargin for 24 hours or 25 mM high glucose for 48 hours. The percent rates of ER calcium depletion in INS-823/13 cells stained with Fluro-4 are shown in FIG. 7I. RNAi-mediated knockdown of WFS1 in INS-1 832/13 cells increased the rate of ER-calcium depleted cells under ER stress or high glucose conditions.

Figure 7J:
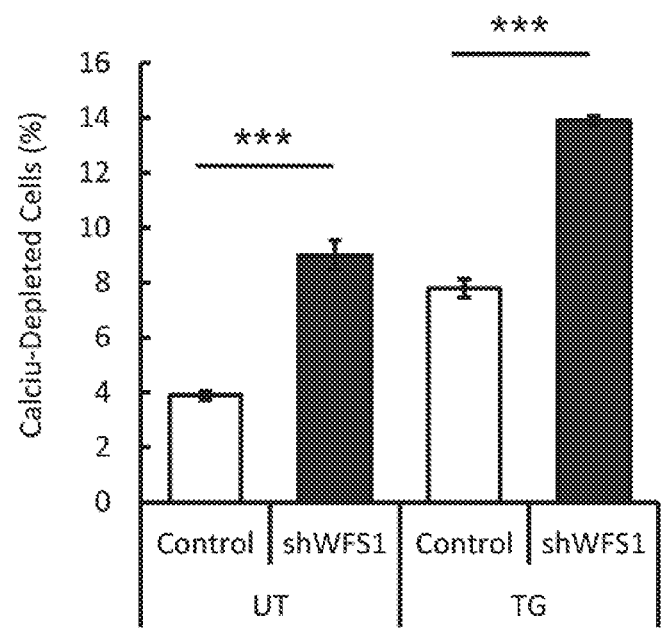
FIG. 7J is a graph illustrating rates of ER calcium depletion in HEK293 cells, transduced with lentivirus expressing scrambled shRNA or shRNA directed against WFS1, untreated or treated with thapsigargin.
Figure 7K:
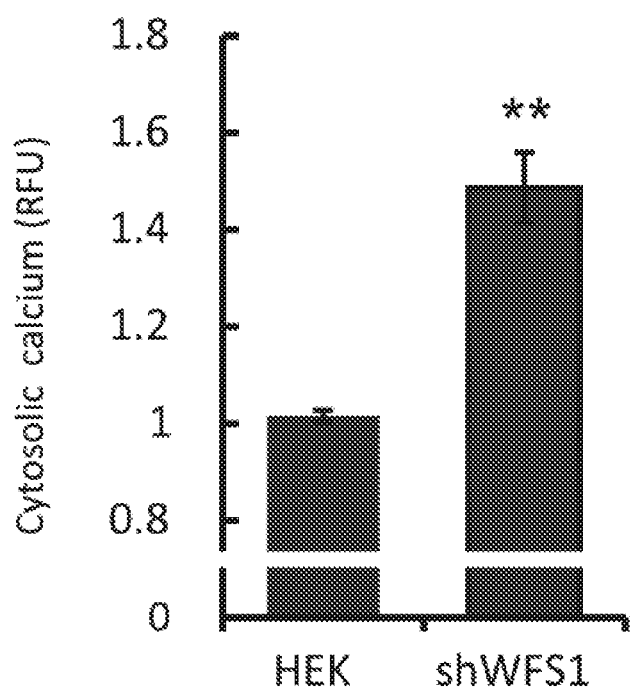
FIG. 7K is a graph illustrating cytosolic calcium levels in HEK293 cells transducted with lentivirus expressing scramble shRNA or shRNA directed against WFS1.

HEK293 cells were transfected with lentivirus expressing scrambled shRNA or shRNA directed against WFS1 and then untreated or treated with 10 nM thapsigargin for 24 hours. shRNA-mediated knockdown of WFS1 in HEK293 cells, stained with Fluo-4, also increased the rate of ER calcium-depleted cells under normal and ER stress conditions (FIG. 7J) and increased the cytosolic calcium concentrations (FIG. 7K). Collectively, these results indicate that loss of function of WFS1 increases cytoplasmic calcium levels, leading to calpain activation.

Example 7: Prevention of Cell Death and Restoration of Calcium Homeostasis

Figure 8A:
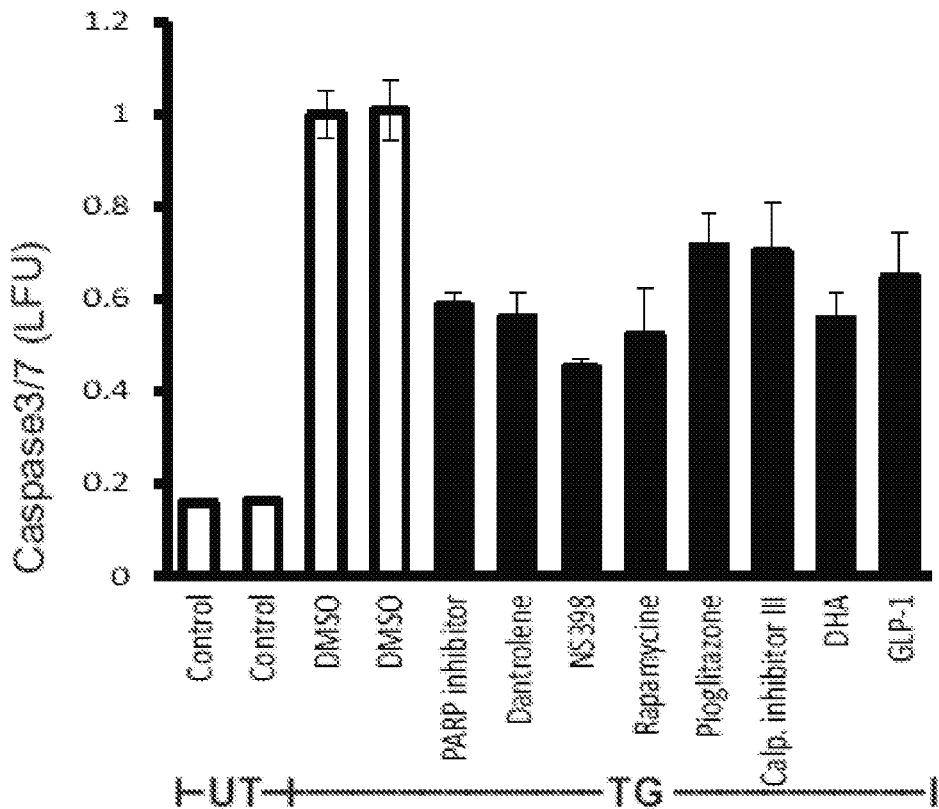
FIG. 8A is a graph illustrating apoptosis of INS-1 832/13 cells were pretreated with DMSO or various compounds that suppress thapsigargin mediated cell death.

The results shown above demonstrate that the pathway leading to calpain-2 activation provides potential therapeutic targets for Wolfram syndrome, such as leakage of ER calcium to the cytosol. To test this concept, a small-scale screen was performed to identify chemical compounds that could prevent cell death mediated by thapsigargin, a known inhibitor for ER calcium ATPase. INS-1 823/13 cells were pretreated with DMSO or drugs for 24 hours the incubated in media containing 2 nM of thapsigargin (TG) overnight. Apoptosis was detected by caspase 3/7-Glo luminescence. Among 73 well-characterized chemical compounds that we tested (Table 3), eight compounds could significantly suppress thapsigargin mediated cell death. These eight compounds were PARP Inhibitor, dantrolene sodium, NS398, rapamycin, pioglitazone, calpain inhibitor III, docosahexaenoic acid (DHA), and GLP-1 (FIG. 8A).

TABLE 3

Chemical compounds used for a screen targeting the ER calcium homeostasis.

| No. | Drug | Treatment Concentration |
| --- | --- | --- |
| 1 | Nicotinamide (Vitamin B3) | 10 µM |
| 2 | Valproic acid | 10 µM |
| 3 | Sodium tauroursodeoxycholate (TUDCA) | 10 µM |
| 4 | (−)-Riboflavin (Vitamin B2, Vitamin G) | 10 µM |
| 5 | Thiamine hydrochloride (Vitamin B1 hydrochloride) | 10 µM |
| 6 | Memantine hydrochloride | 10 µM |
| 7 | (±)-α-Lipoic acid | 10 µM |
| 8 | Kynurenic acid | 10 µM |
| 9 | Folic acid | 10 µM |
| 10 | Idebenone | 10 µM |
| 11 | Acetovanillone (Apocynin) | 10 µM |
| 12 | Aspirin | 10 µM |
| 13 | Pyridoxine hydrochloride | 10 µM |
| 14 | Dextromethorphan hydrobromide | 10 µM |
| 15 | 2,3-Pyridinedicarboxylic acid (DPA) | 10 µM |
| 16 | R-(−)-Deprenyl hydrochloride (Selegiline hydrochloride) | 10 µM |
| 17 | NS-398 | 10 µM |
| 18 | 4-Aminobenzoic acid (PABA, Vitamin Bx, Vitamin H1) | 10 µM |
| 19 | Biotin | 10 µM |
| 20 | D-Pantothenic acid hemicalcium salt(Vitamin B5) | 10 µM |
| 21 | Chondroitin sulfate A sodium salt from bovine trachea | 10 µg/mL |
| 22 | Ebselen | 10 µM |
| 23 | 4-Phenyl-1-(4-phenylbutyl)piperidine maleate | 10 µM |
| 24 | Minocycline hydrochloride | 10 µM |
| 25 | Pravastatin sodium salt hydrate | 10 µM |
| 26 | N-tert-Butyl-α-phenylnitrine (PBN) | 10 µM |
| 27 | Curcumin | 10 µM |
| 28 | TRO19622(Olesoxime) | 10 µM |
| 29 | Pyridoxamine dihydrochloride | 10 µM |
| 30 | Pyridoxal hydrochloride | 10 µM |
| 31 | Fibroblast Growth factor-Basic human | 100 ng/mL |
| 32 | Bryostatin1 | 100 nM |
| 33 | Brain derived neurotrophic factor human | 100 ng/mL |
| 34 | SRP4988 (PEDF) | 100 ng/mL |
| 35 | Erythropoietin | 0.1 UN/mL |
| 36 | Clioquinol | 10 µM |
| 37 | Kenpaullone | 10 µM |
| 38 | PARP Inhibitor III, DPQ | 10 µM |
| 39 | Glial Cell Line-derived Neurotrophic Factor human | 100 ng/mL |
| 40 | Ciliary Neurotrophic Factor, human | 100 ng/mL |
| 41 | Nitric Oxide Synthase, Neuronal Inhibitor 1 | 10 µM |
| 42 | Riluzole | 10 µM |
| 43 | Creatine | 10 µM |
| 44 | Anisomycin from streptomyces griseolus | 10 µM |
| 45 | NE 100 hydrochloride | 10 µM |
| 46 | Phenytoin | 10 µM |
| 47 | Cyclosporin A (CsA) | 300 nM |
| 48 | FK506 | 300 nM |
| 49 | Rapamycin | 10 µM |
| 50 | Docosahexaenoic acid | 10 µM |
| 51 | Glucagon-like peptide-1 (GLP-1) | 50 nM |
| 52 | Diazoxide | 300 µM |
| 53 | Glibenclamide | 100 µM |
| 54 | 2-Aminoethoxydiphenyl borate (2-APB) | 200 nM |
| 55 | Interleukin-1 receptor antagonist (IL-1RA) | 100 ng/mL |
| 56 | Retinol | 10 µM |
| 57 | GW5015-16 | 10 µM |
| 58 | GW9508 | 10 µM |
| 59 | Etomoxir | 20 µM |
| 60 | Verapamil | 20 µM |
| 61 | Metformin | 44 µM |
| 62 | AICAR | 10 µM |
| 63 | Pioglitazone | 10 µM |
| 64 | Troglitazone | 10 µM |
| 65 | N-Acetyl D-sphingosine | 10 µM |
| 66 | Dihydroceramide | 10 µM |
| 67 | Fumonisin B1 | 10 µM |
| 68 | ROS inhibitor | 100 µM |
| 69 | S-nitroso-N-acetyl-D,L-penicillamine | 1 mM |
| 70 | Dantrolene sodium | 10 µM |
| 71 | Bcl-XL BH4 human | 1 µM |
| 72 | Calpain Inhibitor III | 1 µM |
| 73 | Salubrinal | 25 µM |

GLP-1, pioglitazone, and rapamycin are FDA approved drugs, and have been shown to confer protection against ER stress-mediated cell death. Dantrolene is another FDA approved drug clinically utilized for muscle spasticity and malignant hyperthermia. Though previous studies have shown that dantrolene is an inhibitor for the ER-localized ryanodine receptors and suppresses leakage of calcium from the ER to the cytosol, it was unknown whether dantrolene could be used to confer protection against cell death in Wolfram syndrome.

Figure 8B:
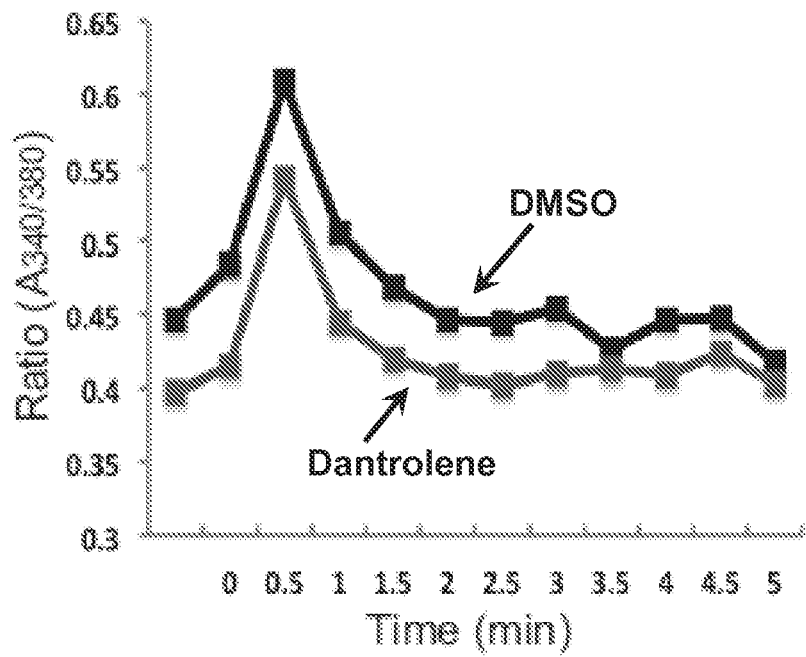
FIG. 8B is a graph illustrating changes in cytosolic calcium levels of INS-1832/13 cells untreated or treated with dantrolene.
Figure 8C:
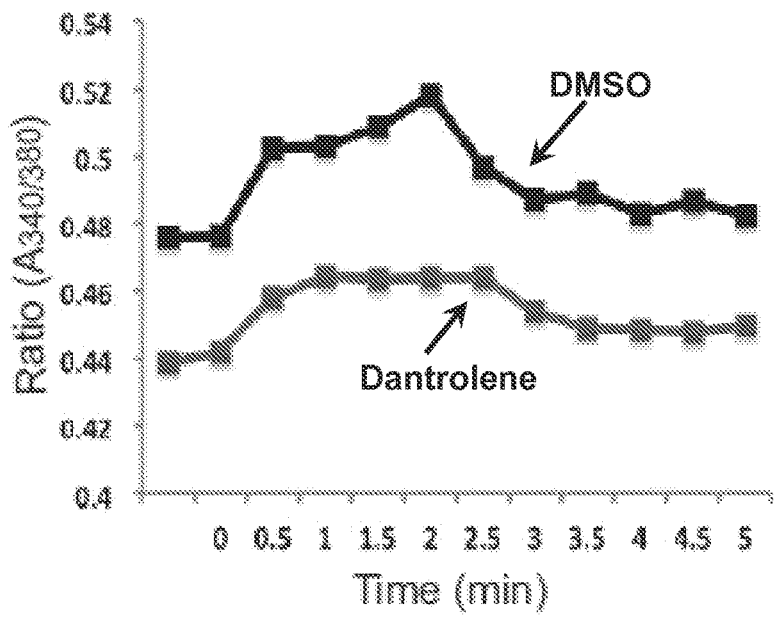
FIG. 8C is a graph illustrating changes in cytosolic calcium levels of NSC34 cells untreated or treated with dantrolene.

First, the question of whether dantrolene could decrease cytoplasmic calcium levels was tested. INS-1 832/13 and NSC34 cells were untreated or treated with 10 µM dantrolene for 24 hours. Cytoplasmic calcium levels were measured by Fura-2 calcium indicator over a period of 5 minutes. Thapsigargin (1 µM) was added at time 0. It was found that dantrolene treatment decreased cytosolic calcium levels in INS-1 832/13 and NSC34 cells (FIGS. 8B and 8C, respectively).

Figure 8D:
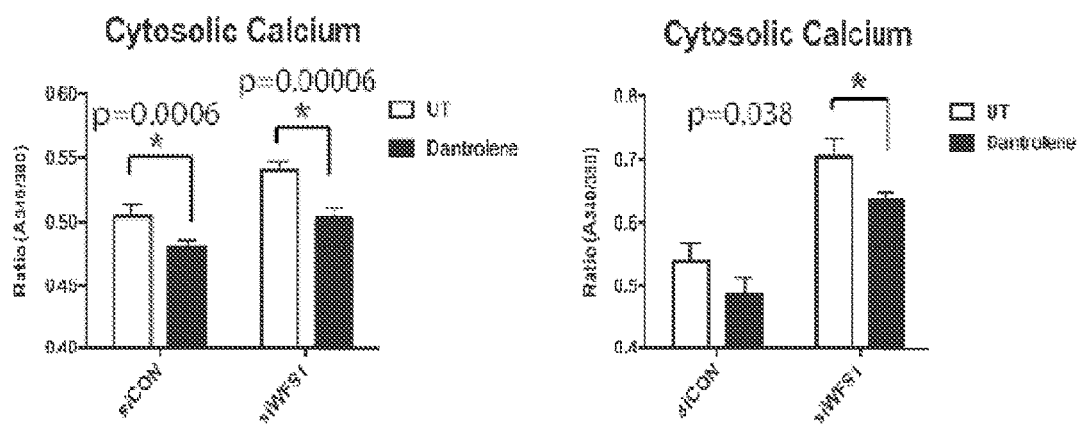
FIG. 8D are graphs illustrating cytosolic calcium levels in control and WFS1 deficient INS-1 832/13 and NSC34 cells untreated or treated with dantrolene.

Next, it was necessary to determine if dantrolene could restore cytosolic calcium levels in WFS1-deficient cells. RNAi-mediated WFS1 knockdown increased cytosolic calcium levels relative to control cells, and dantrolene treatment (10 μM for 24 hours) restored cytosolic calcium levels in WFS1-knockdown INS-1 832/13 cells (FIG. 8D, left panel) as well as WFS1-knockdown NSC34 cells (FIG. 8D, right panel) (n=6, *P<0.05).

Example 8: Protection of WFS1 Deficient Cells

Figure 9A:
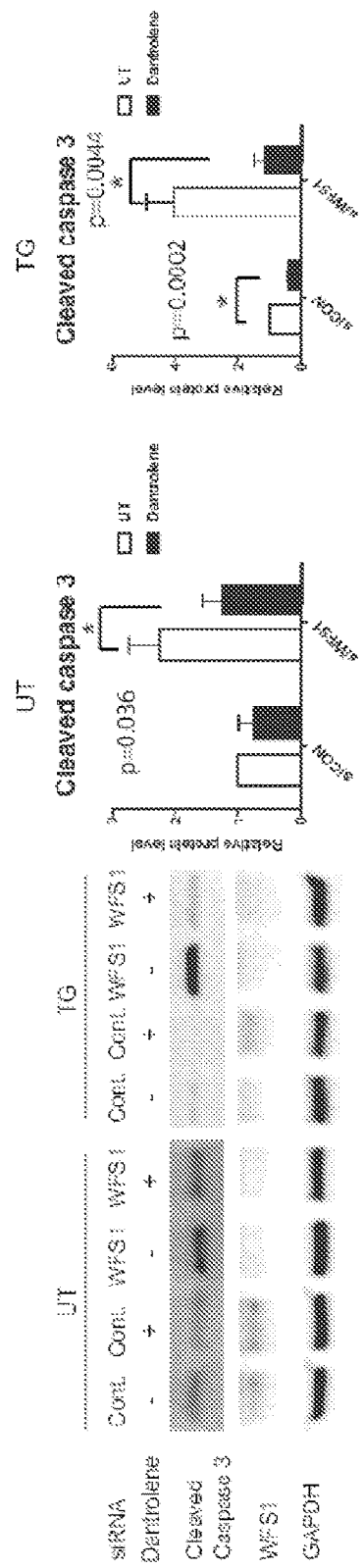
FIG. 9A is a depiction of an immunoblot of INS-1 832/13 cells transfected with scrambled siRNA or siRNA against WFS1, untreated or treated with dantrolene and graphs illustrating a changes in expression levels of cleaved caspase 3.
Figure 9B:
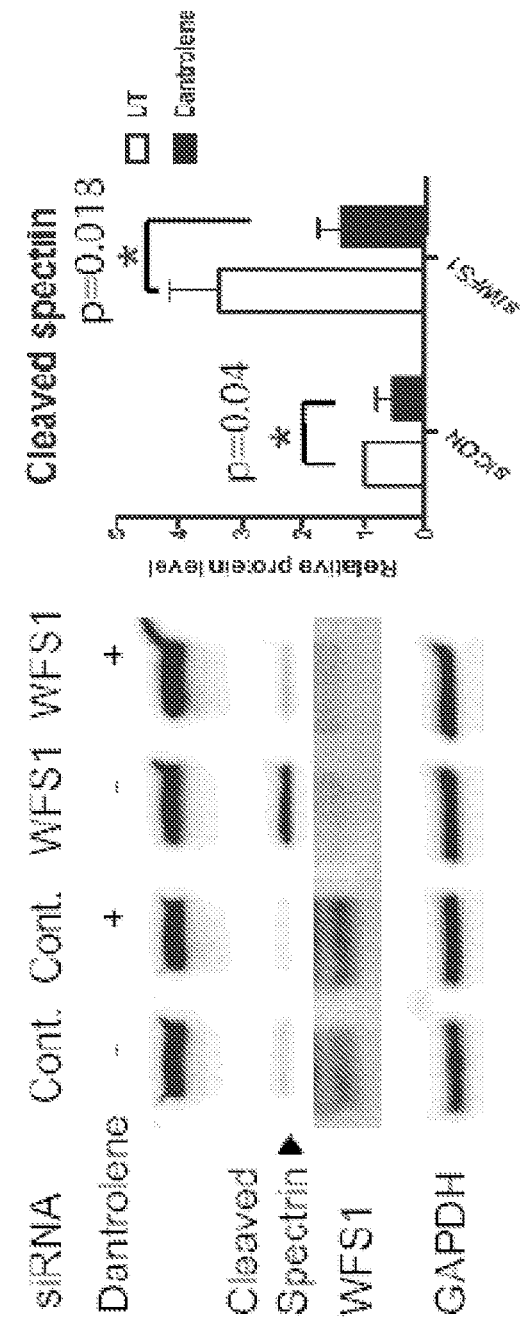
FIG. 9B is a depiction of an immunoblot of INS-1 832/13 cells transfected with scrambled siRNA or siRNA against WFS1, untreated or treated with dantrolene and a graph illustrating a change in expression levels of cleaved spectin.

In order to determine whether dantrolene conferred protection in WFS1 deficient cells and WFS1 silenced INS-1 832/13 cells were treated with dantrolene. INS-1 832/13 cells were transfected with scrambled siRNA or siRNA directed against WFS1. Cells were untreated or treated with 10 μM dantrolene for 48 hours, then incubated in media containing 0.5 μM thapsigargin for 6 hours. Expression levels of cleaved caspase-3 under untreated and thapsigargin treated conditions (FIG. 9A, left panel) were quantified and shown in FIG. 9A, center and right panels (n=3, *P<0.05). Protein levels of cleaved spectrin, WFS1, and GAPDH were analyzed by immunoblotting (FIG. 9B, left panel) and quantified (FIG. 9B, right panel) (n=3, *P<0.05). Dantrolene treated cells resulted in suppression of apoptosis and calpain activity.

Figure 9C:
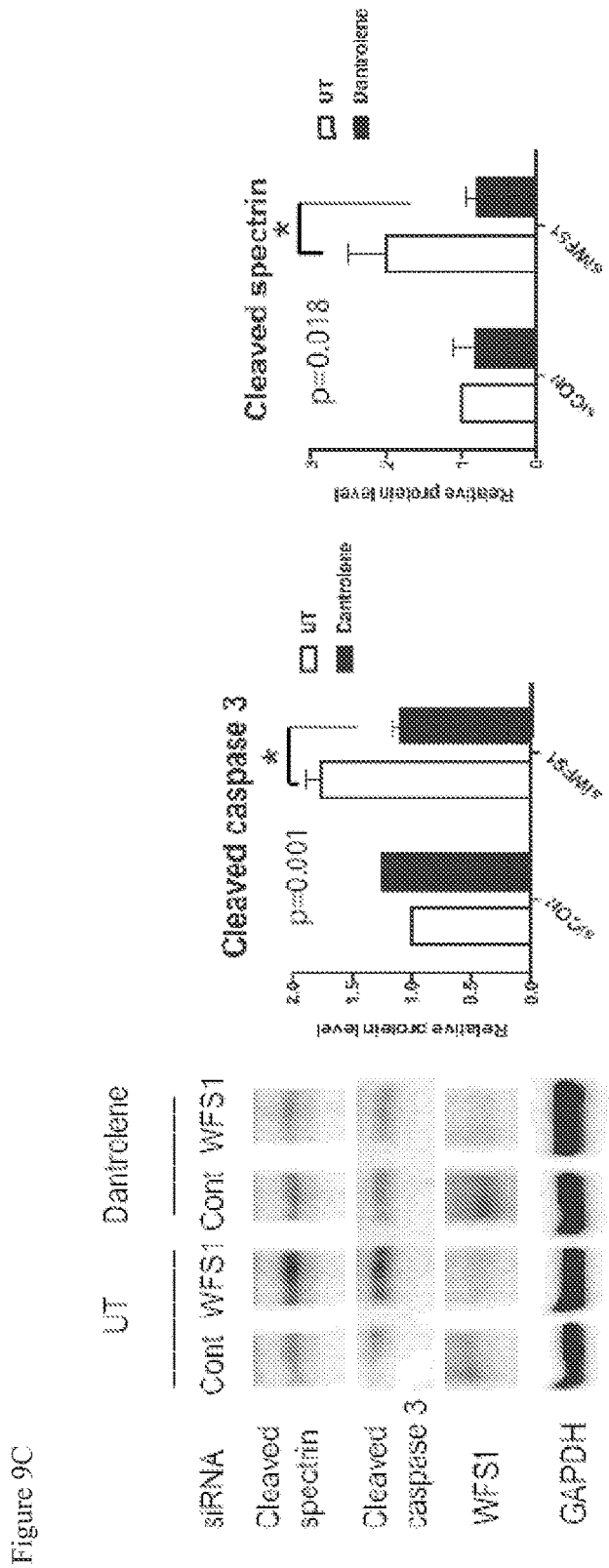
FIG. 9C is a depiction of an immunoblot of NSC34 cells transfected with scrambled siRNA or siRNA against WFS1 untreated or treated with dantrolene and graphs illustrating changes in expression levels of cleaved capase 3 and cleaved spectrin.

NSC34 cells were transfected with scrambled siRNA or siRNA directed against WFS1, then untreated or treated with 10 μM dantrolene for 24 hours. Protein levels of cleaved spectrin, cleaved caspase-3, WFS2, and GAPDH were determined by immunoblotting (FIG. 8G, left panel) and quantified (FIG. 9C, right panel) (n=3, *P<0.05). Dantrolene treatment also prevented calpain activation and cell death in WFS1-knockdown NSC34 cells (FIG. 9C).

Example 9: ER Calcium Homeostasis in β Cells

In to determine if danotrolene affects ER calcium homeostasis, cells were treated with ryanodine or dantrolene. INS-1 832/13 cells were transfected with scrambled siRNA or WRFS1 siRNA. After 24 hours post-transfection, cells were untreated or treated with 2 μM ryanodine for 24 hours. Cleaved caspase-3, WFS1, and GAPDH levels were monitored by immunoblotting (FIG. 10A, left panel) and quantified (FIG. 8H, right panel). INS-1 832/13 cells (FIG. 10B) and NSC34 cells (FIG. 10C) were transfected with scrambled siRNA or WRFS2 siRNA. After 24 hours post transfection, cells were untreated or treated with 10 μM dantrolene for 24 hours. Cleaved caspase-3, WFS2, and GAPDH levels were monitored by immunoblotting. Quantification of cleaved caspase 3 protein levels are shown in FIGS. 10D and 10E, right panels (n=3, *P<0.05).

Sarco/endoplasmic reticulum calcium transport ATPase (SERCA) activity was measured in HEK293 cells stably expressing scrambled sequence (cont.) or shRNA directed against WFS1. SERCA activity for control and shWFS1 cells is shown in FIG. 10D (wild-type, n=6, WFS1 knockout, n=7, *P<0.05). Protein levels of WFS1 and actin were monitored in HEK293 cells stably expressing scrambled shRNA (cont.) or shRNA directed against WFS1 (FIG. 10E, left panel) and were quantified (FIG. 10E, right panel) (n=3, *P<0.05).

RNAi-mediated WFS1 knockdown HEK293 cells significantly reduced the activation levels of SERCA, indicating that WFS1 may play a role in the modulation of SERCA activation and ER calcium levels.

INS-1 832/13 cells that stably express D1ER were treated with digitonin and ethylene glycol tetraacetic acid (EGTA) which causes the minimum value of FRET/CFP ratio, FIG. 10F. Additionally, cells treated with digitonin and $CaCl_2$ led to the maximum value of FRET/CFP ratio, FIG. 10F.

FRET/CFP ratio was decreased in INS-1 832/13 cells treated with thapsigargin in a dose-dependent manner (FIG. 10G). Additionally, the rates of ER calcium-depleted cells increased in cells treated with thapsigargin in a dose-dependent manner (FIG. 10G).

Example 10: Human Brain Tissue

To confirm these observations in patient cells, neural progenitor cells derived from iPS cells of a Wolfram syndrome subject and an unaffected parent were pretreated with dantrolene, and then treated with thapsigargin (TG). Wolfram patient neural progenitor cells were pretreated with or without 10 μM dantrolene for 48 hours. Then cells were treated with 0.125 μM thapsigargin for 20 hours. Apoptosis was monitored by immunoblotting (FIG. 11A, left panel). Quantification of cleaved caspase-3 protein levels are indicated in FIG. 11A, right panel. Thapsigargin-induced cell death was increased in neural progenitor cells derived from the Wolfram syndrome subject as compared to those derived from the unaffected parent, and dantrolene could prevent cell death in the subject iPSC-derived neural progenitor cells.

Example 11: Wolfram Syndrome Mouse Model

In addition, brain-specific WSF1 knockout mice were treated with dantrolene and evidence of suppressed calpain activation in brain lysates from these mice was observed. Control and WFS1 brain specific knockout mice were treated with water or dantrolene (20 mg/kg) for 4 weeks. Brain lysates of these mice were examined by immunoblotting. Protein levels of cleaved spectrin and GAPDH were monitored (FIG. 12A, left panel) and quantified (FIG. 12A, right panel) (n>3, *P<0.05). These results indicate that dantrolene can prevent cell death in Wolfram syndrome by suppressing calpain activation. Additionally, dantrolene treatment did not block cell death mediated by WFS2 knockdown, showing that WFS2 does not directly alter the ER calcium homeostasis.

β-cell specific knockout mice were used to determine if dantrolene could improve glucose tolerance. WSF1 beta cell-specific knockout mice were divided into two test groups consisting of 10 mice, 8 weeks old. Subjects in test group 1 were injected (intraperitoneal) with 6 mg/kg dantrolene for 5 days per week for up to 18 weeks. Subjects in test group 2 were injected (intraperitoneal) with 0.9% saline. Additionally, 10 Littermate control mice of similar age were injected (intraperitoneal) with 0.9% saline.

Weekly non-fasting blood glucose levels and body weight were measured throughout the course of the study. Intraperitoneal glucose tolerance test (IPGTT) was performed on week 0, 13, and 18. Blood glucose levels were obtained over a period of time following injection of a 2 g/kg dextrose solution at week 13 (FIG. 13A) and at week 18 (FIG. 13B).

An average blood glucose level for the three groups throughout the course of the study is shown in FIG. 13C. Body weight of all three groups throughout the course of the study is shown in FIG. 13D.

Example 12: Dantrolene Prevents ER Stress- and Cytokine-Induced β Cell Death To determine whether dantrolene can prevent ER calcium depletion and confer protection against ER stress-mediated cell death in a cell model of type 1 diabetes. INS1E cells were untreated or treated with dantrolene (100 nM), challenged with thapsigargin (10 nM for 24 hours) or an inflammatory cytokine (50 ng/mL), and then the cells were monitoring for cell death via a caspase 3/7 activity assay. Treatment with dantrolene prevented thapsigargin-induced (FIG. 14A) and cytokine induced (FIG. 14B) β cell death.

The following publications are hereby incorporated herein by reference for all relevant purposes.

1. Ron D et al. Signal integration in the endoplasmic reticulum unfolded protein response, Nature reviews. Molecular cell biology, 2007, 8(7): 519-529.
2. Tabas I et al. Integrating the mechanisms of apoptosis induced by endoplasmic reticulum stress, Nature cell biology, 2011, 13(3): 184-190.
3. Hetz C et al. (2013), Targeting the unfolded protein response in disease, Nature reviews. Drug discovery, 2013, 12(9): 703-719.
4. Wang S et al. The impact of the unfolded protein response on human disease. The Journal of cell biology, 2012, 197(7): 857-867.
5. Fonseca S G et al. WFS1 Is a Novel Component of the Unfolded Protein Response and Maintains Homeostasis of the Endoplasmic Reticulum in Pancreatic beta-Cells. The Journal of biological chemistry, 2005, 280(47): 39609-39615.
6. Fonseca S G et al. Wolfram syndrome 1 gene negatively regulates ER stress signaling in rodent and human cells. The Journal of clinical investigation, 2010, 120(3): 744-755.
7. Barrett T G et al. Neurodegeneration and diabetes: UK nationwide study of Wolfram (DIDMOAD) syndrome. Lancet, 1995, 346(8988): 1458-1463.
8. Wolfram D J et al. Diabetes mellitus and simple optic atrophy among siblings: report of four cases. Mayo Clinic Proc, 1938, 13: 715-718.
9. Urano F. Diabetes: Targeting endoplasmic reticulum to combat juvenile diabetes. Nature Reviews Endocrinology, 2014, 10: 129-130.
10. Hershey T et al. Early Brain Vulnerability in Wolfram Syndrome. PloS one, 2012, 7(7): e40604.
11. Marshall B A et al. Phenotypic characteristics of early Wolfram syndrome. Orphanet journal of rare diseases, 2013, 8(1): 64.
12. Inoue H et al. A gene encoding a transmembrane protein is mutated in subjects with diabetes mellitus and optic atrophy (Wolfram syndrome). Nature genetics, 1998, 20(2): 143-148.
13. Amr S et al. A homozygous mutation in a novel zinc-finger protein, ERIS, is responsible for Wolfram syndrome 2. American journal of human genetics, 2007, 81(4): 673-683.
14. Chen Y F et al. Cisd2 deficiency drives premature aging and causes mitochondria-mediated defects in mice. Genes Dev, 2009, 23(10): 1183-1194.
15. Wiley S E et al. Wolfram Syndrome protein, Miner1 regulates sulphydryl redox status, the unfolded protein response, and Ca2+ homeostasis. EMBO molecular medicine, 2013, 5(6): 904-918.
16. Shang L et al. Beta-cell dysfunction due to increased ER stress in a stem cell model of Wolfram syndrome. Diabetes, 2014, 63(3): 923-933.
17. Sandhu M S et al. Common variants in WFS1 confer risk of type 2 diabetes. Nature genetics, 2007, 39(8): 951-953.
18. Bonnycastle L L et al. (2013) Autosomal dominant diabetes arising from a wolfram syndrome 1 mutation. Diabetes, 2013, 62(11): 3943-3950.
19. Goll D E et al. et al. The calpain system. Physiol Rev, 2003, 83(3): 731-801.
20. Tan Y et al. Ubiquitous calpains promote caspase-12 and JNK activation during endoplasmic reticulum stress-induced apoptosis. The Journal of biological chemistry, 2006, 281(23): 16016-16024.
21. Tan Y et al. Ubiquitous calpains promote both apoptosis and survival signals in response to different cell death stimuli. The Journal of biological chemistry, 2006, 281 (26): 17689-17698.
22. Nakagawa T et al. Cross-talk between two cysteine protease families. Activation of caspase-12 by calpain in apoptosis. The Journal of cell biology 2000, 150(4): 887-894.
23. Barrett T G et al. Wolfram (DIDMOAD) syndrome. J Med Genet, 1997, 34(10): 838-841.
24. Hara T et al. Calcium Efflux from the Endoplasmic Reticulum Leads to beta-Cell Death. Endocrinology, 2014, 155(3): 758-768.
25. Takei D et al. WFS1 protein modulates the free Ca(2+) concentration in the endoplasmic reticulum. FEBS Lett, 2006, 580(24): 5635-5640.
26. Liu M C et al. Comparing calpain- and caspase-3-mediated degradation patterns in traumatic brain injury by differential proteome analysis. The Biochemical journal, 2006, 394: 715-725.
27. Liu M C et al. Extensive degradation of myelin basic protein isoforms by calpain following traumatic brain injury. Journal of neurochemistry, 2006, 98(3): 700-712.
28. Takahashi K et al. Induction of pluripotent stem cells from mouse embryonic and adult fibroblast cultures by defined factors. Cell, 2006, 126(4): 663-676.
29. Yusta B et al. GLP-1 receptor activation improves beta cell function and survival following induction of endoplasmic reticulum stress. Cell Metab, 2006 4(5): 391-406.
30. Akiyama M et al. Increased insulin demand promotes while pioglitazone prevents pancreatic beta cell apoptosis in Wfs1 knockout mice. Diabetologia, 2009, 52(4): 653-663.
31. Bachar-Wikstrom E et al. Stimulation of autophagy improves endoplasmic reticulum stress-induced diabetes. Diabetes, 2013, 62(4): 1227-1237.
32. Dykes MH. Evaluation of a muscle relaxant: dantrolene sodium (Dantrium). JAMA: the journal of the American Medical Association, 1975, 231(8): 862-864.
33. Wei H et al. Dantrolene is cytoprotective in two models of neuronal cell death. Journal of neurochemistry, 1996, 67(6): 2390-2398.
34. Luciani D S et al. Roles of IP3R and RyR Ca2+ channels in endoplasmic reticulum stress and beta-cell death. Diabetes, 2009, 58(2): 422-432.
35. Hotamisligil G S. Endoplasmic reticulum stress and atherosclerosis. Nature medicine, 2010, 16(4): 396-399.
36. Hotamisligil G S. Endoplasmic reticulum stress and the inflammatory basis of metabolic disease. Cell, 2010, 140(6): 900-917.

37. Ozcan L et al. Role of endoplasmic reticulum stress in metabolic disease and other disorders. Annual review of medicine, 2012, 63: 317-328.
38. Riggs A C et al. Mice conditionally lacking the Wolfram gene in pancreatic islet beta cells exhibit diabetes as a result of enhanced endoplasmic reticulum stress and apoptosis. Diabetologia, 2005, 48(11): 2313-2321.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

Having described the invention in detail, it will be apparent that modifications and variations are possible without departing from the scope of the invention defined in the appended claims.

What is claimed is:

1. A method of treating Wolfram Syndrome in a subject in need thereof comprising administering to the subject a therapeutically effective amount of a ryanodine receptor inhibitor, wherein the ryanodine receptor inhibitor comprises azumolene or a pharmaceutically acceptable salt or hydrate thereof.

2. The method of claim 1, wherein the ryanodine receptor inhibitor is administered intravenously in an amount of from about 0.05 mg to about 30 mg per kg of body weight.

3. The method of claim 1, wherein the ryanodine receptor inhibitor is administered orally in an amount of from about 0.1 mg to about 75 mg per kg of bodyweight.

4. The method of claim 1, wherein the ryanodine receptor inhibitor is administered in a composition further comprising a pharmaceutically acceptable carrier.

5. The method of claim 4, wherein the composition further comprises at least one second active agent, wherein the second active agent modulates the transport of calcium (Ca2+) ions to and/or from the endoplasmic reticulum in a cell.

6. The method of claim 1, wherein the subject is a human.

---

SEQUENCE LISTING

<160> NUMBER OF SEQ ID NOS: 4

<210> SEQ ID NO 1
<211> LENGTH: 18
<212> TYPE: RNA
<213> ORGANISM: Artificial Sequence
<220> FEATURE:
<223> OTHER INFORMATION: Synthetic

<400> SEQUENCE: 1
caacagaagg auagcuug                                                     18

<210> SEQ ID NO 2
<211> LENGTH: 18
<212> TYPE: RNA
<213> ORGANISM: Artificial Sequence
<220> FEATURE:
<223> OTHER INFORMATION: Synthetic

<400> SEQUENCE: 2
cgaaaguagu gaaugaaa                                                     18

<210> SEQ ID NO 3
<211> LENGTH: 18
<212> TYPE: RNA
<213> ORGANISM: Artificial Sequence
<220> FEATURE:
<223> OTHER INFORMATION: Synthetic

<400> SEQUENCE: 3
ccgaggaggu ugaaagua                                                     18

<210> SEQ ID NO 4
<211> LENGTH: 19
<212> TYPE: RNA
<213> ORGANISM: Artificial Sequence
<220> FEATURE:
<223> OTHER INFORMATION: Synthetic

<400> SEQUENCE: 4
guuugaccgc uacaaguuu                                                    19

7. A method of treating Wolfram Syndrome in a human subject in need thereof comprising administering to the subject a therapeutically effective amount of a composition comprising dantrolene or a pharmaceutically acceptable salt or hydrate thereof, wherein the human subject has an age that is 16 years or less.

8. The method of claim 7, wherein the composition comprises dantrolene sodium.

9. The method of claim 7, wherein the composition further comprises a pharmaceutically acceptable carrier.

10. The method of claim 8, wherein the dantrolene sodium is administered intravenously in an amount of from about 0.05 mg to about 30 mg per kg of body weight.

11. The method of claim 8, wherein the dantrolene sodium is administered orally in an amount of from about 0.1 mg to about 75 mg per kg of bodyweight.

12. The method of claim 7, further comprising administering at least one second active agent.

13. The method of claim 12, wherein the second active agent modulates the transport of calcium (Ca2+) ions to and/or from the endoplasmic reticulum in a cell.

14. The method of claim 12, wherein the second active agent comprises a compound that enhances the activity of sarco/endoplasmic reticulum calcium adenosine triphosphatase (SERCA) pumps.

15. The method of claim 14, wherein the second active agent comprises pioglitazone.

16. A method of treating Wolfram Syndrome in a human subject in need thereof consisting of administering to the subject a therapeutically effective amount of a composition consisting of dantrolene or a pharmaceutically acceptable salt or hydrate thereof and one or more pharmaceutically acceptable carriers.

17. The method of claim 16, wherein the dantrolene or a pharmaceutically acceptable salt or hydrate thereof comprises dantrolene sodium.

18. A method of treating Wolfram Syndrome in a human subject in need thereof comprising administering to the subject a therapeutically effective amount of a composition comprising dantrolene or a pharmaceutically acceptable salt or hydrate thereof, wherein the subject does not have Type 1 or Type 2 diabetes.

19. The method of claim 18, wherein the composition comprises dantrolene sodium.

20. The method of claim 19, wherein the dantrolene sodium is administered intravenously in an amount of from about 0.05 mg to about 30 mg per kg of body weight or orally in an amount of from about 0.1 mg to about 75 mg per kg of bodyweight.

* * * * *